(12) United States Patent
Sundermann et al.

(10) Patent No.: US 7,273,952 B2
(45) Date of Patent: Sep. 25, 2007

(54) SUBSTITUTED C-CYCLOHEXYLMETHYLAMINE DERIVATIVES

(75) Inventors: Bernd Sundermann, Aachen (DE); Corinna Maul, Aachen (DE); Helmut Buschmann, Aachen (DE); Michael Finkam, Aachen (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 94 days.

(21) Appl. No.: 10/402,260

(22) Filed: Mar. 31, 2003

(65) Prior Publication Data

US 2003/0232891 A1 Dec. 18, 2003

Related U.S. Application Data

(63) Continuation of application No. PCT/EP01/11246, filed on Sep. 28, 2001.

(30) Foreign Application Priority Data

Sep. 29, 2000 (DE) ............................... 100 49 481

(51) Int. Cl.
| | |
|---|---|
| C07C 211/19 | (2006.01) |
| C07C 69/76 | (2006.01) |
| C07C 233/68 | (2006.01) |
| C07C 67/02 | (2006.01) |
| C07D 241/04 | (2006.01) |
| C07D 333/16 | (2006.01) |
| C07D 307/48 | (2006.01) |
| A61K 31/34 | (2006.01) |
| A61K 31/38 | (2006.01) |
| A61K 31/135 | (2006.01) |
| A61K 31/165 | (2006.01) |
| A61K 31/195 | (2006.01) |
| A61K 31/497 | (2006.01) |

(52) U.S. Cl. .................. 564/337; 564/166; 544/399; 549/75; 549/484; 560/107; 560/250; 560/252; 514/252.12; 514/438; 514/471; 514/561; 514/619; 514/650

(58) Field of Classification Search .................. None
See application file for complete search history.

(56) References Cited

U.S. PATENT DOCUMENTS

| | | | |
|---|---|---|---|
| 3,975,436 A | 8/1976 | Fletcher et al. | |
| 4,101,578 A * | 7/1978 | Bock et al. | .................. 564/454 |
| 5,414,129 A | 5/1995 | Cherkez et al. | |
| 5,733,936 A | 3/1998 | Buschmann et al. | |
| 5,801,201 A | 9/1998 | Graudums et al. | |
| 5,811,582 A | 9/1998 | Buschmann et al. | |
| 2003/0021763 A1 | 1/2003 | Germann et al. | |

FOREIGN PATENT DOCUMENTS

| | | |
|---|---|---|
| BE | 615646 | 4/1962 |
| DE | 19547766 | 6/1997 |
| EP | 0780369 | 6/1997 |
| EP | 0753506 B1 | 8/1999 |
| GB | 997339 | 7/1965 |
| WO | WO99/50225 | 10/1999 |
| WO | WO99/61405 | 12/1999 |
| WO | WO 0157232 | 8/2001 |

OTHER PUBLICATIONS

Database CAPLUS on STN, Acc. No. 1983:522648, Rykowski, Polish Journal of Chemistry (1981), 55(11), p. 2271-2278 (abstract).*
Chemical Abstracts, "The Reactions of Certain Pinenes with Dimethylamine and Formaldehyde", vol. 94, No. 21, May 25, 1981.
Gais et al., "Enzymatic Resolution of Analgesics: δ-hydroxytramadol, ε-hydroxytramadol and O-desmethyltramadol", Tetrahedron: Asymmetry, vol. 11 (2000), pp. 917-928.
Reichert et al., "Aminomethylierungsprodukte alkylsubstituierter Cyclohexanone und ihre Umsetzungen", Drug Research, vol. 13, No. 11 (1963), pp. 991-999.
Tetrahecdron Asym, 11, 2000, S.917-928 (Previously Presented In IDS dated Sep. 24, 2003).
Tetrahecdron Asym, CA, vol. 101, Nr.23053n, 1984.
Tetrahecdron Asym, CA, vol. 94, Nr.175265h, 1981.
Tetrahecdron Asym, CA vol. 87, Nr.52866c, 1977.

* cited by examiner

*Primary Examiner*—Brian Davis
(74) *Attorney, Agent, or Firm*—Crowell & Moring LLP

(57) ABSTRACT

Substituted C-cyclohexylmethylamine derivatives, methods for the production thereof, pharmaceuticals containing said compounds, the use of substituted C-cyclohexylmethylamine derivatives for producing pharmaceuticals, and method of pain treatment using the pharmaceuticals.

56 Claims, No Drawings

SUBSTITUTED C-CYCLOHEXYLMETHYLAMINE DERIVATIVES

CROSS REFERENCE TO RELATED APPLICATIONS

The present application is a continuation of International Patent Application No. PCT/EP01/11246, filed Sep. 28, 2001, designating the United States of America and published in German as WO 02/30870, the entire disclosure of which is incorporated herein by reference. Priority is claimed based on Federal Republic of Germany Patent Application No. 100 49 481.1, filed Sep. 29, 2000.

BACKGROUND AND SUMMARY OF THE INVENTION

The present invention relates to substituted C-cyclohexylmethylamine derivatives, to methods for their production, to pharmaceutical compositions containing these compounds and to the use of substituted C-cyclohexylmethylamine derivatives for producing pharmaceutical compositions.

The treatment of chronic and non-chronic pain conditions has great importance in medicine. There is a worldwide need for effective methods of treating pain. The urgent need for action for patient-friendly and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Conventional opioids, such as morphine, are extremely effective in the treatment of severe to the severest pain. However, their use is limited by the known side effects, for example respiratory depression, nausea, sedation, constipation and tolerance development. In addition, they are less effective in the event of neuropathic or incidental pain, from which patients with tumours suffer in particular.

An object forming the basis of the invention consisted in providing new analgesic substances which are capable of treating pain, in particular chronic and neuropathic pain.

DESCRIPTION OF THE INVENTION

The invention therefore relates to substituted C-cyclohexylmethylamine derivatives of formula I,

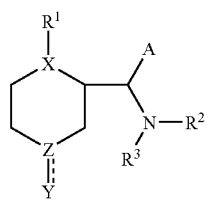

I wherein

A is H; respectively singly or multiply substituted or unsubstituted aryl or heteroaryl;

$R^1$ is respectively saturated or unsaturated, branched or unbranched, singly or multiply substituted or unsubstituted $C_{1-10}$ alkyl or $C_{3-10}$ cycloalkyl; aryl, heteroaryl, aryl bound by saturated or unsaturated $C_{1-3}$ alkyl or $C_{1-3}$ alkylene or ethinyl; $C_{3-10}$ cycloalkyl bound by saturated or unsaturated $C_{1-3}$ alkyl or $C_{1-3}$ alkylene or ethinyl; or heteroaryl bound by saturated or unsaturated $C_{1-3}$ alkyl or $C_{1-3}$ alkylene or ethinyl, respectively unsubstituted or singly or multiply substituted by radicals, which independently of one another are F, Cl, Br, I, $OR^{18}$, $SR^{18}$, $SO_2R^{18}$, $SO_2OR^{18}$, CN, $COOR^{18}$, $NR^{19}R^{20}$; unsubstituted or singly or multiply substituted $C_{1-10}$ alkyl, $C_{3-10}$ cycloalkyl or silyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

wherein $R^{18}$ is H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

$R^{19}$ and $R^{20}$, independent of one another, are H; respectively saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H; unsubstituted or substituted phenyl; saturated or unsaturated, branched or unbranched, unsubstituted or singly or multiply substituted $C_{1-10}$ alkyl;

$R^2$ and $R^3$ independently of one another are H; respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

or the radicals $R^2$ and $R^3$ together represent $CH_2CH_2OCH_2CH_2$, $CH_2CH_2NR^6CH_2CH_2$ or $(CH_2)_{3-6}$, wherein $R^6$ is H; respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

X in formula I has such a meaning that a part of formula I, as depicted in Partial Formula Ia,

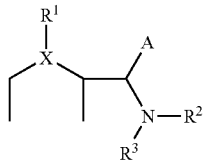

partial formula Ia has the following meanings

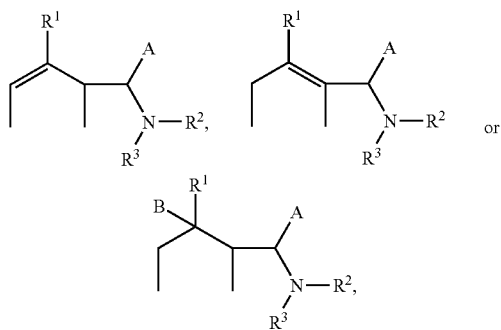

wherein B is OH, OR$^7$, H, F, Cl or NR$^8$R$^9$,
wherein R$^7$ is respectively saturated or unsaturated, branched or unbranched, singly or multiply substituted or unsubstituted C$_{1-10}$ alkyl or C$_{3-10}$ cycloalkyl; respectively singly or multiply substituted or unsubstituted aryl or heteroaryl; or respectively singly or multiply substituted or unsubstituted aryl bound by saturated or unsaturated C$_{1-3}$ alkyl or C$_{1-3}$ alkylene, C$_{3-10}$ cycloalkyl or heteroaryl;

R$^8$ and R$^9$ independently of one another are H; respectively saturated or unsaturated, branched or unbranched, singly or multiply substituted or unsubstituted C$_{1-10}$ alkyl or C$_{3-10}$ cycloalkyl; singly or multiply substituted or unsubstituted aryl or heteroaryl; or respectively singly or multiply substituted or unsubstituted aryl bound by saturated or unsaturated C$_{1-3}$ alkyl or C$_{1-3}$ alkylene, C$_{3-10}$ cycloalkyl or heteroaryl;

or R$^8$ and R$^9$ together form CH$_2$CH$_2$OCH$_2$CH$_2$, CH$_2$CH$_2$NR$^{10}$CH$_2$CH$_2$ or (CH$_2$)$_{3-6}$,
wherein R$^{10}$ is H; respectively saturated or unsaturated, branched or unbranched, singly or multiply substituted or unsubstituted C$_{1-10}$ alkyl or C$_{3-10}$ cycloalkyl; respectively singly or multiply substituted or unsubstituted aryl or heteroaryl; or respectively singly or multiply substituted or unsubstituted aryl bound by saturated or unsaturated C$_{1-3}$ alkyl or C$_{1-3}$ alkylene, C$_{3-10}$ cycloalkyl or heteroaryl, and

is:

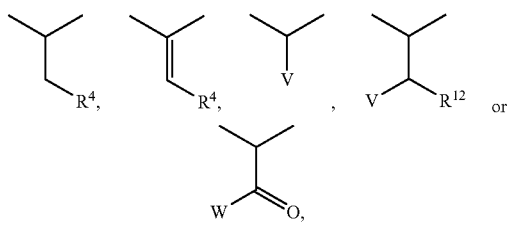

wherein R$^4$ is H, COR$^5$, SO$_2$R$^5$; respectively saturated or unsaturated, branched or unbranched, singly or multiply substituted or unsubstituted C$_{1-10}$ alkyl or C$_{3-10}$ cycloalkyl; respectively singly or multiply substituted or unsubstituted aryl or heteroaryl; or respectively singly or multiply substituted or unsubstituted aryl bound by saturated or unsaturated C$_{1-3}$ alkyl or C$_{1-3}$ alkylene, C$_{3-10}$ cycloalkyl or heteroaryl,
wherein R$^5$ is respectively saturated or unsaturated, branched or unbranched, singly or multiply substituted or unsubstituted C$_{1-10}$ alkyl or C$_{3-10}$ cycloalkyl; respectively singly or multiply substituted or unsubstituted aryl or heteroaryl;
or respectively singly or multiply substituted or unsubstituted aryl bound by saturated or unsaturated C$_{1-3}$ alkyl or C$_{1-3}$ alkylene, C$_{3-10}$ cycloalkyl or heteroaryl,
wherein V is OR$^4$ or NR$^4$R$^{11}$,
wherein W is R$^{11}$, OR$^{12}$ or NR$^{11}$R$^{12}$,
wherein R$^{11}$ and R$^{12}$ independently of one another are H; respectively saturated or unsaturated, branched or unbranched, singly or multiply substituted or unsubstituted C$_{7-10}$ alkyl or C$_{3-10}$ cycloalkyl; respectively singly or multiply substituted or unsubstituted aryl or heteroaryl; or respectively singly or multiply substituted or unsubstituted aryl bound by saturated or unsaturated C$_{1-3}$ alkyl or C$_{1-3}$ alkylene, C$_{3-10}$ cycloalkyl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the illustrated form or in the form of their acids or their bases or in the form of their salts, in particular physiologically acceptable salts, or in the form of their solvates, in particular the hydrates.

The compounds according to the invention exhibit outstanding analgesic properties.

In the context of this invention, alkyl and cycloalkyl radicals are taken to mean saturated and unsaturated (but not aromatic), branched, unbranched and cyclic hydrocarbons which may be unsubstituted or singly or multiply substituted. In this case C$_{1-2}$-alkyl represents C$_1$- or C$_2$-alkyl, C$_{1-3}$-alkyl represents C$_1$-, C$_2$- or C$_3$-alkyl, C$_{1-4}$-alkyl represents C$_1$-, C$_2$-, C$_3$- or C$_4$-alkyl, C$_{1-5}$-alkyl represents C$_1$-, C$_2$-, C$_3$-, C$_4$ or C$_5$-alkyl, C$_{1-6}$-alkyl represents C$_1$-, C$_2$-, C$_3$-, C$_4$-, C$_5$- or C$_6$-alkyl, C$_{1-7}$-alkyl represents C$_1$-, C$_2$-, C$_3$-, C$_4$-, C$_5$-, C$_6$- or C$_7$-alkyl, C$_{1-8}$-alkyl represents C$_1$-, C$_2$-, C$_3$-, C$_4$-, C$_5$-, C$_6$-, C$_7$ or C$_8$-alkyl, C$_{1-10}$-alkyl represents C$_1$-, C$_2$-, C$_3$-, C$_4$-, C$_5$-, C$_6$-, C$_7$-, C$_8$,- C$_9$- or C$_{10}$-alkyl and C$_{1-18}$-alkyl represents C$_1$-, C$_2$-, C$_3$-, C$_4$-, C$_5$-, C$_6$-, C$_7$-, C$_8$-, C$_9$-, C$_{10}$-, C$_{11}$-, C$_{12}$, C$_{13}$-, C$_{14}$-, C$_{15}$-, C$_{16}$-, C$_{17}$- or C$_{18}$-alkyl. Furthermore, C$_{3-4}$-cycloalkyl represents C$_3$- or C$_4$-cycloalkyl, C$_{3-5}$-cycloalkyl represents C$_3$-, C$_4$- or C$_5$-cycloalkyl, C$_{3-6}$-cycloalkyl represents C$_3$-, C$_4$-, C$_5$- or C$_6$-cycloalkyl, C$_{3-7}$-cycloalkyl represents C$_3$-, C$_4$-, C$_5$-, C$_6$-or C$_7$-cycloalkyl, C$_{3-8}$-cycloalkyl represents C$_3$-, C$_4$-, C$_5$-, C$_6$-, C$_7$- or C$_8$-cycloalkyl, C$_{4-5}$-cycloalkyl represents C$_4$- or C$_5$-cycloalkyl, C$_{4-6}$-cycloalkyl represents C$_4$-, C$_5$- or C$_6$-cycloalkyl, C$_{4-7}$-cycloalkyl represents C$_4$-, C$_5$-, C$_6$- or C$_7$-cycloalkyl, C$_{5-6}$-cycloalkyl represents C$_5$- or C$_6$-cycloalkyl and C$_{5-7}$-cycloalkyl represents C$_5$-, C$_6$- or C$_7$-cycloalkyl. With respect to cycloalkyl, the term also comprises saturated cycloalkyls, in which one or two carbon atoms are replaced by a heteroatom, S, N or O. However, the term cycloalkyl also includes singly or multiply, preferably singly, unsaturated cycloalkyls without a heteroatom in the ring, if the cycloalkyl is not an aromatic system. The alkyl and cycloalkyl radicals are preferably ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ and pyrazolinone, oxopyrazolinone, [1,4]dioxan or dioxolan.

In conjunction with alkyl and cycloalkyl—unless explicitly defined otherwise—the term substituted in the context of this invention is taken to mean the substitution of at least one (or more) hydrogen radical(s) by F, Cl, Br, I, $NH_2$, SH or OH, wherein "multiply substituted" or "substituted" with multiple substitution is taken to mean that the substitution is made both on different and on the same atoms multiply with the same or different substituents, for example threefold on the same carbon atom as in the case of $CF_3$ or at different points as in the case of $—CH(OH)—CH=CH—CHCl_2$. Particularly preferred substituents in this case are F, Cl and OH. With respect to cycloalkyl, the hydrogen radical can also be replaced by $OC_{1-3}$ alkyl or $C_{1-3}$ alkyl (singly or multiply substituted or unsubstituted respectively), in particular methyl, ethyl, n-propyl, i-propyl, $CF_3$, methoxy or ethoxy.

The term $(CH_2)_{3-6}$ is taken to mean $—CH_2—CH_2—CH_2—$, $—CH_2—CH_2—CH_2—CH_2—$, $—CH_2—CH_2—CH_2—CH_2—CH_2—$ and $—CH_2—CH_2—CH_2—CH_2—CH_2—CH_2—$, $(CH_2)_{1-4}$ is taken to mean $—CH_2—$, $—CH_2—CH_2—$, $—CH_2—CH_2—CH_2—$ and $—CH_2—CH_2—CH_2—CH_2—$, $(CH_2)_{4-5}$ is taken to mean $—CH_2—CH_2—CH_2—CH_2—$ and $—CH_2—CH_2—CH_2—CH_2—CH_2—$ etc.

An aryl radical is taken to mean ring systems with at least one aromatic ring but without heteroatoms in any of the rings. Examples are phenyl, naphthyl, fluoroanthenyl, fluoroenyl, tetralinyl or indanyl, in particular 9H fluoroenyl or anthracenyl radicals which can be unsubstituted or singly or multiply substituted.

A heteroaryl radical is taken to mean heterocylic ring systems with at least one unsaturated ring which contain one or more heteroatoms selected from the group conisting of nitrogen, oxygen and sulphur and which can also be singly or multiply substituted. Examples of heteroaryls include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolan, benzodioxan, carbazole, indole and quinazoline.

In conjunction with aryl and heteroaryl, substituted is taken to mean the substitution of the aryl or heteroaryl by $R^{23}$, $OR^{23}$ a halogen, preferably F and/or Cl, a $CF_3$, a CN, a $NO_2$, a $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene, wherein the radical $R^{23}$ represents H, a $C_{1-10}$ alkyl, preferably a $C_{1-6}$ alkyl, an aryl or heteroaryl radical or an aryl or heteroaryl radical bound by $C_{1-3}$ alkyl, saturated or unsaturated, or a $C_{1-3}$ alkylene-goup-bound aryl or heteroaryl radical, wherein these aryl or heteroaryl radicals are not themselves substituted by aryl or heteroaryl radicals, and the radicals $R^{24}$ and $R^{25}$, which are the same or different, represent H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-goup-bound aryl or heteroaryl radical, wherein these aryl or heteroaryl radicals must not themselves be substituted by aryl or heteroaryl radicals, or the radicals $R^{24}$ and $R^{25}$ together mean $CH_2CH_2OCH_2CH_2$, $CH_2CH_2HR^{26}CH_2CH_2$ or $(CH_2)_{3-6}$, and wherein
the radical $R^{26}$ represents H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-goup-bound aryl or heteroaryl radical, wherein these aryl or heteroaryl radicals must not themselves be substituted by aryl or heteroaryl radicals.

The term salt is taken to mean any form of the active ingredient according to the invention in which it assumes or is charged with an ionic form and is coupled to a counter ion (a cation or anion) or is in solution. This also includes complexes of the active ingredient with other molecules and ions, in particular complexes by ionic interactions.

The term physiologically acceptable salts with cations or bases is taken to mean, in the context of this invention, salts of at least one of the compounds according to the invention—usually a (deprotonated) acid—as anion with at least one, preferably inorganic, cation which are physiologically acceptable, in particular when applied to humans or other mammals. The salts of the alkaline and alkaline earth metals are preferred, but also with $NH_4^+$, in particular however (mono) or (di) sodium, (mono) or (di) potassium, magnesium or calcium salts.

The term physiologically acceptable salts with anions or acids is taken to mean, in the context of this invention, salts of at least one of the compounds according to the invention—usually protonated, for example on nitrogen—as cation with at least one anion which are physiologically acceptable—in particular when applied to humans or other mammals. In the context of this invention this is taken to mean, in particular, the salt formed with a physiologically acceptable acid, namely salts of the respective active ingredient with inorganic or organic acids which are physiologically acceptable—in particular when applied to humans and/or mammals. Examples of physiologically acceptable salts of certain acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, 1,1-dioxo-1,2,dihydro-1$\lambda^6$-benzo[d]isothiazol-3-on (saccharinic acid), monomethyl sebacic acid, 5-oxo-proline, hexane-1-sulphonic acid, nicotinic acid, 2-, 3- or 4-amino benzoic acid, 2,4,6-trimethyl-benzoic acid, a-lipoic acid, acetyl glycine, acetyl salicic acid, hippuric acid and/or aspartic acid. Hydrochloride salt is particularly preferred.

The analgesic tramadol has been successfully used for years in many countries to treat moderately severe to severe pain. Structurally derived from codeine and originally conceived as a cough mixture, it was found even in early tests that tramadol has a pronounced analgesic efficacy. Nowadays this is explained by the fact that the tramadol metabolite M1, which exhibits a clear affinity to the p subtype of the opiate receptor, is formed rapidly in vivo. However, in contrast to codeine or morphine, the participation of further mechanisms, the inhibition of symptosomatic noradrenaline and serotonin reabsorption could also be detected on the analgesic efficacy of tramadol (M. C. Frink et al, Arzneim.-Forsch/Drug Res. 46 (1996) 1029-1036; K. Flick et al, Arzneim.-Forsch/Drug Res. 28 (1978) 107-113). Despite this, according to current understanding the effect of M1 on the μ subtype of the opiate receptor is crucially responsible for the analgesic efficacy. The interaction of M1 with this receptor is comparable with that of morphine, i.e. in addition to the basic nitrogen atom, the phenolic OH group, which is methylated in codeine and tramadol, is crucial for binding to and activating the μ-opiate receptor which ultimately leads to analgesic effects.

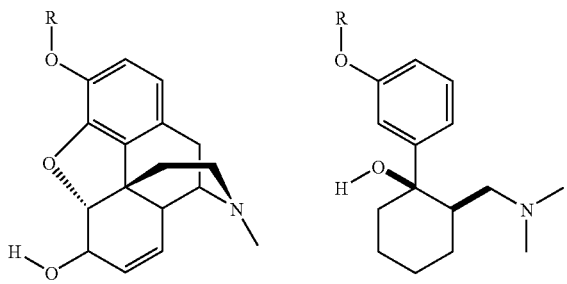

Codeine (R = CH₃)
Morphine (R = H)
Tramadol (R = CH₃)
M1 (R = H)

In the mid 1990s it was found that a substituent in the 4-position of the cyclohexane ring of tramadol intensifies the analgesic efficacy. This applies not only to the 3-phenols but also to 3-thiophenols and prodrugs (I. Graudums et al, DE 19547766, Grünenthal GmbH, 1995).

Compounds according to formula I are accordingly not part of this invention if
A is hydrogen,
$R^1$ is a phenyl ring, O- or S-substituted singly in the 3-position, and
$R^2$ and $R^3$ are both methyl and
partial formula Ia has the following meaning:

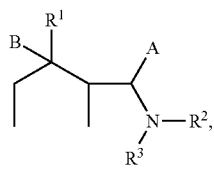

in other words X represents

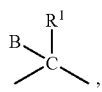

and B represents OH
and at the same time the grouping

is

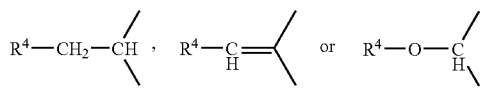

wherein $R^4$ is $C_{1-6}$ alkyl, $C_{2-6}$ alkenyl, $C_{5-7}$ cycloalkylmethyl, or substituted or unsubstituted phenyl or substituted or unsubstituted benzyl.

The compounds listed above are already known from DE 195 47 766 A1 (Graudums et al). However, as can be seen in formula I shown there, Grandums et al. assumed that, in principle, a phenyl ring O- or S-substituted singly in the 3-position is required for the analgesic effect, in particular for the μ-bond. This also coincides with the prevailing teaching as can be inferred, for example, from Chen, Z. R.; Irvine, R. J.; Somogyi, A. A.; Bochner, F. Life Sci. 1991, 48, 2165-2171.

It has surprisingly now been found in this invention that a phenyl ring O- or S-substituted singly in the 3 position is not a prerequisite for the p-bond and in particular analgesia.

Accordingly, this invention preferably relates to substituted C-cyclohexylmethylamine derivatives of formula I, in which $R^1$ is not a phenyl ring O- or S-substituted singly in the 3-position.

Also accordingly preferred are substituted C-cyclohexylmethylamine derivatives according to formula I, in which $R^1$ is saturated or unsaturated, branched or unbranched, singly or multiply substituted or unsubstituted $C_{1-10}$ alkyl or $C_{3-10}$ cycloalkyl, preferably $C_{1-6}$ alkyl or $C_{3-6}$ cycloalkyl; naphthyl, heteroaryl, aryl bound by saturated or unsaturated $C_{1-3}$ alkyl or $C_{1-3}$ alkylene or ethinyl; or $C_{3-10}$ cycloalkyl, preferably $C_{3-6}$ cycloalkyl bound by saturated or unsaturated $C_{1-3}$ alkyl or $C_{1-3}$ alkylene or ethinyl or heteroaryl bound by saturated or unsaturated $C_{1-3}$ alkyl or $C_{1-3}$ alkylene or ethinyl, respectively unsubstituted or singly or multiply substituted by radicals selected independently of one another from F, Cl, Br, I, $OR^{18}$, $SR^{18}$, $SO_2R^{18}$, $SO_2OR^{18}$, CN, $COOR^{18}$, $NR^{19}R^{20}$;

unsubstituted or singly or multiply substituted $C_{1-10}$ alkyl, $C_{3-10}$ cycloalkyl preferably $C_{1-6}$ alkyl or $C_{3-6}$ cycloalkyl or silyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl, preferably $C_{3-6}$ cycloalkyl or heteroaryl;

or $R^1$ corresponds to a compound according to formula II

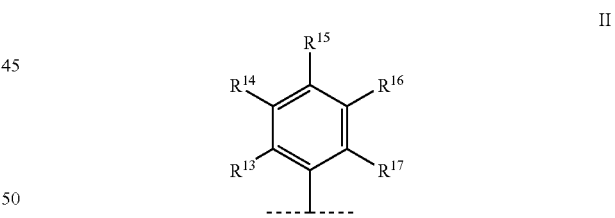

II wherein
$R^{13}$, $R^{15}$ and $R^{17}$, independent of one another, are H, F, Cl, Br, I, $OR^{18}$, $SR^{18}$, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl, preferably $C_{1-6}$ alkyl or $C_{3-6}$ cycloalkyl or silyl; respectively singly or multiply substituted or unsubstituted aryl or heteroaryl; respectively singly or multiply substituted aryl bound by saturated or unsaturated $C_{1-3}$ alkyl or $C_{1-3}$ alkylene or ethinyl, $C_{3-10}$ cycloalkyl, preferably $C_{3-6}$ cycloalkyl or heteroaryl;

$R^{14}$ and $R^{16}$, independent of one another, are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl, preferably $C_{1-6}$ alkyl or $C_{3-6}$ cycloalkyl or silyl; respectively singly or multiply substituted or unsubstituted aryl or heteroaryl; respectively singly or multiply substituted or unsubstituted aryl bound by saturated or unsaturated $C_{1-3}$ alkyl or $C_{1-3}$ alkylene or ethinyl, $C_{1-10}$ cycloalkyl, preferably $C_{3-6}$ cycloalkyl or heteroaryl;

or $R^{13}$ and $R^{14}$, or $R^{14}$ and $R^{15}$ together respectively form the group $OCH_2O$, $OCH_2CH_2O$, $CH=CHO$, $CH=C(CH_3)O$ or $CH=CHNH$, and $R^{15}$—$R^{17}$, or $R^{13}$, $R^{16}$ and $R^{17}$ have the meaning given above, wherein $R^{18}$ is H, respectively saturated or unsaturated, branched or unbranched, unsubstituted or singly or multiply substituted $C_{1-10}$ alkyl or $C_{3-10}$ cycloalkyl, preferably $C_{1-6}$ alkyl or $C_{3-6}$ cycloalkyl; unsubstituted or singly or multiply substituted aryl or heteroaryl; or aryl, $C_{3-10}$ cycloalkyl, preferably $C_{3-6}$ cycloalkyl or heteroaryl; bound by saturated or unsaturated $C_{1-3}$ alkyl or $C_{1-3}$ alkylene, respectively unsubstituted or singly or multiply substituted;

$R^{19}$ and $R^{20}$, independent of one another, are H, respectively saturated or unsaturated, branched or unbranched, unsubstituted or singly or multiply substituted $C_{1-10}$ alkyl or $C_{3-10}$ cycloalkyl, preferably $C_{1-6}$ alkyl or $C_{3-6}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl, preferably $C_{3-6}$ cycloalkyl or heteroaryl;

or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H, saturated or unsaturated, branched or unbranched, unsubstituted or singly or multiply substituted $C_{1-10}$ alkyl, preferably $C_{1-6}$ alkyl.

It was also assumed in DE 195 47 766 A1 (Graudums et al) that cyclohexanol is required for an analgesic effect. Surprisingly, however, this is not necessary, as the analgesic data of a series of compounds according to the invention show. Therefore, substituted C-cyclohexylmethylamine derivatives according to the invention are also preferred in which partial formula Ia is:

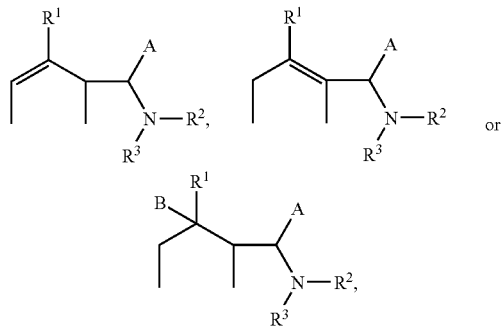

wherein B is $OR^7$, H, F, Cl or $NR^8R^9$, wherein $R^7$ is respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

$R^8$ and $R^9$, independent of one another, are H; respectively saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

or $R^8$ and $R^9$ together form $CH_2CH_2OCH_2CH_2$, $CH_2CH_2NR^{10}CH_2CH_2$ or $(CH_2)_{3-6}$, wherein $R^{10}$ is H; respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl, Surprisingly, substances according to the invention in which A is aryl or heteroaryl, singly or multiply substituted or unsubstituted respectively, exhibit a higher affinity with the α receptor than the compounds known, for example from DE 195 47 766 A1, where $R^1$ is a phenyl ring O- or S-substituted in the 3-position. Therefore, the compounds according to the present invention provide the possibility of reducing or completely avoiding side effects accompanying the binding to the μ-receptor.

However, the analgesic effect is obviously also a decisive criterion in this case, in particular in vivo.

A further preferred subject is C-cyclohexylmethylamine derivatives substituted according to the invention in which A is hydrogen. These are also new analgesics.

Compounds according to formula I are not a part of this invention if $R^2$, $R^3$, independent of one another, are H, branched or unbranched, singly or multiply substituted or unsubstituted, saturated or unsaturated $C_1$-$C_{10}$ alkyl; saturated or unsaturated, singly or multiply substituted or unsubstituted $C_3$-$C_7$ cycloalkyl or a corresponding heterocycle, in which a carbon atom is replaced by N, S or O in the ring; saturated or unsaturated, singly or multiply substituted or unsubstituted alkylaryl or alkylheteroaryl; respectively singly or multiply substituted or unsubstituted aryl or heteroaryl;

or $R^2$ and $R^3$ together form a ring and represent $CH_2CH_2OCH_2CH_2$, $CH_2CH_2NR^6CH_2CH_2$ or $(CH_2)_{3-6}$;

X has the meaning that makes partial formula Ia to be:

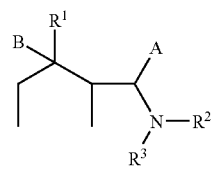

in other words X represents,

A is hydrogen, $R^1$ is an unsubstituted or singly or doubly substituted phenyl ring, B is H, F, Cl, OH or $OR^7$, wherein $R^7$ is
branched or unbranched, singly or multiply substituted or unsubstituted, saturated or unsaturated $C_1$-$C_{10}$ alkyl; singly or multiply substituted or unsubstituted saturated or unsaturated $C_3$-$C_7$ cycloalkyl or a corresponding heterocycle, in which a carbon atom is replaced in the ring by N, S or O; saturated or unsaturated, singly or multiply substituted or unsubstituted alkylaryl or alkylheteroaryl; respectively singly or multiply substituted or unsubstituted aryl or heteroaryl;

and at the same time the group

represents

wherein V is $OR^4$ wherein $R^4$ is $COR^5$ and wherein $R^5$ is unsubstituted or singly or multiply substituted $C_{1-6}$ alkyl.

Compounds of this type are described in WO01/57232 A1 and are also found to some extent in Gais H. J., Griebel C. and Buschmann H., Tetrahedron: Asymmetry 11, 917-928 (2000).

According to the invention, it is preferred that $R^1$ is:
respectively saturated or unsaturated, branched or unbranched, singly or multiply substituted or unsubstituted $C_{1-10}$ alkyl or $C_{3-10}$ cycloalkyl, preferably $C_{1-6}$ alkyl or $C_{3-6}$ cycloalkyl; respectively unsubstituted or singly or multiply substituted naphthyl, heteroaryl, $C_{3-10}$ cycloalkyl, preferably $C_{3-6}$ cycloalkyl bound by saturated or unsaturated $C_{1-3}$ alkyl or $C_{1-3}$ alkylene or ethinyl or heteroaryl bound by saturated or unsaturated $C_{1-3}$ alkyl or $C_{1-3}$ alkylene or ethinyl;
and is substituted with radicals selected independently of one another from the group consisting of:
F, Cl, Br, I, $OR^{18}$, $SR^{18}$, $SO_2R^{18}$, $SO_2OR^{18}$, CN, $COOR^{18}$, $NR^{19}R^{20}$;
unsubstituted or singly or multiply substituted $C_{1-10}$ alkyl, $C_{1-10}$ cycloalkyl, preferably $C_{1-6}$ alkyl or $C_{3-6}$ cycloalkyl or silyl; unsubstituted or singly or multiply substituted aryl or heteroaryl; and respectively unsubstituted or singly or multiply substituted aryl bound by saturated or unsaturated $C_{1-3}$ alkyl or $C_{1-3}$ alkylene, $C_{3-10}$ cycloalkyl, preferably $C_{3-6}$ cycloalkyl or heteroaryl.

It is also preferred that, in C-cyclohexylmethylamine derivatives substituted according to the invention, $R^1$ corresponds to a compound according to formula II

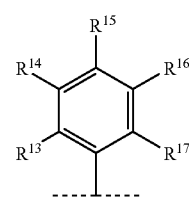

II wherein
$R^{13}$, $R^{15}$ and $R^{17}$, independent of one another, are H, F, Cl, Br, I, $OR^{18}$, $SR^{18}$, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl, preferably $C_{1-6}$ alkyl or $C_{3-6}$ cycloalkyl or silyl; respectively singly or multiply substituted or unsubstituted aryl or heteroaryl; respectively singly or multiply substituted or unsubstituted aryl bound by saturated or unsaturated $C_{1-3}$ alkyl or $C_{1-3}$ alkylene or ethinyl, $C_{3-10}$ cycloalkyl, preferably $C_{3-6}$ cycloalkyl or heteroaryl;
$R^{14}$ and $R^{16}$, independent of one another, are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl, preferably $C_{1-6}$ alkyl or $C_{3-6}$ cycloalkyl or silyl; respectively singly or multiply substituted or unsubstituted aryl or heteroaryl; respectively singly or multiply substituted or unsubstituted aryl bound by saturated or unsaturated $C_{1-3}$ alkyl or $C_{1-3}$ alkylene or ethinyl, $C_{3-10}$ cycloalkyl, preferably $C_{3-6}$ cycloalkyl or heteroaryl;
or $R^{13}$ and $R^{14}$ or $R^{14}$ and $R^{15}$ together respectively form the group $OCH_2O$, $OCH_2CH_2O$, CH=CHO, CH=C($CH_3$)O or CH=CHNH and $R^{15}$—$R^{17}$ or $R^{13}$, and $R^{16}$ and $R^{17}$ have the meaning given above,
wherein $R^{18}$ is H; respectively saturated or unsaturated, branched or unbranched, unsubstituted or singly or multiply substituted $C_{1-10}$ alkyl or $C_{3-10}$ cycloalkyl, preferably $C_{1-6}$ alkyl or $C_{3-6}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl, preferably $C_{3-6}$ cycloalkyl or heteroaryl;
$R^{19}$ and $R^{20}$, independent of one another, are H, respectively saturated or unsaturated, branched or unbranched, unsubstituted or singly or multiply substituted $C_{1-10}$ alkyl or $C_{3-10}$ cycloalkyl, preferably $C_{1-6}$ alkyl or $C_{3-6}$ cycloalkyl; respectively unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl, preferably $C_{3-6}$ cycloalkyl or heteroaryl;
or $R^{19}$ and $R^{20}$ together form $CH_2CH_2OCH_2CH_2$, $CH_2CH_2NR^{21}CH_2CH_2$ or $(CH_2)_{3-6}$,
wherein $R^{21}$ is H, $C_{1-10}$ alkyl, preferably saturated or unsaturated, branched or unbranched, unsubstituted or singly or multiply substituted $C_{1-6}$ alkyl, and

is:

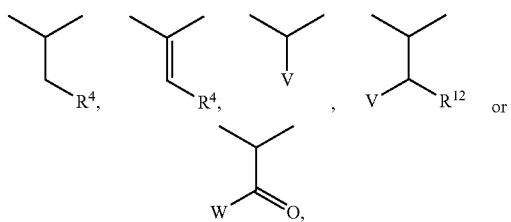

wherein R⁴ is H, COR⁵ᵃ, SO₂R⁵; respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl, wherein R⁵ is respectively saturated or unsaturated, branched or unbranched, singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl, wherein R⁵ᵃ is saturated or unsaturated, branched or unbranched, singly or multiply substituted or unsubstituted $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl, wherein V is OR⁴ or NR⁴R¹¹, wherein W is R¹¹, OR¹² or NR¹¹R¹², wherein R¹¹ and R¹², independent of one another, are H; respectively saturated or unsaturated, branched or unbranched, singly or multiply substituted or unsubstituted $C_{7-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl.

C-cyclohexylmethylamine derivatives substituted according to the invention are also particularly preferred, in which
R² and R³, independent of one another, are H; saturated or unsaturated, branched or unbranched, singly or multiply substituted or unsubstituted $C_{1-6}$ alkyl or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl, or the radicals R² and R³ together form $CH_2CH_2OCH_2CH_2$, $CH_2CH_2NR^6CH_2CH_2$ or $(CH_2)_{3-6}$, wherein R⁶ is H; respectively saturated or unsaturated, branched or unbranched, singly or multiply substituted or unsubstituted $C_{1-6}$ alkyl, in particular CH₃, or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl;

and/or

R⁷ is respectively saturated or unsaturated, branched or unbranched singly or multiply substituted or unsubstituted $C_{1-6}$ alkyl, or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl;

and/or

R⁸ and R⁹, independent of one another, are H; respectively saturated or unsaturated, branched or unbranched, singly or multiply substituted or unsubstituted $C_{1-6}$ alkyl or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl; or R² and R³ together form $CH_2CH_2OCH_2CH_2$, $CH_2CH_2NR^{10}CH_2CH_2$ or $(CH_2)_{3-6}$, wherein R¹⁰ is H; respectively saturated or unsaturated, branched or unbranched singly or multiply substituted or unsubstituted $C_{1-6}$ alkyl or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl, and/or R⁴ is H, COR⁵, SO₂R⁵; respectively saturated or unsaturated, branched or unbranched singly or multiply substituted or unsubstituted $C_{1-6}$ alkyl or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl, wherein R⁵ is singly or multiply substituted or unsubstituted $C_{1-6}$ alkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, or heteroaryl, and/or R¹¹ and R¹², independent of one another, are H; respectively saturated or unsaturated, branched or unbranched singly or multiply substituted or unsubstituted $C_{1-6}$ alkyl or $C_{3-6}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-6}$ cycloalkyl or heteroaryl;

and/or

R¹³, R¹⁵ and R¹⁷, independent of one another, are H, F, Cl, Br, I, OR¹⁸, SR¹⁸, SO₂R¹⁸, SO₂OR¹⁸, CN, COOR¹⁸, NR¹⁹R²⁰; saturated or unsaturated, branched or unbranched, singly or multiply substituted or unsubstituted $C_{1-6}$ alkyl, $C_{3-6}$ cycloalkyl or silyl; singly or multiply substituted or unsubstituted aryl or heteroaryl; respectively singly or multiply substituted or unsubstituted aryl bound by saturated or unsaturated $C_{1-3}$ alkyl or $C_{1-3}$ alkylene or ethinyl, $C_{3-6}$ cycloalkyl or heteroaryl;

and/or $R^{14}$ and $R^{16}$, independent of one another, are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-6}$ alkyl, $C_{3-6}$ cycloalkyl or silyl; respectively singly or multiply substituted or unsubstituted aryl or heteroaryl; respectively singly or multiply substituted or unsubstituted aryl bound by saturated or unsaturated $C_{1-3}$ alkyl or $C_{1-3}$ alkylene or ethinyl, $C_{3-6}$ cycloalkyl or heteroaryl;

or the radicals $R^{13}$ and $R^{14}$ or $R^{14}$ and $R^{15}$ together respectively form the group $OCH_2O$, $OCH_2CH_2O$, $CH=CHO$, $CH=C(CH_3)O$ or $CH=CHNH$ and $R^{15}$— $R^{17}$ or $R^{13}$, $R^{16}$ and $R^{17}$ have the meaning given above, and/or $R^{18}$ is respectively saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene or ethinyl, $C_{3-6}$ cycloalkyl or heteroaryl;

and/or $R^{19}$ and $R^{20}$, independent of one another, are H; respectively saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-6}$ cycloalkyl or heteroaryl;

or $R^{19}$ and $R^{20}$ together form $CH_2CH_2OCH_2CH_2$, $CH_2CH_2NR^{10}CH_2CH_2$ or $(CH_2)_{3-6}$, and/or $R^{21}$ is H, saturated or unsaturated, branched or unbranched, unsubstituted or singly or multiply substituted $C_{1-6}$ alkyl.

C-cyclohexylmethylamine derivatives substituted according to the invention are also particularly preferred in which A is Hydrogen or phenyl, unsubstituted or singly or multiply substituted; preferably hydrogen.

Substituted C-cyclohexylmethylamine derivatives according to the invention are also preferred, in which R2 and R3 are saturated or unsaturated, branched or unbranched or singly or multiply substituted $C_{1-6}$ alkyl, preferably $CH_3$, in particular both are $CH_3$, or $R^2$ and $R^3$ together represent $CH_2CH_2NR^{10}CH_2CH_2$ or $(CH_2)_{3-6}$, wherein $R^6$ is H or saturated, branched or unbranched, and unsubstituted $C_{1-6}$ alkyl; in particular H or $CH_3$.

Substituted C-cyclohexylmethylamine derivatives according to the invention are a preferred embodiment of the invention, in which $R^1$ is saturated or unsaturated, branched or unbranched $C_{1-6}$ alkyl; $C_{3-6}$ cycloalkyl, naphthyl, phenyl, furyl, thiophenyl, naphthyl bound by $C_{1-3}$ alkylene or ethinyl, phenyl, $C_{3-6}$ cycloalkyl or thiophenyl bound by $C_{1-3}$ alkyl or $C_{1-3}$ alkylene or ethinyl or furyl, which can be unsubstituted or singly or multiply unsubstituted.

Substituted C-cyclohexylmethylamine derivatives according to the invention are also preferred, in which

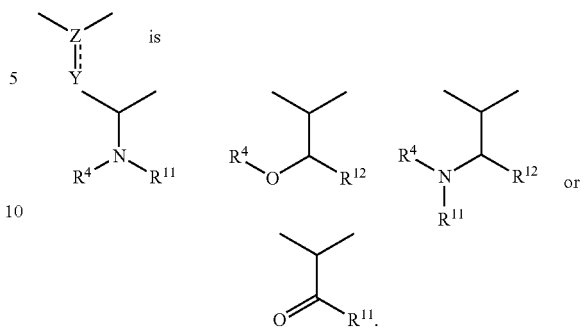

is

The invention particularly preferably relates to substituted C-cyclohexylmethylamine derivatives of formula I, wherein A is H; respectively singly or multiply substituted or unsubstituted aryl or heteroaryl;

$R^1$ is naphthyl or naphthyl bound by saturated or unsaturated $C_{1-3}$ alkyl or $C_{1-3}$ alkylene or ethinyl, respectively unsubstituted or singly or multiply substituted by radicals selected independently of one another from the group consisting of F, Cl, Br, I, $OR^{18}$, $SR^{18}$, $SO_2R^{18}$, $SO_2OR^{18}$, CN, $COOR^{18}$, and $NR^{19}R^{20}$; unsubstituted or singly or multiply substituted $C_{1-10}$ alkyl, $C_{3-10}$ cycloalkyl or silyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

wherein $R^{18}$ is H; respectively saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

$R^{19}$ and $R^{20}$, independent of one another, are H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or respectively unsubstituted or singly or multiply substituted aryl bound by saturated or unsaturated $C_{1-3}$ alkyl or $C_{1-3}$ alkylene, $C_{3-10}$ cycloalkyl or heteroaryl;

or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H; saturated or unsaturated, branched or unbranched, unsubstituted or singly or multiply substituted $C_{1-10}$ alkyl;

$R^2$ and $R^3$, independent of one another, are H; respectively saturated or unsaturated, branched or unbranched singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

or $R^2$ and $R^3$ together represent $CH_2CH_2OCH_2CH_2$, $CH_2CH_2NR^6CH_2CH_2$ or $(CH_2)_{3-6}$, wherein $R^6$ is H; respectively saturated or unsaturated, branched or unbranched singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

partial formula Ia is:

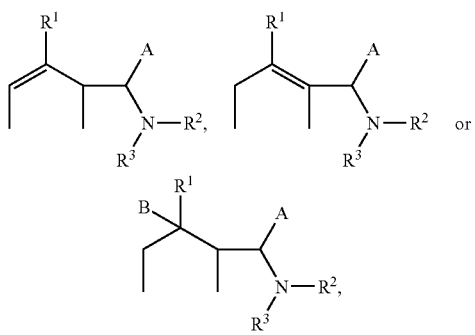

wherein B is OH, $OR^7$, H, F, Cl or $NR^8R^9$, wherein $R^7$ is respectively saturated or unsaturated, branched or unbranched singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

$R^8$ and $R^9$, independent of one another, are H; respectively saturated or unsaturated, branched or unbranched singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

or $R^8$ and $R^9$ together form $CH_2CH_2OCH_2CH_2$, $CH_2CH_2NR^{10}CH_2CH_2$ or $(CH_2)_{3-6}$, wherein $R^{10}$ is H; respectively saturated or unsaturated, branched or unbranched singly or multiply substituted or unsubstituted $C_{1-10}$ alkyl or $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl;

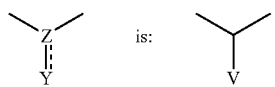

wherein V is $OR^4$, wherein $R^4$ is $COR^5$; respectively saturated or unsaturated, branched or unbranched singly or multiply substituted or unsubstituted $C_{1-10}$ alkyl; saturated or unsaturated, singly or multiply substituted or unsubstituted $C_{3-10}$ cycloalkyl; respectively singly or multiply substituted or unsubstituted aryl or heteroaryl; or respectively singly or multiply substituted or unsubstituted aryl bound by $C_{1-3}$ alkyl, $C_{3-10}$ cycloalkyl or heteroaryl, wherein $R^5$ is saturated or unsaturated, branched or unbranched, singly or multiply substituted or unsubstituted $C_{1-10}$ alkyl; saturated or unsaturated, singly or multiply substituted or unsubstituted $C_{3-10}$ cycloalkyl; respectively singly or multiply substituted or unsubstituted aryl or heteroaryl; or respectively singly or multiply substituted or unsubstituted aryl bound by saturated or unsaturated $C_{1-3}$ alkyl or $C_{1-3}$ alkylene, $C_{3-10}$ cycloalkyl or heteroaryl, optionally in the form of their racemates, their pure stereoisomers, in particular enantiomers or diastereomers, or in the form of blends of stereoisomers, in particular the enantiomers or diastereomers, in any mixing ratio; in the illustrated form or in the form of their acids or their bases or in the form of their salts, in particular the physiologically acceptable salts, or in the form of their solvates, in particular the hydrates.

With respect to these particularly preferred substituted C-cyclohexylmethylamine derivatives, in the preferred embodiment A is H or respectively singly or multiply substituted or unsubstituted phenyl; preferably H and/or $R^1$ is naphthyl, unsubstituted or singly or multiply substituted by radicals selected independently of one another from the group consisting of F, Cl, Br, I, $OR^{18}$; and branched or unbranched, unsubstituted or singly or multiply substituted $C_{1-4}$ alkyl;

wherein $R^{18}$ is H; branched or unbranched, unsubstituted or singly or multiply substituted $C_{1-4}$ alkyl;

$R^1$ is preferably naphthyl, unsubstituted or substituted by OH or $OCH_3$, and/or $R^2$ and $R^3$ are saturated or unsaturated, branched or unbranched, unsubstituted or singly or multiply substituted $C_{1-6}$ alkyl, preferably $CH_3$, in particular both are $CH_3$, or $R^2$ and $R^3$ together represent $CH_2CH_2NR^6CH_2CH_2$ or $(CH_2)_{4-5}$, in particular together represent $CH_2CH_2NR^6CH_2CH_2$, wherein $R^6$ is H or saturated, branched or unbranched, and unsubstituted $C_{1-6}$ alkyl; in particular H or $CH_3$;

and/or partial formula Ia is:

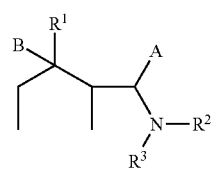

in other words X represents

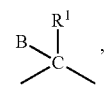

and wherein

B is OH, OR$^7$, H, F, Cl, wherein R$^7$ is branched or unbranched, singly or multiply substituted or unsubstituted C$_{1-4}$ alkyl;
preferably wherein B is OH, and/or

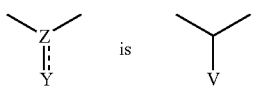

wherein V is OR$^4$,
  wherein R$^4$ is COR$^5$; singly or multiply substituted or unsubstituted phenyl or benzyl;
  in particular COR$^5$ or singly or multiply substituted or unsubstituted or benzyl;
  wherein R$^5$ is saturated or unsaturated, branched or unbranched, singly or multiply substituted or unsubstituted C$_{1-10}$ alkyl, in particular C$_{1-6}$ alkyl; or singly or multiply substituted or unsubstituted phenyl.

Further particularly preferred compounds according to the invention are the group consisting of:
  4-benzyloxy-1-(4-bromophenyl)-2-dimethylaminomethyl-cyclohexanol;
  4-benzyloxy-2-dimethylaminomethyl-1-(4-trifluoromethyl-phenyl)-cyclohexanol;
  4-benzyloxy-1-(3,4-difluorophenyl)-2-dimethylaminomethyl-cyclohexanol;
  4-benzyloxy-2-dimethylaminomethyl-1-(3-fluoro-4-methyl-phenyl)-cyclohexanol;
  4-benzyloxy-1-(3,4-dichlorophenyl)-2-dimethylaminomethyl-cyclohexanol;
  4-benzyloxy-2-dimethylaminomethyl-1-naphthalen-2-yl-cyclohexanol;
  4-benzyloxy-2-dimethylaminomethyl-1-(3,4-dimethyl-phenyl)-cyclohexanol;
  4-benzyloxy-2-dimethylaminomethyl-1-(4-fluoro-3-methyl-phenyl)-cyclohexanol;
  4-benzyloxy-2-dimethylaminomethyl-1-(5-fluoro-2-methyl-phenyl)-cyclohexanol;
  4-benzyloxy-1-(3-chloro-4-fluorophenyl)-2-dimethylaminomethyl-cyclohexanol;
  4-benzyloxy-1-(5-chloro-2-methoxy-phenyl)-2-dimethylaminomethylcyclohexanol;
  4-benzyloxy-1-(2-bromophenyl)-2-dimethylaminomethyl-cyclohexanol;
  4-benzyloxy-2-dimethylaminomethyl-1-(2-methoxy-phenyl)-cyclohexanol;
  4-benzyloxy-2-dimethylaminomethyl-1-(2-methylsulfanyl-phenyl)-cyclohexanol;
  4-benzyloxy-1-(4-chlorophenyl)-2-dimethylaminomethyl-cyclohexanol;
  4-benzyloxy-1-(3-bromophenyl)-2-dimethylaminomethyl-cyclohexanol;
  4-benzyloxy-1-(4-bromo-3-fluorophenyl)-2-dimethylaminomethyl-cyclohexanol;
  4-benzyloxy-2-dimethylaminomethyl-1-(4-methoxy-phenyl)-cyclohexanol;
  4-benzyloxy-1-(2-chlorophenyl)-2-dimethylaminomethyl-cyclohexanol;
  4-benzyloxy-2-dimethylaminomethyl-1-(3-trifluoromethyl-phenyl)-cyclohexanol;
  4-benzyloxy-2-dimethylaminomethyl-1-(4-pentyl-phenyl)-cyclohexanol;
  4-benzyloxy-2-dimethylaminomethyl-1-(2,5-dimethyl-phenyl)-cyclohexanol;
  4-benzyloxy-2-dimethylaminomethyl-1-(4-isopropyl-phenyl)-cyclohexanol;
  4-benzyloxy-2-dimethylaminomethyl-1-(2,3-dimethyl-phenyl)-cyclohexanol;
  4-benzyloxy-2-dimethylaminomethyl-1-(3-fluorophenyl)-cyclohexanol;
  4-benzyloxy-1-(3,5-bis-trifluoromethyl-phenyl)-2-dimethylaminomethylcyclohexanol;
  4-benzyloxy-2-dimethylaminomethyl-1-(4-ethyl-phenyl)-cyclohexanol;
  4-benzyloxy-1-(3,5-dichlorophenyl)-2-dimethylaminomethyl-cyclohexanol;
  2-dimethylaminomethyl-4-(4-fluorobenzyloxy)-1-o-tolyl-cyclohexanol;
  2-dimethylaminomethyl-4-(4-fluorobenzyloxy)-1-p-tolyl-cyclohexanol;
  2-dimethylaminomethyl-1-(2,5-dimethyl-phenyl)-4-(4-fluorobenzyloxy)-cyclohexanol;
  2-dimethylaminomethyl-1-(3,4-dimethyl-phenyl)-4-(4-fluorobenzyloxy)-cyclohexanol;
  2-dimethylaminomethyl-1-(3,5-dimethyl-phenyl)-4-(4-fluorobenzyloxy)-cyclohexanol;
  2-dimethylaminomethyl-4-(4-fluorobenzyloxy)-1-(4-isopropyl-phenyl)-cyclohexanol;
  2-dimethylaminomethyl-4-(4-fluorobenzyloxy)-1-(3-fluorophenyl)-cyclohexanol;
  2-dimethylaminomethyl-4-(4-fluorobenzyloxy)-1-(4-fluorophenyl)-cyclohexanol;
  1-(3,4-difluorophenyl)-2-dimethylaminomethyl-4-(4-fluorobenzyloxy)-cyclohexanol;
  2-dimethylaminomethyl-4-(4-fluorobenzyloxy)-1-(3-fluoro-4-methyl-phenyl)-cyclohexanol;
  2-dimethylaminomethyl-4-(4-fluorobenzyloxy)-1-(4-fluoro-3-methyl-phenyl)-cyclohexanol;
  1-(2-chlorophenyl)-2-dimethylaminomethyl-4-(4-fluorobenzyloxy)-cyclohexanol;
  1-(3-chlorophenyl)-2-dimethylaminomethyl-4-(4-fluorobenzyloxy)-cyclohexanol;
  1-(4-chlorophenyl)-2-dimethylaminomethyl-4-(4-fluorobenzyloxy)-cyclohexanol;
  1-(3,4-dichlorophenyl)-2-dimethylaminomethyl-4-(4-fluorobenzyloxy)-cyclohexanol;
  1-(4-chloro-3-fluorophenyl)-2-dimethylaminomethyl-4-(4-fluorobenzyloxy)-cyclohexanol;
  1-(3,5-dichlorophenyl)-2-dimethylaminomethyl-4-(4-fluorobenzyloxy)-cyclohexanol;
  1-(4-chloro-2-methoxy-phenyl)-2-dimethylaminomethyl-4-(4-fluorobenzyloxy)-cyclohexanol;
  2-dimethylaminomethyl-4-(4-fluorobenzyloxy)-1-(4-trifluoromethyl-phenyl)-cyclohexanol;
  1-(3,5-bis-trifluoromethyl-phenyl)-2-dimethylaminomethyl-4-(4-fluorobenzyloxy)-cyclohexanol;
  2-dimethylaminomethyl-4-(4-fluorobenzyloxy)-1-(2-methoxy-phenyl)-cyclohexanol;
  2-dimethylaminomethyl-4-(4-fluorobenzyloxy)-1-(2-methylsulfanyl-phenyl)-cyclohexanol;
  (5-benzyloxy-2-thiophen-2-yl-cyclohex-2-enylmethyl)-dimethyl-amine;
  [5-(4-fluorobenzyloxy)-2-thiophen-2-yl-cyclohex-2-enylmethyl]-dimethyl-amine;
  3,4-dichloro-N-[3-dimethylaminomethyl-4-hydroxy-4-(3-methoxy-phenyl)-cyclohexyl]-benzamide;
  naphthalene-2-carboxylic acid [3-dimethylaminomethyl-4-hydroxy-4-(3-methoxy phenyl)-cyclohexyl]-amide;

N-[3-dimethylaminomethyl-4-hydroxy-4-(3-methoxy-phenyl)-cyclohexyl]-3-phenyl-propionamide;
N-[3-dimethylaminomethyl-4-hydroxy-4-(3-methoxy-phenyl)-cyclohexyl]-4-nitro-benzamide;
N-[3-dimethylaminomethyl-4-hydroxy-4-(3-methoxy-phenyl)-cyclohexyl]-4-methyl-3-nitro-benzamide;
N-[3-dimethylaminomethyl-4-hydroxy-4-(3-methoxy-phenyl)-cyclohexyl]-3,4,5-trimethoxy-benzamide;
2-(4-chlorophenoxy)-N-[3-dimethylaminomethyl-4-hydroxy-4-(3-methoxy-phenyl)-cyclohexyl]-acetamide;
N-[3-dimethylaminomethyl-4-hydroxy-4-(3-methoxy-phenyl)-cyclohexyl]-3-nitro-benzamide;
furan-2-carboxylic acid [3-dimethylaminomethyl-4-hydroxy-4-(3-methoxy-phenyl)-cyclohexyl]-amide;
N-[3-dimethylaminomethyl-4-hydroxy-4-(3-methoxy-phenyl)-cyclohexyl]-2-phenoxy-acetamide;
N-[3-dimethylaminomethyl-4-hydroxy-4-(3-methoxy-phenyl)-cyclohexyl]-4-trifluoromethyl-benzamide;
N-[3-dimethylaminomethyl-4-hydroxy-4-(3-methoxy-phenyl)-cyclohexyl]-4-methoxy-benzamide;
2-dimethylaminomethyl-1-(4-fluorophenyl)-4-phenethyl-cyclohexanol;
1-(4-bromophenyl)-2-dimethylaminomethyl-4-phenethyl-cyclohexanol;
2-dimethylaminomethyl-1-(4-ethyl-phenyl)-4-phenethyl-cyclohexanol;
2-dimethylaminomethyl-1-(4-isopropyl-phenyl)-4-phenethyl-cyclohexanol;
2-dimethylaminomethyl-1-(4-methoxy-phenyl)-4-phenethyl-cyclohexanol;
2-dimethylaminomethyl-1-(2,4-dimethyl-phenyl)-4-phenethyl-cyclohexanol;
2-dimethylaminomethyl-1-(2-methylsulfanyl-phenyl)-4-phenethyl-cyclohexanol;
2-dimethylaminomethyl-1-(5-fluoro-2-methyl-phenyl)-4-phenethyl-cyclohexanol;
2-dimethylaminomethyl-1-(2,5-dimethyl-phenyl)-4-phenethyl-cyclohexanol;
2-dimethylaminomethyl-4-phenethyl-1-p-tolyl-cyclohexanol;
2-dimethylaminomethyl-1-(3-fluorophenyl)-4-phenethyl-cyclohexanol;
1-(3-chlorophenyl)-2-dimethylaminomethyl-4-phenethyl-cyclohexanol;
1-(4-chloro-3-fluorophenyl)-2-dimethylaminomethyl-4-phenethyl-cyclohexanol;
2-dimethylaminomethyl-4-phenethyl-1-(3-trifluoromethyl-phenyl)-cyclohexanol;
1-(3,5-dichlorophenyl)-2-dimethylaminomethyl-4-phenethyl-cyclohexanol;
2-dimethylaminomethyl-1-(3,4-dimethyl-phenyl)-4-phenethyl-cyclohexanol;
1-(3,4-dichlorophenyl)-2-dimethylaminomethyl-4-phenethyl-cyclohexanol;
1-(4-chlorophenyl)-2-dimethylaminomethyl-4-phenethyl-cyclohexanol;
2-dimethylaminomethyl-1-(3-fluoro-4-methyl-phenyl)-4-phenethyl-cyclohexanol;
2-dimethylaminomethyl-1-(3,5-dimethyl-phenyl)-4-phenethyl-cyclohexanol;
1-(4-bromo-3-fluorophenyl)-2-dimethylaminomethyl-4-phenethyl-cyclohexanol;
1-(3,4-difluorophenyl)-2-dimethylaminomethyl-4-phenethyl-cyclohexanol;
2-dimethylaminomethyl-1-(2,3-dimethyl-phenyl)-4-phenethyl-cyclohexanol;
2-dimethylaminomethyl-1-naphthalen-1-yl-4-phenethyl-cyclohexanol;
1-(3,5-bis-trifluoromethyl-phenyl)-2-dimethylaminomethyl-4-phenethylcyclohexanol;
1-(3-bromophenyl)-2-dimethylaminomethyl-4-phenethyl-cyclohexanol;
2-dimethylaminomethyl-1-(4-fluoro-3-methyl-phenyl)-4-phenethyl-cyclohexanol;
2-dimethylaminomethyl-4-phenethyl-1-m-tolyl-cyclohexanol;
4-benzyl-2-dimethylaminomethyl-1-m-tolyl-cyclohexanol;
4-benzyl-1-(3,4-difluorophenyl)-2-dimethylaminomethyl-cyclohexanol;
4-benzyl-2-dimethylaminomethyl-1-p-tolyl-cyclohexanol;
2-dimethylaminomethyl-4-(3-methoxy-benzyl)-1-p-tolyl-cyclohexanol;
1-(4-chlorophenyl)-2-dimethylaminomethyl-4-(3-methoxy-benzyl)-cyclohexanol;
1-(4-bromo-3-fluorophenyl)-2-dimethylaminomethyl-4-(3-methoxy-benzyl)-cyclohexanol;
2-dimethylaminomethyl-4-(4-fluorobenzyl)-1-p-tolyl-cyclohexanol;
1-(4-chlorophenyl)-2-dimethylaminomethyl-4-(4-fluorobenzyl)-cyclohexanol;
dimethyl-[2-(5-methyl-thiophen-2-yl)-5-phenethyl-cyclohex-2-eny[methyl]amine;
[2-(3,5-bis-trifluoromethyl-phenyl)-5-phenethyl-cyclohex-1-enylmethyl]-dimethylamine;
dimethyl-(5-phenethyl-2-p-tolyl-cyclohex-1-enylmethyl)-amine;
[2-(3-chloro-4-fluorophenyl)-5-phenethyl-cyclohex-1-enylmethyl]-dimethyl-amine;
[2-(2,5-dimethyl-phenyl)-5-phenethyl-cyclohex-1-enylmethyl]-dimethyl-amine;
dimethyl-(5-phenethyl-2-p-tolyl-cyclohex-2-enylmethyl)-amine;
[2-(3,5-bis-trifluoromethyl-phenyl)-5-phenethyl-cyclohex-2-enylmethyl]-dimethyl-amine;
[2-(3-chloro-4-fluorophenyl)-5-phenethyl-cyclohex-2-enylmethyl]-dimethyl-amine;
[2-(3-chloro-4-fluorophenyl)-2-fluoro-5-phenethyl-cyclohexylmethyl]-dimethylamine;
[2-fluoro-5-(4-fluorobenzyl)-2-p-tolyl-cyclohexylmethyl]-dimethyl-amine;
benzyl-2-(dimethylamino-phenyl-methyl)-4-phenyl-cyclohexanol;
2-(dimethylamino-phenyl-methyl)-4-phenyl-1-vinyl-cyclohexanol;
1-(4-tert-butyl-phenyl)-2-(dimethylamino-phenyl-methyl)-4-phenylcyclohexanol;
2-(dimethylamino-phenyl-methyl)-4-phenyl-1-m-tolyl-cyclohexanol;
2-(dimethylamino-phenyl-methyl)-1-phenethyl-4-phenyl-cyclohexanol;
2-(dimethylamino-phenyl-methyl)-4-phenyl-1-phenylethynyl-cyclohexanol;
2-(dimethylamino-phenyl-methyl)-1-(3-methoxy-phenyl)-4-phenyl-cyclohexanol;
2-(dimethylamino-phenyl-methyl)-4-phenyl-1-(3-phenyl-propyl)-cyclohexanol;
2-(dimethylamino-phenyl-methyl)-1-(4-methoxy-phenyl)-4-phenyl-cyclohexanol;
2-(dimethylamino-phenyl-methyl)-1-(2-methoxy-phenyl)-4-phenyl-cyclohexanol;

4-benzyloxy-2-dimethylaminomethyl-1-phenyl-cyclohexanol;
1-benzyl-4-benzyloxy-2-dimethylaminomethyl-cyclohexanol;
4-benzyloxy-2-dimethylaminomethyl-1-(4-fluoro-3-methyl-phenyl)-cyclohexanol;
4-benzyloxy-2-dimethylaminomethyl-1-o-tolyl-cyclohexanol;
4-benzyloxy-2-dimethylaminomethyl-1-vinyl-cyclohexanol;
4-benzyloxy-1-cyclopentyl-2-dimethylaminomethyl-cyclohexanol;
4-benzyloxy-2-dimethylaminomethyl-1-m-tolyl-cyclohexanol;
4-benzyloxy-2-dimethylaminomethyl-bicyclohexyl-1-ol;
4-benzyloxy-2-dimethylaminomethyl-1-(4-fluorophenyl)-cyclohexanol;
4-benzyloxy-2-dimethylaminomethyl-1-phenylethynyl-cyclohexanol;
4-benzyloxy-2-dimethylaminomethyl-1-thiophen-2-yl-cyclohexanol;
4-benzyloxy-2-dimethylaminomethyl-1-(3-methoxy-phenyl)-cyclohexanol;
4-benzyloxy-2-dimethylaminomethyl-1-(3-phenyl-propyl)-cyclohexanol;
4-benzyloxy-2-dimethylaminomethyl-1-p-tolyl-cyclohexanol;
4-benzyloxy-2-dimethylaminomethyl-1-(4-methoxy-phenyl)-cyclohexanol;
4-benzyloxy-2-dimethylaminomethyl-1-(3-fluorophenyl)-cyclohexanol;
4-benzyloxy-1-(3-chlorophenyl)-2-dimethylaminomethyl-cyclohexanol;
4-benzyloxy-2-dimethylaminomethyl-1-(3-methoxy-benzyl)-cyclohexanol;
4-benzyloxy-1-(4-chloro-3-trifluoromethyl-phenyl)-2-dimethylaminomethyl-cyclohexanol;
4-benzyloxy-2-dimethylaminomethyl-1-(3-fluorobenzyl)-cyclohexanol;
4-benzyloxy-2-dimethylaminomethyl-1-(2-methyl-benzyl)-cyclohexanol;
4-benzyloxy-2-dimethylaminomethyl-1-(2,5-dimethylbenzyl)-cyclohexanol;
4-(4-chlorobenzyl)-2-dimethylaminomethyl-1-(3-methoxy-phenyl)-cyclohexanol;
4-(4-chlorobenzyl)-2-dimethylaminomethyl-1-(3-phenyl-propyl)-cyclohexanol;
4-(4-chlorobenzyl)-1-(2,3-dichlorophenyl)-2-dimethylaminomethyl-cyclohexanol;
4-(4-chlorobenzyl)-1-cyclohexylmethyl-2-dimethylaminomethyl-cyclohexanol;
4-(4-chlorobenzyl)-2-dimethylaminomethyl-1-(5-fluoro-2-methoxy-phenyl)-cyclohexanol;
4-(4-chlorobenzyl)-2-dimethylaminomethyl-1-(3-fluorophenyl)-cyclohexanol;
4-(4-chlorobenzyl)-1-(3-chlorophenyl)-2-dimethylaminomethyl-cyclohexanol;
4-(4-chlorobenzyl)-1-(3,5-dichlorophenyl)-2-dimethylaminomethyl-cyclohexanol;
4-(4-chlorobenzyl)-1-(2-chlorobenzyl)-2-dimethylaminomethyl-cyclohexanol;
4-(4-chlorobenzyl)-2-dimethylaminomethyl-1-(4-fluorobenzyl)-cyclohexanol;
4-(4-chlorobenzyl)-2-dimethylaminomethyl-1-(3-fluorobenzyl)-cyclohexanol;
4-(4-chlorobenzyl)-2-dimethylaminomethyl-1-(2-methoxy-phenyl)-cyclohexanol;
4-(4-chlorobenzyl)-2-dimethylaminomethyl-1-(2-methylbenzyl)-cyclohexanol;
4-(4-chlorobenzyl)-2-dimethylaminomethyl-1-(3-methylbenzyl)-cyclohexanol;
1,4-bis-(4-chlorobenzyl)-2-dimethylaminomethyl-cyclohexanol;
4-(4-chlorobenzyl)-1-(2-chloro-6-fluorobenzyl)-2-dimethylaminomethyl-cyclohexanol;
4-(4-chlorobenzyl)-2-dimethylaminomethyl-1-(2,5-dimethyl-benzyl)-cyclohexanol;
4-(4-chlorobenzyl)-1-(3-chlorobenzyl)-2-dimethylaminomethyl-cyclohexanol;
4-(4-chlorobenzyl)-1-(2,4-dichlorobenzyl)-2-dimethylaminomethyl-cyclohexanol;
4-(4-chlorobenzyl)-2-dimethylaminomethyl-1-phenyl-cyclohexanol;
4-(4-chlorobenzyl)-1-(4-chlorophenyl)-2-dimethylaminomethyl-cyclohexanol;
4-(4-chlorobenzyl)-2-dimethylaminomethyl-1-(4-fluoro-3-methyl-phenyl)-cyclohexanol;
4-(4-chlorobenzyl)-2-dimethylaminomethyl-1-o-tolyl-cyclohexanol;
4-(4-chlorobenzyl)-2-dimethylaminomethyl-1-vinyl-cyclohexanol;
4-(4-chlorobenzyl)-1-cyclopentyl-2-dimethylaminomethyl-cyclohexanol;
4-(4-chlorobenzyl)-2-dimethylaminomethyl-1-m-tolyl-cyclohexanol;
4-(4-chlorobenzyl)-2-dimethylaminomethyl-bicyclohexyl-1-ol;
4-(4-chlorobenzyl)-2-dimethylaminomethyl-1-(4-fluorophenyl)-cyclohexanol;
4-(4-chlorobenzyl)-2-dimethylaminomethyl-1-phenethyl-cyclohexanol;
4-(4-chlorobenzyl)-2-dimethylaminomethyl-1-phenylethynyl-cyclohexanol;
4-(4-chlorobenzyl)-2-dimethylaminomethyl-1-thiophen-2-yl-cyclohexanol;
4-(4-chlorobenzyl)-2-dimethylaminomethyl-1-p-tolyl-cyclohexanol;
4-(4-chlorobenzyl)-2-dimethylaminomethyl-1-(4-methoxy-phenyl)-cyclohexanol;
4-(4-chlorobenzyl)-2-dimethylaminomethyl-1-trimethylsilanylethynyl-cyclohexanol;
4-(4-chlorobenzyl)-1-(4-chloro-3-trifluoromethyl-phenyl)-2-dimethylaminomethyl-cyclohexanol;
4-(4-chlorobenzyl)-1-(3-chloro-4-fluorophenyl)-2-dimethylaminomethyl-cyclohexanol;
4-(4-chlorobenzyl)-2-dimethylaminomethyl-1-(3-trifluoromethyl-phenyl)-cyclohexanol;
2-dimethylaminomethyl-4-(4-fluorobenzyl)-1-phenyl-cyclohexanol; 0.1-(4-chlorophenyl)-2-dimethylaminomethyl-4-(4-fluorobenzyl)-cyclohexanol; 1-benzyl-2-dimethylaminomethyl-4-(4-fluorobenzyl)-cyclohexanol;
2-dimethylaminomethyl-4-(4-fluorobenzyl)-1-(4-fluoro-3-methyl-phenyl)-cyclohexanol;
2-dimethylaminomethyl-4-(4-fluorobenzyl)-1-o-tolyl-cyclohexanol;
2-dimethylaminomethyl-4-(4-fluorobenzyl)-1-vinyl-cyclohexanol;
1-(4-tert-butyl-phenyl)-2-dimethylaminomethyl-4-(4-fluorobenzyl)-cyclohexanol;
1-cyclopentyl-2-dimethylaminomethyl-4-(4-fluorobenzyl)-cyclohexanol;
2-dimethylaminomethyl-4-(4-fluorobenzyl)-1-m-tolyl-cyclohexanol;

2-dimethylaminomethyl-4-(4-fluorobenzyl)-bicyclo-hexyl-1-ol;
2-dimethylaminomethyl-4-(4-fluorobenzyl)-1-(4-fluorophenyl)-cyclohexanol;
2-dimethylaminomethyl-4-(4-fluorobenzyl)-1-phenethyl-cyclohexanol;
2-dimethylaminomethyl-4-(4-fluorobenzyl)-1-phenylethynyl-cyclohexanol;
2-dimethylaminomethyl-4-(4-fluorobenzyl)-1-thiophen-2-yl-cyclohexanol;
2-dimethylaminomethyl-4-(4-fluorobenzyl)-1-(3-methoxy-phenyl)-cyclohexanol;
2-dimethylaminomethyl-4-(4-fluorobenzyl)-1-(3-phenyl-propyl)-cyclohexanol;
1-(2,3-dichlorophenyl)-2-dimethylaminomethyl-4-(4-fluorobenzyl)-cyclohexanol;
2-dimethylaminomethyl-4-(4-fluorobenzyl)-1-p-tolyl-cyclohexanol;
2-dimethylaminomethyl-4-(4-fluorobenzyl)-1-(4-methoxy-phenyl)-cyclohexanol; 1-cyclohexylmethyl-2-dimethylaminomethyl-4-(4-fluorobenzyl)-cyclohexanol;
2-dimethylaminomethyl-4-(4-fluorobenzyl)-1-(5-fluoro2-methoxy-phenyl)-cyclohexanol;
2-dimethylaminomethyl-4-(4-fluorobenzyl)-1-(3-fluorophenyl)-cyclohexanol;
1-(3-chlorophenyl)-2-dimethylaminomethyl-4-(4-fluorobenzyl)-cyclohexanol;
1-(3,5-dichlorophenyl)-2-dimethylaminomethyl-4-(4-fluorobenzyl)-cyclohexanol;
1-(2-chlorobenzyl)-2-dimethylaminomethyl-4-(4-fluorobenzyl)-cyclohexanol;
2-dimethylaminomethyl-1,4-bis-(4-fluorobenzyl)-cyclohexanol;
2-dimethylaminomethyl-4-(4-fluorobenzyl)-1-(3-methoxy-benzyl)-cyclohexanol;
1-(4-chloro-3-trifluoromethyl-phenyl)-2-dimethylaminomethyl-4-(4-fluorobenzyl)-cyclohexanol;
2-dimethylaminomethyl-4-(4-fluorobenzyl)-1-(3-fluorobenzyl)-cyclohexanol;
2-dimethylaminomethyl-4-(4-fluorobenzyl)-1-(2-methoxy-phenyl)-cyclohexanol;
2-dimethylaminomethyl-4-(4-fluorobenzyl)-1-(2-methylbenzyl)-cyclohexanol;
1-(3-chloro-4-fluorophenyl)-2-dimethylaminomethyl-4-(4-fluorobenzyl)-cyclohexanol;
2-dimethylaminomethyl-4-(4-fluorobenzyl)-1-(3-trifluoromethyl-phenyl)-cyclohexanol;
2-dimethylaminomethyl-4-(4-fluorobenzyl)-1-(3-methylbenzyl)-cyclohexanol;
1-(4-chlorobenzyl)-2-dimethylaminomethyl-4-(4-fluorobenzyl)-cyclohexanol;
1-(2-chloro-6-fluorobenzyl)-2-dimethylaminomethyl-4-(4-fluorobenzyl)-cyclohexanol;
2-dimethylaminomethyl-1-(2,5-dimethyl-benzyl)-4-(4-fluorobenzyl)-cyclohexanol;
1-(3-chlorobenzyl)-2-dimethylaminomethyl-4-(4-fluorobenzyl)-cyclohexanol;
1-(2,4-dichlorobenzyl)-2-dimethylaminomethyl-4-(4-fluorobenzyl)-cyclohexanol;
2-dimethylaminomethyl-4-(3-methoxy-benzyl)-1-phenyl-cyclohexanol;
1-benzyl-2-dimethylaminomethyl-4-(3-methoxy-benzyl)-cyclohexanol;
2-dimethylaminomethyl-1-(4-fluoro-3-methyl-phenyl)-4-(3-methoxy-benzyl)-cyclohexanol;
2-dimethylaminomethyl-4-(3-methoxy-benzyl)-1-o-tolyl-cyclohexanol;
2-dimethylaminomethyl-4-(3-methoxy-benzyl)-1-vinyl-cyclohexanol;
1-(4-tert-butyl-phenyl)-2-dimethylaminomethyl-4-(3-methoxy-benzyl)-cyclohexanol;
1-cyclopentyl-2-dimethylaminomethyl-4-(3-methoxy-benzyl)-cyclohexanol;
2-dimethylaminomethyl-4-(3-methoxy-benzyl)-1-m-tolyl-cyclohexanol;
2-dimethylaminomethyl-4-(3-methoxy-benzyl)-bicyclo-hexyl-1-ol;
2-dimethylaminomethyl-4-(3-methoxy-benzyl)-1-phenethyl-cyclohexanol;
2-dimethylaminomethyl-4-(3-methoxy-benzyl)-1-phenylethynyl-cyclohexanol
2-dimethylaminomethyl-4-(3-methoxy-benzyl)-1-thiophen-2-yl-cyclohexanol;
2-dimethylaminomethyl-4-(3-methoxy-benzyl)-1-(3-methoxy-phenyl)-cyclohexanol;
2-dimethylaminomethyl-4-(3-methoxy-benzyl)-1-(3-phenyl-propyl)-cyclohexanol;
1-(2,3-dichlorophenyl)-2-dimethylaminomethyl-4-(3-methoxy-benzyl)-cyclohexanol;
2-dimethylaminomethyl-4-(3-methoxy-benzyl)-1-p-tolyl-cyclohexanol;
1-cyclohexylmethyl-2-dimethylaminomethyl-4-(3-methoxy-benzyl)-cyclohexanol;
2-dimethylaminomethyl-1-(5-fluoro-2-methoxy-phenyl)-4-(3-methoxy-benzyl)-cyclohexanol;
1-(3-chlorophenyl)-2-dimethylaminomethyl-4-(3-methoxy-benzyl)-cyclohexanol;
1-(3,5-dichlorophenyl)-2-dimethylaminomethyl-4-(3-methoxy-benzyl)-cyclohexanol;
1-(4-chloro-3-trifluoromethyl-phenyl)-2-dimethylaminomethyl-4-(3-methoxybenzyl)-cyclohexanol;
2-dimethylaminomethyl-1-(3-fluorobenzyl)-4-(3-methoxy-benzyl)-cyclohexanol;
2-dimethylaminomethyl-4-(3-methoxy-benzyl)-1-(2-methoxy-phenyl)-cyclohexanol;
2-dimethylaminomethyl-4-(3-methoxy-benzyl)-1-(3-trifluoromethyl-phenyl)-cyclohexanol;
1 (2-chloro-6-fluorobenzyl)-2-dimethylaminomethyl-4-(3-methoxy-benzyl)-cyclohexanol;
2-dimethylaminomethyl-1-(2,5-dimethyl-benzyl)-4-(3-methoxy-benzyl)-cyclohexanol;
1-(3-chlorobenzyl)-2-dimethylaminomethyl-4-(3-methoxy-benzyl)-cyclohexanol;
2-dimethylaminomethyl-4-(4-fluorobenzyloxy)-1-phenyl-cyclohexanol;
1-benzyl-2-dimethylaminomethyl-4-(4-fluorobenzyloxy)-cyclohexanol;
2-dimethylaminomethyl-4-(4-fluorobenzyloxy)-1-(4-fluoro-3-methyl-phenyl)-cyclohexanol;
2-dimethylaminomethyl-4-(4-fluorobenzyloxy)-1-vinyl-cyclohexanol;
1-(4-tert-butyl-phenyl)-2-dimethylaminomethyl-4-(4-fluorobenzyloxy)-cyclohexanol;
1-cyclopentyl-2-dimethylaminomethyl-4-(4-fluorobenzyloxy)-cyclohexanol;
2-dimethylaminomethyl-4-(4-fluorobenzyloxy)-1-m-tolyl-cyclohexanol;
2-dimethylaminomethyl-4-(4-fluorobenzyloxy)bicyclo-hexyl-1-ol;
2-dimethylaminomethyl-4-(4-fluorobenzyloxy)-1-phenethyl-cyclohexanol;

2-dimethylaminomethyl-4-(4-fluorobenzyloxy)-1-phenylethynyl-cyclohexanol;
2-dimethylaminomethyl-4-(4-fluorobenzyloxy)-1-thiophen-2-yl-cyclohexanol;
2-dimethylaminomethyl-4-(4-fluorobenzyloxy)-1-(3-methoxy-phenyl)-cyclohexanol;
2-dimethylaminomethyl-4-(4-fluorobenzyloxy)-1-p-tolyl-cyclohexanol;
1-cyclohexylmethyl-2-dimethylaminomethyl-4-(4-fluorobenzyloxy)-cyclohexanol;
2-dimethylaminomethyl-1-(3-fluorobenzyl)-4-(4-fluorobenzyloxy)-cyclohexanol;
2-dimethylaminomethyl-4-(4-fluorobenzyloxy)-1-(2-methoxy-phenyl)-cyclohexanol;
2-dimethylaminomethyl-4-(4-fluorobenzyloxy)-1-(3-methyl-benzyl)-cyclohexanol;
2-dimethylaminomethyl-1-(2,5-dimethyl-benzyl)-4-(4-fluorobenzyloxy)-cyclohexanol;
1-(3-chlorobenzyl)-2-dimethylaminomethyl-4-(4-fluorobenzyloxy)-cyclohexanol;
[5-benzyloxy-2-(3-methoxy-phenyl)-cyclohexylmethyl]-dimethyl-amine;
[5-(3-chlorobenzyloxy)-2-(3-methoxy-phenyl)-cyclohexylmethyl]-dimethyl-amine;
[2-(3-methoxy-phenyl)-5-(naphthalen-2-ylmethoxy)-cyclohexylmethyl]-dimethylamine;
[5-(3-methoxy-benzyloxy)-2-(3-methoxy-phenyl)-cyclohexylmethyl]-dimethylamine;
[5-(4-chlorobenzyloxy)-2-(3-methoxy-phenyl)-cyclohexylmethyl]-dimethyl-amine;
[5-(4-methoxy-benzyloxy)-2-(3-methoxy-phenyl)-cyclohexylmethyl]-dimethylamine;
2-dimethylaminomethyl-1-(3-methoxy-phenyl)-4-(naphthalen-2-ylmethoxy)-cyclohexanol;
[5-(4-methoxy-benzyloxy)-2-(3-methoxy-phenyl)-cyclohex-2-enylmethyl]dimethyl-amine;
butyric acid 3-dimethylaminomethyl-4-hydroxy-4-(3-methoxy-phenyl)-cyclohexylester;
4-amino-2-dimethylaminomethyl-1-(3-methoxy-phenyl)-cyclohexanol;
2-dimethylaminomethyl-1-(3-methoxy-phenyl)-4-(naphthalen-2-ylmethoxy)-cyclohexanol;
4-methoxy-benzoic acid 3-dimethylaminomethyl-4-hydroxy-4-(3-methoxyphenyl)-cyclohexylester;
3-methoxy-benzoic acid 3-dimethylaminomethyl-4-hydroxy-4-(3-methoxyphenyl)-cyclohexylester;
2,2-dimethyl-propionic acid 3-dimethylaminomethyl-4-hydroxy-4-(3-methoxyphenyl)-cyclohexylester;
butyric acid 3-dimethylaminomethyl-4-hydroxy-4-(3-methoxy-phenyl)-cyclohexylester;
4-methoxy-benzoic acid 3-dimethylaminomethyl-4-hydroxy-4-(3-methoxyphenyl)-cyclohexylester;
3-methoxy-benzoic acid 3-dimethylaminomethyl-4-hydroxy-4-(3-methoxyphenyl)-cyclohexylester;
2,2-dimethyl-propionic acid 3-dimethylaminomethyl-4-hydroxy-4-(3-methoxyphenyl)-cyclohexylester;
3,4-dimethoxy-benzoic acid 3-dimethylaminomethyl-4-hydroxy-4-(3-methoxyphenyl)-cyclohexylester;
3,4-dimethoxy-benzoic acid 3-dimethylaminomethyl-4-hydroxy-4-(3-methoxyphenyl)-cyclohexylester;
naphthalene-2-carboxylic acid 3-dimethylaminomethyl-4-hydroxy-4-(3-methoxy-phenyl)-cyclohexylester;
4-methyl-benzoic acid 3-dimethylaminomethyl-4-hydroxy-4-(3-methoxyphenyl)-cyclohexylester;
3,4-dichloro-benzoic acid 3-dimethylaminomethyl-4-hydroxy-4-(3-methoxyphenyl)-cyclohexylester;
4-chloro-benzoic acid 3-dimethylaminomethyl-4-hydroxy-4-(3-methoxyphenyl)-cyclohexylester;
3-chloro-benzoic acid 3-dimethylaminomethyl-4-hydroxy-4-(3-methoxyphenyl)-cyclohexylester;
2-chloro-benzoic acid 3-dimethylaminomethyl-4-hydroxy-4-(3-methoxyphenyl)-cyclohexylester;
4-trifluoromethyl-benzoic acid 3-dimethylaminomethyl-4-hydroxy-4-(3methoxy-phenyl)-cyclohexylester;
3,5-difluoro-benzoic acid 3-dimethylaminomethyl-4-hydroxy-4-(3-methoxy-phenyl)-cyclohexylester;
4-fluoro-benzoic acid 3-dimethylaminomethyl-4-hydroxy-4-(3-methoxy-phenyl)-cyclohexylester;
3-fluoro-benzoic acid 3-dimethylaminomethyl-4-hydroxy-4-(3-methoxy-phenyl)-cyclohexylester;
2-fluoro-benzoic acid 3-dimethylaminomethyl-4-hydroxy-4-(3-methoxy-phenyl)-cyclohexylester;
cyclopentanecarboxylic acid 3-dimethylaminomethyl-4-hydroxy-4-(3-methoxyphenyl)-cyclohexylester;
(4-methoxy-phenyl)-acetic acid 3-dimethylaminomethyl-4-hydroxy-4-(3methoxy-phenyl)-cyclohexylester;
(3-methoxy-phenyl)-acetic acid 3-dimethylaminomethyl-4-hydroxy-4-(3methoxy-phenyl)-cyclohexylester;
phenyl-acetic acid 3-dimethylaminomethyl-4-hydroxy-4-(3-methoxy-phenyl)-cyclohexylester;
3,4,5-trimethoxy-benzoic acid 3-dimethylaminomethyl-4-hydroxy-4-(3methoxy-phenyl)-cyclohexylester;
3,5-dimethoxy-benzoic acid 3-dimethylaminomethyl-4-hydroxy-4-(3-methoxyphenyl)-cyclohexylester;
naphthalene-1-carboxylic acid 3-dimethylaminomethyl-4-hydroxy-4-(3-methoxyphenyl)-cyclohexylester;
2-methoxy-benzoic acid 3-dimethylaminomethyl-4-hydroxy-4-(3-methoxyphenyl)-cyclohexylester;
naphthalene-2-carboxylic acid 3-dimethylaminomethyl-4-hydroxy-4-(3-methoxyphenyl)-cyclohexylester;
2-hydroxy-benzoic acid 3-dimethylaminomethyl-4-hydroxy-4-(3-methoxyphenyl)-cyclohexylester;
4-methyl-benzoic acid 3-dimethylaminomethyl-4-hydroxy-4-(3-methoxyphenyl)-cyclohexylester;
3,4-dichloro-benzoic acid 3-dimethylaminomethyl-4-hydroxy-4-(3-methoxy-phenyl)-cyclohexylester;
4-chloro-benzoic acid 3-dimethylaminomethyl-4-hydroxy-4-(3-methoxyphenyl)-cyclohexylester;
3-chloro-benzoic acid 3-dimethylaminomethyl-4-hydroxy-4-(3-methoxyphenyl)-cyclohexylester;
2-chloro-benzoic acid 3-dimethylaminomethyl-4-hydroxy-4-(3-methoxyphenyl)-cyclohexylester;
4-trifluoromethyl-benzoic acid 3-dimethylaminomethyl-4-hydroxy-4-(3-methoxy-phenyl)-cyclohexylester;
3,5-difluoro-benzoic acid 3-dimethylaminomethyl-4-hydroxy-4-(3-methoxy-phenyl)-cyclohexylester;
4-fluoro-benzoic acid 3-dimethylaminomethyl-4-hydroxy-4-(3-methoxy-phenyl)-cyclohexylester;
3-fluoro-benzoic acid 3-dimethylaminomethyl-4-hydroxy-4-(3-methoxy-phenyl)-cyclohexylester;
2-fluoro-benzoic acid 3-dimethylaminomethyl-4-hydroxy-4-(3-methoxy-phenyl)-cyclohexylester;
cyclopentanecarboxylic acid 3-dimethylaminomethyl-4-hydroxy-4-(3-methoxy-phenyl)-cyclohexylester;
(4-methoxy-phenyl)-acetic acid 3-dimethylaminomethyl-4-hydroxy-3234-(3-methoxy-phenyl)-cyclohexylester;
(3-methoxy-phenyl)-acetic acid 3-dimethylaminomethyl-4-hydroxy-4-(3-methoxy-phenyl)-cyclohexylester;
phenyl-acetic acid 3-dimethylaminomethyl-4-hydroxy-4-(3-methoxy-phenyl)-cyclohexylester;
3,4,5-trimethoxy-benzoic acid 3-dimethylaminomethyl-4-hydroxy-4-(3-methoxy-phenyl)-cyclohexylester;

3,5-dimethoxy-benzoic acid 3-dimethylaminomethyl-4-hydroxy-4-(3-methoxyphenyl)-cyclohexylester;
naphthalene-1-carboxylic acid 3-dimethylaminomethyl-4-hydroxy-4-(3-methoxy-phenyl)-cyclohexylester;
2-methoxy-benzoic acid 3-dimethylaminomethyl-4-hydroxy-4-(3-methoxyphenyl)-cyclohexylester;
2-dimethylaminomethyl-1,4-bis-(3-methoxy-phenyl)-cyclohexane-1,4-diol;
2-dimethylaminomethyl-1,4-bis-(3-methoxy-phenyl)-cyclohexane-1,4-diol;
6-(4-benzyloxy-2-dimethylaminomethyl-1-hydroxy-cyclohexyl)-naphthalen-2-ol;
4-benzyloxy-2-dimethylaminomethyl-1-(6-methoxy-naphthalen-2-yl)-cyclohexanol;
butyric acid 3-dimethylaminomethyl-4-hydroxy-4-(3-methoxy-phenyl)-cyclohexylester;
butyric acid 3-dimethylaminomethyl-4-hydroxy-4-(3-methoxy-phenyl)-cyclohexylester;
2-dimethylaminomethyl-1-(3-methoxy-phenyl)-4-methylamino-cyclohexanol;
2-dimethylaminomethyl-1-(3-methoxy-phenyl-4-methylamino-cyclohexanol;
valeric acid 3-dimethylaminomethyl-4-hydroxy-4-(3-methoxy-phenyl)-cyclohexylester;
[3-dimethylaminomethyl-4-hydroxy-4-(3-methoxy-phenyl)-cyclohexyliden] acetic acid ethylester;
[3-dimethylaminomethyl-4-hydroxy-4-(3-methoxy-phenyl)-cyclohexyliden] acetic acid ethylester;
3-[2-dimethylaminomethyl-4-(4-fluorobenzyloxy)-1-hydroxy-cyclohexyl]-phenol;
4-benzyloxy-2-dimethylaminomethyl-1-(3-phenyl-propyl)-cyclohexanol;
2-dimethylaminomethyl-4-(4-fluorobenzyloxy)-1-(3-phenyl-propyl)-cyclohexanol;
2-dimethylaminomethyl-1-(3-fluorobenzyl)-4-(4-fluorobenzyloxy)-cyclohexanol;
4-benzyloxy-2-dimethylaminomethyl-1-(3-fluorobenzyl)-cyclohexanol;
2-dimethylaminomethyl-4-(4-fluorobenzyloxy)-1-p-tolyl-cyclohexanol;
4-benzyloxy-2-dimethylaminomethyl-1-p-tolyl-cyclohexanol;
2-dimethylaminomethyl-1-(2,5-dimethyl-benzyl)-4-(4-fluorobenzyloxy)-cyclohexanol;
4-benzyloxy-2-dimethylaminomethyl-1-(2,5-dimethyl-benzyl)-cyclohexanol;
1-(4-chloro-3-trifluoromethyl-phenyl)-2-dimethylaminomethyl-4-(4-fluorbenzyloxy)-cyclohexanol;
4-benzyloxy-1-(4-chloro-3-trifluoromethyl-phenyl)-2-dimethylaminomethyl-cyclohexanol;
[2,5-bis-(4-fluorobenzyloxy)-2-(3-methoxy-phenyl)-cyclohexylmethyl]-dimethylamine;
5-dimethylaminomethyl-4-(3-methoxy-phenyl)-cyclohex-3-enol;
2-dimethylaminomethyl-1-(6-methoxynaphthalen-2-yl)-cyclohexane-1,4-diol;
butyric acid 3-dimethylaminomethyl-4-hydroxy-4-(6-methoxynaphthalen-2-yl)-cyclohexylester;
benzoic acid 4-hydroxy-3-(4-methyl-piperazin-1-ylmethyl)-4-naphthalen-2-yl-cyclohexyl ester;
2-chloro-benzoic acid 4-hydroxy-3-(4-methyl-piperazin-1-ylmethyl)-4naphthalen-2-yl-cyclohexyl ester;
3-chloro-benzoic acid 4-hydroxy-3-(4-methyl-piperazin-1-ylmethyl)-4naphthalen-2-yl-cyclohexyl ester;
4-chloro-benzoic acid 4-hydroxy-3-(4-methyl-piperazin-1-ylmethyl)-4naphthalen-2-yl-cyclohexyl ester;
2-fluoro-benzoic acid 4-hydroxy-3-(4-methyl-piperazin-1-ylmethyl)-4naphthalen-2-yl-cyclohexyl ester;
3-fluoro-benzoic acid 4-hydroxy-3-(4-methyl-piperazin-1-ylmethyl)-4naphthalen-2-yl-cyclohexyl ester;
4-fluoro-benzoic acid 4-hydroxy-3-(4-methyl-piperazin-1-ylmethyl)-4naphthalen-2-yl-cyclohexyl ester;
2-methyl-benzoic acid 4-hydroxy-3-(4-methyl-piperazin-1-ylmethyl)-4naphthalen-2-yl-cyclohexyl ester;
3-methyl-benzoic acid 4-hydroxy-3-(4-methyl-piperazin-1-ylmethyl)-4naphthalen-2-yl-cyclohexyl ester;
4-methyl-benzoic acid 4-hydroxy-3-(4-methyl-piperazin-1-ylmethyl)-4naphthalen-2-yl-cyclohexyl ester;
2-methoxy-benzoic acid 4-hydroxy-3-(4-methyl-piperazin-1-ylmethyl)-4naphthalen-2-yl-cyclohexyl ester;
3-methoxy-benzoic acid 4-hydroxy-3-(4-methyl-piperazin-1-ylmethyl)-4naphthalen-2-yl-cyclohexyl ester;
4-methoxy-benzoic acid 4-hydroxy-3-(4-methyl-piperazin-1-ylmethyl)-4naphthalen-2-yl-cyclohexyl ester;
2,6-dichloro-benzoic acid 4-hydroxy-3-(4-methyl-piperazin-1-ylmethyl)-4naphthalen-2-yl-cyclohexyl ester;
2,6-difluoro-benzoic acid 4-hydroxy-3-(4-methyl-piperazin-1-ylmethyl)-4naphthalen-2-yl-cyclohexyl ester;
2-chloro5-fluoro-benzoic acid 4-hydroxy-3-(4-methyl-piperazin-1-ylmethyl)-4-naphthalen-2-yl-cyclohexyl ester;
biphenyl-4-carboxylic acid 4-hydroxy-3-(4-methyl-piperazin-1-ylmethyl)-4naphthalen-2-yl-cyclohexylester;
2-chloro-benzoic acid 4-hydroxy-4-(6-methoxy-naphthalen-2-yl)-3-(4-methyl; piperazin-1-ylmethyl)-cyclohexyl ester;
3-chloro-benzoic acid 4-hydroxy-4-(6-methoxy-naphthalen-2-yl)-3-(4-methyl-piperazin-1-ylmethyl)-cyclohexyl ester;
4-chloro-benzoic acid 4-hydroxy-4-(6-methoxy-naphthalen-2-yl)-3-(4-methyl-piperazin-1-ylmethyl)-cyclohexyl ester;
2-fluoro-benzoic acid 4-hydroxy-4-(6-methoxy-naphthalen-2-yl)-3-(4-methyl-piperazin-1-ylmethyl)-cyclohexyl ester;
3-fluoro-benzoic acid 4-hydroxy-4-(6-methoxy-naphthalen-2-yl)-3-(4-methyl-piperazin-1-ylmethyl)-cyclohexyl ester;
4-fluoro-benzoic acid 4-hydroxy-4-(6-methoxy-naphthalen-2-yl)-3-(4-methyl-piperazin-1-ylmethyl)-cyclohexyl ester;
2-methyl-benzoic acid 4-hydroxy-4-(6-methoxy-naphthalen-2-yl)-3-(4-methyl-piperazin-1-ylmethyl)-cyclohexyl ester;
3-methyl-benzoic acid 4-hydroxy-4-(6-methoxy-naphthalen-2-yl)-3-(4-methyl-piperazin-1-ylmethyl)-cyclohexyl ester;
4-methyl-benzoic acid 4-hydroxy-4-(6-methoxy-naphthalen-2-yl)-3-(4-methyl-piperazin-1-ylmethyl)-cyclohexyl ester;
2-methoxy-benzoic acid 4-hydroxy-4-(6-methoxy-naphthalen-2-yl).-3-(4-methyl-piperazin-1-ylmethyl)-cyclohexyl ester;
3-methoxy-benzoic acid 4-hydroxy-4-(6-methoxy-naphthalen-2-yl)-3-(4-methyl-piperazin-1-ylmethyl)-cyclohexyl ester;
4-methoxy-benzoic acid 4-hydroxy-4-(6-methoxy-naphthalen-2-yl)-3-(4-methyl-piperazin-1-ylmethyl)-cyclohexyl ester;
2,6-dichloro-benzoic acid 4-hydroxy-4-(6-methoxy-naphthalen-2-yl)-3-(4-methyl-piperazin-1-ylmethyl)-cyclohexyl ester;

2,6-fluoro-benzoic acid 4-hydroxy-4-(6-methoxy-naphthalen-2-yl)-3-(4-methyl-piperazin-1-ylmethyl)-cyclohexyl ester;
2-chloro-6-fluoro-benzoic acid 4-hydroxy-4-(6-methoxy-naphthalen-2-yl)-3-(4methyl-piperazin-1-ylmethyl)-cyclohexyl ester;
biphenyl-4-carboxylic acid 4-hydroxy-4-(6-methoxy-naphthalen-2-yl)-3-(4-methyl-piperazin-1-ylmethyl)-cyclohexyl ester;
4-(2-chlorobenzyloxy)-2-(4-methyl-piperazin-1-ylmethyl)-1-naphthalen-2-ylcyclohexanol;
4-(3-chlorobenzyloxy)-2-(4-methyl-piperazin-1-ylmethyl)-1-naphthalen-2-ylcyclohexanol;
4-(4-chlorobenzyloxy)-2-(4-methyl-piperazin-1-ylmethyl)-1-naphthalen-2-yl-cyclohexanol;
4-(2-fluorobenzyloxy)-2-(4-methyl-piperazin-1-ylmethyl)-1-naphthalen-2-ylcyclohexanol;
4-(3-fluorobenzyloxy)-2-(4-methyl-piperazin-1-ylmethyl)-1-naphthalen-2-ylcyclohexanol;
4-(4-fluorobenzyloxy)-2-(4-methyl-piperazin-1-ylmethyl)-1-naphthalen-2-ylcyclohexanol;
4-(2-methyl-benzyloxy)-2-(4-methyl-piperazin-1-ylmethyl)-1-naphthalen-2-ylcyclohexanol;
4-(3-methyl-benzyloxy)-2-(4-methyl-piperazin-1-ylmethyl)-1-naphthalen-2-yl-cyclohexanol;
4-(4-methyl-benzyloxy)-2-(4-methyl-piperazin-1-ylmethyl)-1-naphthalen-2-yl-cyclohexanol;
4-(2-methoxy-benzyloxy)-2-(4-methyl-piperazin-1-ylmethyl)-1-naphthalen-2-yl-cyclohexanol;
4-(3-methoxy-benzyloxy)-2-(4-methyl-piperazin-1-ylmethyl)-1-naphthalen-2-yl-cyclohexanol;
4-(4-methoxy-benzyloxy)-2-(4-methyl-piperazin-1-ylmethyl)-1-naphthalen-2-yl-cyclohexanol;
4-(2,6-dichlorobenzyloxy)-2-(4-methyl-piperazin-1-ylmethyl)-1-naphthalen-2-yl-cyclohexanol;
4-(2,6-difluorobenzyloxy)-2-(4-methyl-piperazin-1-ylmethyl)-1-naphthalen-2-yl-cyclohexanol;
4-(2-chloro-6-fluorobenzyloxy)-2-(4-methyl-piperazin-1-ylmethyl)-1-naphthalen-2-yl-cyclohexanol;
4-(2-chlorobenzyloxy)-1-(6-methoxy-naphthalen-2-yl)-2-(4-methyl-piperazin-1-ylmethyl)-cyclohexanol;
4-(3-chlorobenzyloxy)-1-(6-methoxy-naphthalen-2-yl)-2-(4-methyl-piperazin-1-ylmethyl)-cyclohexanol;
4-(4-chlorobenzyloxy)-1-(6-methoxy-naphthalen-2-yl)-2-(4-methyl-piperazin-1-ylmethyl)-cyclohexanol;
4-(2-fluorobenzyloxy)-1-(6-methoxy-naphthalen-2-yl)-2-(4-methyl-piperazin-1-ylmethyl)-cyclohexanol;
4-(3-fluorobenzyloxy)-1-(6-methoxy-naphthalen-2-yl)-2-(4-methyl-piperazin-1-ylmethyl)-cyclohexanol;
4-(4-fluorobenzyloxy)-1-(6-methoxy-naphthalen-2-yl)-2-(4-methyl-piperazin-1-ylmethyl)-cyclohexanol;
4-(2-methyl-benzyloxy)-1-(6-methoxy-naphthalen-2-yl)-2-(4-methyl-piperazin-1-ylmethyl)-cyclohexanol;
4-(3-methyl-benzyloxy)-1-(6-methoxy-naphthalen-2-yl)-2-(4-methyl-piperazin-1-ylmethyl)-cyclohexanol;
4-(4-methyl-benzyloxy)-1-(6-methoxy-naphthalen-2-yl)-2-(4-methyl-piperazin-1-ylmethyl)-cyclohexanol;
4-(2-methoxy-benzyloxy)-1-(6-methoxy-naphthalen-2-yl)-2-(4-methyl-piperazin-1-ylmethyl)-cyclohexanol;
4-(3-methoxy-benzyloxy)-1-(6-methoxy-naphthalen-2-yl)-2-(4-methyl-piperazin-1-ylmethyl)-cyclohexanol;
4-(4-methoxy-benzyloxy)-1-(6-methoxy-naphthalen-2-yl)-2-(4-methyl-piperazin-1-ylmethyl)-cyclohexanol;
4-(2,6-dichlorobenzyloxy)-1-(6-methoxy-naphthalen-2-yl)-2-(4-methyl-piperazin-1-ylmethyl)-cyclohexanol;
4-(2,6-difluorobenzyloxy)-1-(6-methoxy-naphthalen-2-yl)-2-(4-methyl-piperazin-1-ylmethyl)-cyclohexanol;
4-(2-chloro-6-fluorobenzyloxy)-1-(6-methoxy-naphthalen-2-yl)-2-(4-methyl-piperazin-1-yl-methyl)-cyclohexanol;
2-dimethylaminomethyl-4-(4-fluorobenzyloxy)-1-naphthalen-2-yl-cyclohexanol;
4-fluoro-benzoic acid 3-dimethylaminomethyl-4-hydroxy-4-(6-methoxynaphthalen-2-yl)-cyclohexylester;
4-fluoro-benzoic acid 3-dimethylaminomethyl-4-hydroxy-4-naphthalen-2-yl-cyclohexylester;
2-dimethylaminomethyl-4-(4-fluorobenzyloxy)-1-(6-methoxy-naphthalen-2-yl)-cyclohexanol; and
6-[2-dimethylaminomethyl-4-(4-fluorobenzyloxy)-1-hydroxy-cyclohexyl]naphthalen-2-ol, optionally in the form of their racemates, their pure stereoisomers, in particular enantiomers or diastereomers, or in the form of mixtures of stereoisomers, in particular the enantiomers or diastereomers, in any mixing ratio; in the illustrated form or in the form of their acids or their bases or in the form of their salts, in particular the physiologically acceptable salts, or in the form of their solvates, in particular the hydrates, in particular the hydrochloride salt or bishydrochloride salt.

The substances according to the invention are toxicologically safe, so they are suitable as a pharmaceutical active ingredient in pharmaceutical preparation. The invention also relates therefore to pharmaceutical preparations containing at least one substituted C-cyclohexylmethylamine derivative according to the invention, and optionally a suitable additive and/or auxiliary agent and/or optionally further active ingredient.

The pharmaceutical preparations according to the invention contain, in addition to at least one substituted C-cyclohexylmethylamine derivative according to the invention, optionally suitable additives and/or auxiliary agents, therefore also excipients, fillers, solvents, diluents, dyes and/or binders, and can be administered as pharmaceutical preparations in the form of injection solutions, drops or syrups, as semi-solid pharmaceutical preparations in the form of granules, tablets, pellets, patches, capsules, plasters or aerosols. The choice of auxiliary agents, etc. and the quantities thereof to be used depend on whether the pharmaceutical preparation is to be applied orally, perorally, parenterally, intravenously, intraperitoneally, intradermally, intramuscularly, intranasally, buccally, rectally or topically, for example to the skin, the mucus membranes or the eyes. Preparations in the form of tablets, dragees, capsules, granules, drops and syrups are suitable for oral application, solutions, suspensions, easily reconstitutable dry preparations and sprays are suitable for parenteral, topical and inhalative applications. Substituted C-cyclohexylmethylamine derivatives according to the invention in a deposit, in dissolved form or in a plaster, optionally with the addition of agents to promote skin penetration, are suitable percutaneous application preparations. Orally or percutaneously applicable preparation forms can release the substituted C-cyclohexylmethylamine derivatives according to the invention after a delay. In principle, other active ingredients known to the person skilled in the art can be added to the pharmaceutical preparations according to the invention.

The quantity of active ingredient to be administered to the patient varies as a function of the weight of the patient, the method of application, the indication and the severity of the illness. Conventionally, 0.005 to 1,000 mg/kg bodyweight, preferably 0.05 to 5 mg/kg of at least one substituted C-cyclohexylmethylamine derivative according to the invention are applied.

In a preferred form of the pharmaceutical preparation, a substituted C-cyclohexylmethylamine derivative is present as a pure diastereomer and/or enantiomer, as a racemate or as a non-equimolar or equimolar blend of the diastereomers and/or enantiomers.

The invention also relates to the use of a substituted C-cyclohexylmethylamine derivative according to the invention for producing a pharmaceutical composition for treating pain, in particular neuropathic or chronic pain. In this case it may be preferred if a substituted C-cyclohexylmethylamine derivative used is present as a pure diastereomer and/or enantiomer, as a racemate or as a non-equimolar or equimolar blend of the diastereomers and/or enantiomers.

The invention also relates to a method for producing a substituted C-cyclohexylmethylamine derivative according to the invention, as is recited in the following description and example.

Some methods for producing compounds according to the invention in accordance with formula I, which are analogously applied in this case, have already been described in DE 19547766 (I. Graudums et al, Grünenthal GmbH, 1995), which is herein incorporated by reference in its entirety. To produce substances according to formula I, in which A is not hydrogen, the methods described by Graudums et al. were combined with the methods known from the literature for producing substituted Mannich bases (Risch et al, Houben-Weyl—Methoden der Organischen Chemie, E21b (1995) 1925-1929; Angew. Chem. 106 (1994) 2531-2533; Synlett (1997) 974-976).

To produce substances according to the invention in which the olefins of partial formula Ia represent

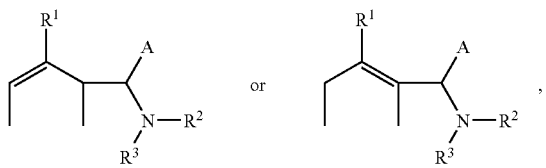

tertiary alcohols,

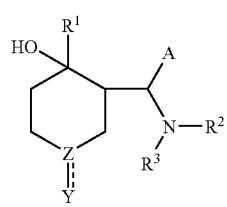

optionally in a solvent or solvent mixture at temperatures between 20 and 120° C., are treated with organic or inorganic acids or other dehydrating agents such as acid halides. Formic acid or hydrogen bromides were preferably used. One of the abovementioned olefins is preferably or exclusively obtained in this manner, as a function of the selected reaction conditions.

From these olefins

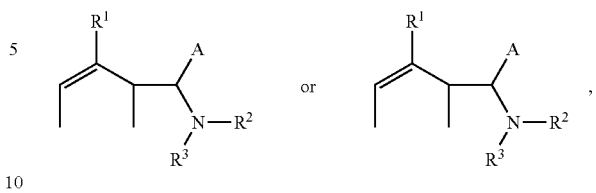

compounds according to the invention are obtained by reduction of the CC double bond, whereby

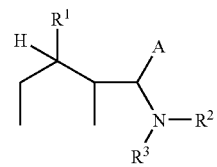

is obtained. For this purpose, the olefins are preferably hydrogenated under a hydrogen atmosphere or also excess hydrogen pressure in the presence of a transition metal which was possibly bound to a carrier.

The reaction of tertiary alcohols

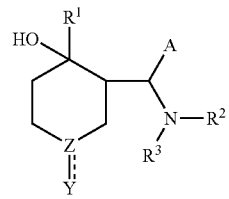

with hydrochloric acid at temperatures between −20 and +20° C. led to chlorine derivatives

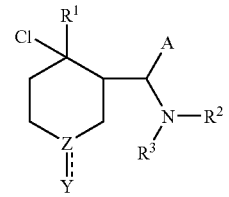

During this reaction, the duration of the reaction, the concentration of the hydrochloric acid used and the use of an optionally added solvent has an influence on the course of the reaction. Under more drastic conditions, i.e. when using concentrated hydrochloric acid, long reaction times or the application of elevated temperatures, olefins

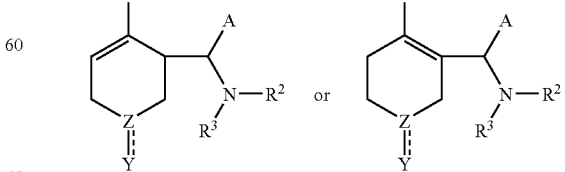

were also obtained.

The reaction of tertiary alcohols:

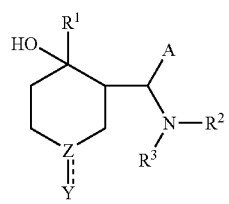

with fluorination reagents such as dimethylamino sulphur trifluoride (DAST) or Deoxofluor® led to fluorine derivatives

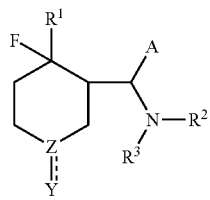

To produce substances according to the invention in which

is

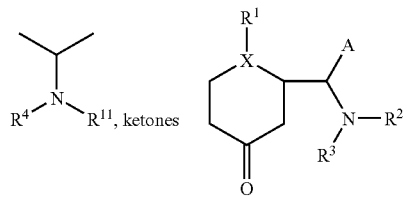

were reacted with ammonia or ammonium salts, primary or secondary amines under reductive conditions. A large number of methods known from the literature is suitable for this purpose (see e.g., R. C. Larock; *Comprehensive Organic Transformations*; VCH Publishers; New York, Weinheim, Cambridge 1989). Complex hydrides such as sodium boron hydride, sodium cyanoboron hydride or particularly preferably sodium triacetoxyboron hydride were preferably used. If primary or secondary amines were obtained in this manner, they can be reacted with acid halides or acids to form amides using the methods known from the literature, alkalated with alkyl, aryl alkyl or heteroaryl alkyl halides using methods known from the literature or can be reductively aminated with aldehydes also using methods known from the literature (R. C. Larock; *Comprehensive Organic Transformations*; VCH Publishers; New York, Weinheim, Cambridge 1989).

The production of substances according to the invention in which

is

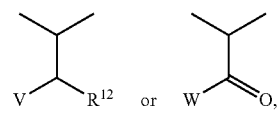

can be carried out using a large number of methods known from the literature (see e.g. R. C. Larock; *Comprehensive Organic Transformations*; VCH Publishers; New York, Weinheim, Cambridge 1989). For example, the ester

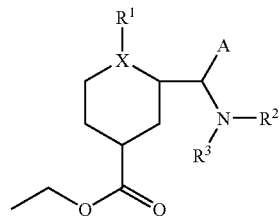

or the aldehyde

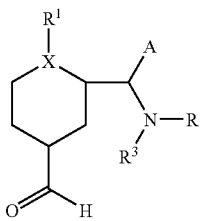

can be the starting point.
The ester

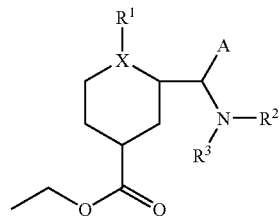

can be obtained using the above-described methods, starting from the commercially available cyclohexanone-4-carboxylic acid ether ester. The aldehyde

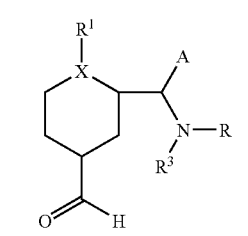

can be obtained from the ketone

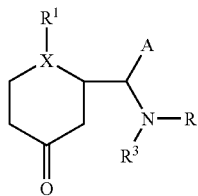

for example by a Wittig reaction with methoxymethylphosphonium chloride or bromide and acid splitting of the initially formed enol ether (G. Wittig et al, Chem. Ber. 95 (1962) 2514-2525; S, O. Bhanot et al, J. Chem. Soc. C (1968) 2583-2588).

The invention also relates to a method for the treatment, in particular the treatment of pain, of non-human mammals or humans, that requires treatment of pain, in particular chronic pain, by administration of a therapeutically effective dose of a substituted C-cyclohexylmethylamine derivative according to the invention, or of a pharmaceutical preparation according to the invention.

The invention will be described further hereinafter by examples, but is not limited thereto.

EXAMPLES

The following examples show compounds according to the invention, their production and efficacy tests carried out therewith.

In general the following details apply:

The chemicals and solvents used were acquired commercially from conventional suppliers (Acros, Avocado, Aldrich, Fluka, Lancaster, Maybridge, Merck, Sigma, TCI etc.) or synthesized using methods well known to those ordinarily skilled in the art.

Analyses were made by NMR spectroscopy, ESI mass spectrometry and/or HPLC.

Grignard Reaction 1

Reaction Equation:

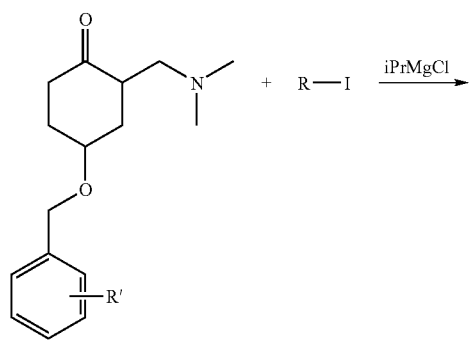

-continued

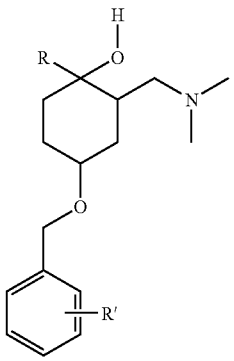

General Instruction 1 (AAV 1):

The reaction vessel was fully dried in the drying oven. The aryl iodide was introduced and 1 ml tetrahydrofuran (THF) added to it. Isopropyl magnesium chloride solution was added at −20° C. and the mixture stirred for 60 minutes before the Mannich base and further 0.25 ml THF were added. While stirring, the mixture was slowly allowed to thaw to ambient temperature and was restirred overnight. The mixture was then cooled to −20° C. again and hydrolyzed with ammonium chloride solution.

The reaction mixture was extracted three times with 3 ml ether in each case. The combined organic phases were dried by magnesium sulphate and evaporated at 40° C. under vacuum. Purification was effected by hydrochloride precipitation: dissolving the crude base in about 10 ml 2-butanone per gramme of base; addition of half a mol equivalent of water, followed by 1.1 mol equivalents of chlorotrimethylsilane and stirring overnight. If no hydrochloride formed even on cooling to about 4° C., the precipitation mixture was taken up in twice the volume of water, washed with three small portions of ether, the aqueous phase rendered alkaline with a little, about 30% sodium hydroxide solution and extracted three times with ether ("acid base extraction"). These last extracts were combined again and subjected to new hydrochloride precipitation.

| Batch A: R' = H | (Examples 1 to 28) |
|---|---|
| 2.68 mmol (700 mg) | Mannich base (1.22 M in THF) |
| 5.36 mmol | Aryl iodide (R-I) |
| 4.02 mmol (2.01 ml) | Isopropyl magnesium chloride solution (2 M in THF) |
| 1.25 ml | THF |
| 2 ml | 20% ammonium chloride solution |
| and for the working up of ether and magnesium sulphate. | |

| Batch B: R' = 4-F | (Examples 29 to 50) |
|---|---|
| 2.15 mmol (600 mg) | Mannich base (1.00 M in THF) |
| 4.30 mmol | Aryl iodide (R-I) |
| 3.22 mmol (1.61 ml) | Isopropyl magnesium chloride solution (2 M in THF) |
| 1.25 ml | THF |
| 2 ml | 20% ammonium chloride solution |
| and for the working up of ether and magnesium sulphate. | |

| Example No. | Aryl iodide | Yield (g hydrochloride) | Purification (Acid base extraction) |
|---|---|---|---|
| 1 | 1-bromo-4-iodobenzene | 0.190 | |
| 2 | 1-iodo-4-trifluoromethyl-benzene | 0.310 | |
| 3 | 1,2-difluoro-4-iodobenzene | 0.172 | x |

-continued

| | | | |
|---|---|---|---|
| 4 | 2-fluoro-4-iodotoluene | 0.098 | x |
| 5 | 4-iodo-1,2-dichlorobenzene | 0.340 | |
| 6 | 1-iodonaphthalene | 0.191 | x |
| 7 | 4-iodo-1,2-dimethylbenzene | 0.246 | x |
| 8 | 2-fluoro-5-iodotoluene | 0.167 | x |
| 9 | 4-fluoro-2-iodotoluene | 0.148 | x |
| 10 | 1-chloro-2-fluoro-4-iodobenzene | 0.151 | x |
| 11 | 4-chloro-2-iodoanisole | 0.556 | x |
| 12 | 1-bromo-2-iodobenzene | 0.208 | x |
| 13 | 2-iodoanisole | 0.644 | |
| 14 | 1-iodo-2-methylsulphanyl-benzene | 0.665 | |
| 15 | 1-chloro-4-iodobenzene | 0.194 | x |
| 16 | 1-bromo-3-iodobenzene | 0.152 | x |
| 17 | 1-bromo-2-fluoro-4-iodobenzene | 0.287 | x |
| 18 | 4-iodoanisole | 0.296 | x |
| 19 | 1-chloro-2-iodobenzene | 0.218 | x |
| 20 | 1-iodo-3-trifluoromethyl-benzene | 0.240 | x |
| 21 | 1-iodo-4-pentylbenzene | 0.164 | |
| 22 | 2-iodo-1,4-dimethylbenzene | 0.084 | x |
| 23 | 1-iodo-4-isopropylbenzene | 0.151 | x |
| 24 | 1-iodo-2,3-dimethylbenzene | 0.127 | x |
| 25 | 1-fluoro-3-iodobenzene | 0.195 | x |
| 26 | 1-iodo-3,5-bis(trifluoro-methyl)benzene | 0.220 | |
| 27 | 1-ethyl-4-iodobenzene | 0.096 | x |
| 28 | 3,5-dichloro-5-iodobenzene | 0.349 | |
| 29 | 2-iodotoluene | 0.083 | x |
| 30 | 4-iodotoluene | 0.105 | x |
| 31 | 2-iodo-1,4-dimethylbenzene | 0.089 | |
| 32 | 4-iodo-1,2-dimethylbenzene | 0.066 | x |
| 33 | 1-iodo-3,5-dimethylbenzene | 0.098 | |
| 34 | 1-iodo-4-isopropylbenzene | 0.129 | x |
| 35 | 1-fluoro-3-iodobenzene | 0.065 | x |
| 36 | 1-fluoro-4-iodobenzene | 0.100 | x |
| 37 | 1,2-difluoro-4-iodobenzene | 0.081 | |
| 38 | 2-fluoro-4-iodotoluene | 0.161 | |
| 39 | 2-fluoro-5-iodotoluene | 0.105 | |
| 40 | 1-chloro-2-iodobenzene | 0.077 | |
| 41 | 1-chloro-3-iodobenzene | 0.212 | |
| 42 | 1-chloro-4-iodobenzene | 0.107 | |
| 43 | 1,2-dichloro-4-iodobenzene | 0.255 | |
| 44 | 1-chloro-2-fluoro-4-iodobenzene | 0.092 | |
| 45 | 1,3-dichloro-5-iodobenzene | 0.183 | |
| 46 | 4-chloro-2-iodoanisole | 0.173 | x |
| 47 | 1-iodo-4-trifluormethyl-benzene | 0.106 | |
| 48 | 1-iodo-3,5-bis(trifluoro-methyl)benzene | 0.087 | |
| 49 | 2-iodoanisole | 0.243 | x |
| 50 | 1-iodo-2-methylsulphanylbenzene | 0.240 | x |

Grignard Reaction with Elimination 1

Reaction Equation:

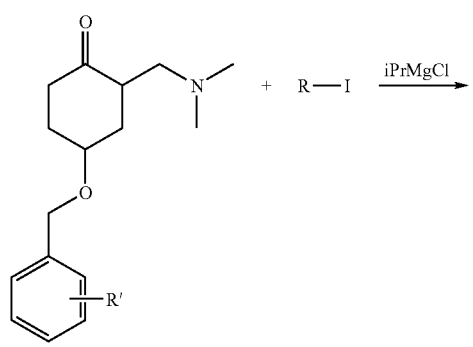

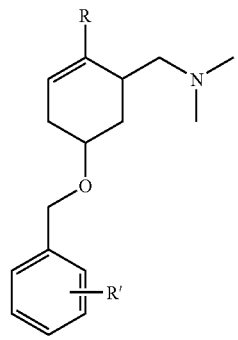

Implementation: See AAV 1.

| | Batch A: R' = H | (Example 51) | |
|---|---|---|---|
| | Batch B: R' = 4-F | (Example 52) | |
| | | | Purification |
| | | Yield | (Acid base |
| Example No. | Aryl iodide | (g hydro-chloride) | extraction) |
| 51 | 2-iodothiophene | 0.308 | x |
| 52 | 2-iodothiophene | 0.102 | |

Reaction Equation:

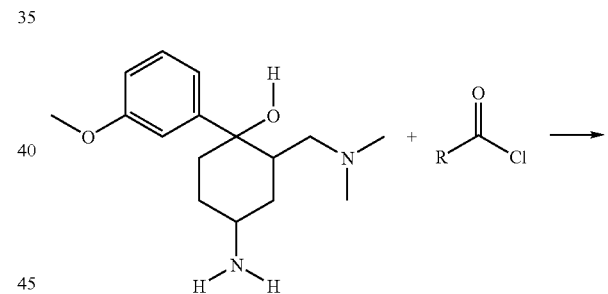

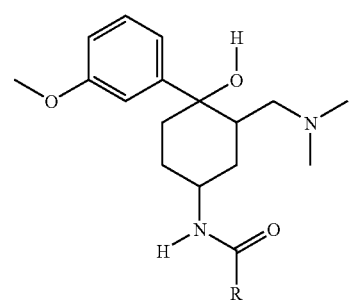

General Instruction 2 (AAV 2):

The apparatus was fully dried in the drying oven. The acid chloride was introduced and 1 ml dichloromethane added to it. Triethylamine was added at −10° C. and the mixture stirred for 20 minutes before the amine, dissolved in 4 ml dichloromethane, was added. While stirring, the mixture was slowly allowed to thaw to ambient temperature and restirred overnight.

At ambient temperature, diluted potassium hydroxide solution was added and the mixture subsequently centrifuged. The phases were separated, the organic phase dried by means of magnesium sulphate and evaporated at 40° C. under vacuum. Purification took place by hydrochloride precipitation, optionally after acid base extraction (see AAV 1).

| Batch A: | (Example 53 to 62) |
| --- | --- |
| 3.59 mmol (1.00 g) | 4-amino-2-dimethylaminomethyl-1-(3-methoxyphenyl)cyclohexanol |
| 5.39 mmol | acid chloride (RCOCl) |
| 9.74 mmol (1.36 ml) | triethylamine |
| 5 ml | dichloromethane |
| 2 ml | potassium hydroxide solution (2 M) and for the working up of magnesium sulphate. |
| Batch B: | (Example 63 and 64) |
| 2.16 mmol (600 g) | 4-amino-2-dimethylaminomethyl-1-(3-methoxyphenyl)cyclohexanol |
| 3.23 mmol | acid chloride (RCOCl) |
| 4.31 mmol (0.60 ml) | triethylamine |
| 3 ml | dichloromethane |
| 1.5 ml | potassium hydroxide solution (2 M) and for the working up of magnesium sulphate. |

| Example No. | Acid chloride | Yield (g hydrochloride) | Purification (Acid base extraction) |
| --- | --- | --- | --- |
| 53 | 3,4-dichlorobenzoylchloride | 0.627 | |
| 54 | 2-naphthoylchloride | 0.512 | |
| 55 | 3-phenylpropionylchloride | 0.119 | |
| 56 | 4-nitrobenzoylchloride | 0.975 | |
| 57 | 4-methyl-3-nitrobenzoylchloride | 0.656 | |
| 58 | 3,4,5-trimethoxybenzoylchloride | 0.236 | x |
| 59 | 4-chlorophenoxyacetylchloride | 0.639 | x |
| 60 | 3-nitrobenzoylchloride | 0.302 | x |
| 61 | 2-furoylchloride | 0.746 | x |
| 62 | phenoxyacetylchloride | 0.527 | x |
| 63 | 4-(trifluormethyl)benzoyl-chloride | 0.212 | x |
| 64 | 4-methoxybenzoylchloride | 0.510 | x |

Grignard Reaction 2

Reaction Equation:

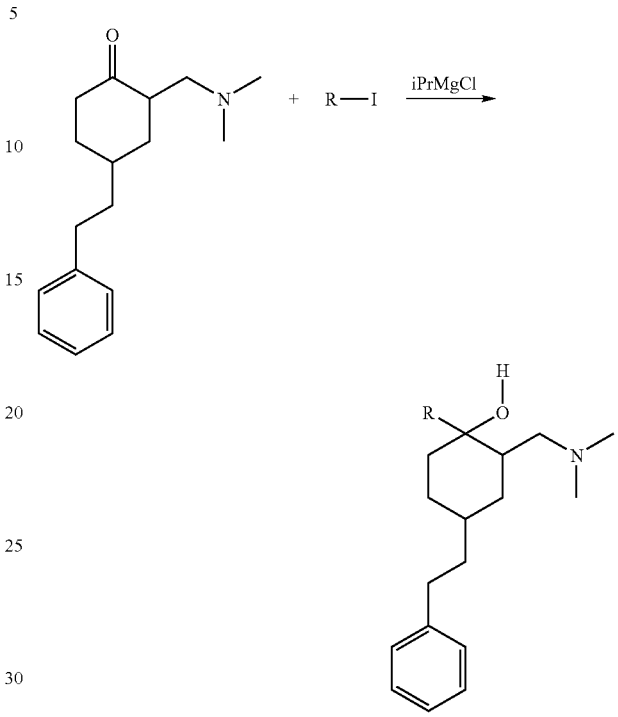

General Instruction 3 (AAV 3):

The apparatus was fully dried and aerated with nitrogen. The aryl iodide was introduced and 1 ml THF added to it. Isopropyl magnesium chloride solution was added at −20° C. and the mixture stirred for 60 minutes before the Mannich base and further 0.25 ml THF were added. While stirring, the mixture was slowly allowed to thaw to ambient temperature and was restirred overnight. The mixture was then cooled to −20° C. again and hydrolyzed with ammonium chloride solution.

The reaction mixture was extracted three times with 10 ml ether in each case. The combined organic phases were dried by magnesium sulphate and evaporated at 40° C. under vacuum. Purification was effected by column chromatography.

The purified product was then precipitated as hydrochloride and recrystallized (see AAV 1).

| Batch: | (Example 65 to 97) |
| --- | --- |
| 2.00 mmol (0.52 g) | Mannich base (1.0 M in THF) |
| 4.00 mmol | aryl iodide (R-I) |
| 3.00 mmol (1.73 ml) | isopropyl magnesium chloride solution (2 M in THF) |
| 1.25 ml | THF |
| 2 ml | 20% ammonium chloride solution and for the working up of ether and magnesium sulphate. |

| Example No. | Aryl iodide | Yield (g hydrochloride) | Purification Column chromatography | Crystallisation |
| --- | --- | --- | --- | --- |
| 65* | 1-fluoro-4-iodobenzene | 0.134 | ether/hexane/MeOH (25/25/1) | 2-butanone/ether |
| 66* | 1-fluoro-4-iodobenzene | 0.072 | ether/hexane/MeOH (25/25/1) | 2-butanone/ether |
| 67 | 1-bromo-4-iodobenzene | 0.154 | ether/hexane/MeOH (25/25/1) | 2-butanone/ether |

-continued

| | | | | |
|---|---|---|---|---|
| 68* | 1-ethyl-4-iodobenzene | 0.114 | hexane/ethyl acetate/MeOH (93/11) | 2-butanone/ether |
| 69* | 1-ethyl-4-iodobenzene | 0.225 | ether/hexane/MeOH (25/25/1) | 2-butanone/ether |
| 70 | 1-iodo-4-isopropyl-benzene | 0.093 | ether/hexane/MeOH (25/25/1) | 2-butanone/ether |
| 71* | 4-iodoanisole | 0.175 | ether/hexane/MeOH (25/25/1) | 2-butanone/ether |
| 72* | 4-iodoanisole | 0.107 | ether/hexane/MeOH (25/25/1) | 2-butanone/ether |
| 73 | 1-iodo-2,4-dimethylbenzene | 0.136 | ether/hexane/MeOH (25/25/1) | 2-butanone/ether |
| 74 | 1-iodo-2-methyl-sulphanyl-benzene | 0.204 | hexane/ethyl acetate/MeOH (9/3/1) | 2-butanone/ether |
| 75 | 4-fluoro-2-iodotoluene | 0.136 | ether/hexane/MeOH (25/25/1) | 2-butanone/ether |
| 76 | 2-iodo-1,4-dimethylbenzene | 0.176 | hexane/acetic-ester/MeOH (12/3/1) | 2-butanone/ether |
| 77 | 4-iodotoluene | 0.140 | ether/hexane/MeOH (25/25/1) | 2-butanone/ether |
| 78 | 1-fluoro-3-iodobenzene | 0.126 | hexane/ethyl acetate/MeOH (12/3/1) | 2-butanone/ether |
| 79 | 1-chloro-3-iodobenzene | 0.255 | ether/hexane/MeOH (25/25/1) | 2-butanone/ether |
| 80 | 1-chloro-2-fluoro-4-iodobenzene | 0.110 | ether/hexane/MeOH (25/25/1) | 2-butanone/ether |
| 81 | 1-iodo-3-trifluoromethyl-benzene | 0.220 | ether/hexane/MeOH (25/25/1) | 2-butanone/ether |
| 82 | 1,2-dichloro-5-iodobenzene | 0.324 | ether/hexane/MeOH (25/25/1) | 2-butanone/ether |
| 83 | 4-iodo-1,2-dimethylbenzene | 0.170 | ether/hexane/MeOH (25/25/1) | 2-butanone/ether |
| 84 | 1,2-dichloro-4-iodobenzene | 0.390 | ether/hexane/MeOH (25/25/1) | 2-butanone/ether |
| 85 | 1-chloro-4-iodobenzene | 0.202 | ether/hexane/MeOH (25/25/1) | 2-butanone/ether |
| 86 | 2-fluoro-4-iodotoluene | 0.173 | ether/hexane/MeOH (25/25/1) | 2-butanone/ether |
| 87 | 1-iodo-3,5-dimethylbenzene | 0.083 | ether/hexane/MeOH (25/25/1) | 2-butanone/ether |
| 88 | 1-bromo-2-fluoro-4-iodobeozene | 0.096 | ether/hexane/MeOH (25/25/1) | 2-butanone/ether |
| 89* | 1-iodo-2,3-dimethylbenzene | 0.145 | ether/hexane/MeOH (25/25/1) | 2-butanone/ether |
| 90* | 1-iodo-2,3-dimethylbenzene | 0.096 | ether/hexane/MeOH 25/2511 | 2-butanone/ether |
| 91 | 1-iodo-naphthalene | 0.082 | ether/hexane/MeOH (25/25/1) | 2-butanone/ether |
| 92 | 1-iodo-3,5-bis-trifluoromethyl-benzene | 0.168 | ether/hexane/MeOH (25/25/1) | 2-butanone/ether |
| 93 | 1-bromo-3-iodobenzene | 0.081 | ether/hexane/MeOH (250 5/1) | 2-butanone/ether |
| 94 | 2-fluoro-5-iodotoluene | 0.216 | ether/hexane/MeOH (25/25/1) | 2-butanone/ether |
| 95* | 3-iodotoluene | 0.079 | ether/hexane/MeOH (25/25/1) | 2-butanone/ether |
| 96* | 3-iodotoluene | 0.088 | ether/hexane/MeOH (25/25/1) | 2-butanone/ether |

*In the examples diastereomers can be isolated.

Grignard Reaction 3

Reaction Equation:

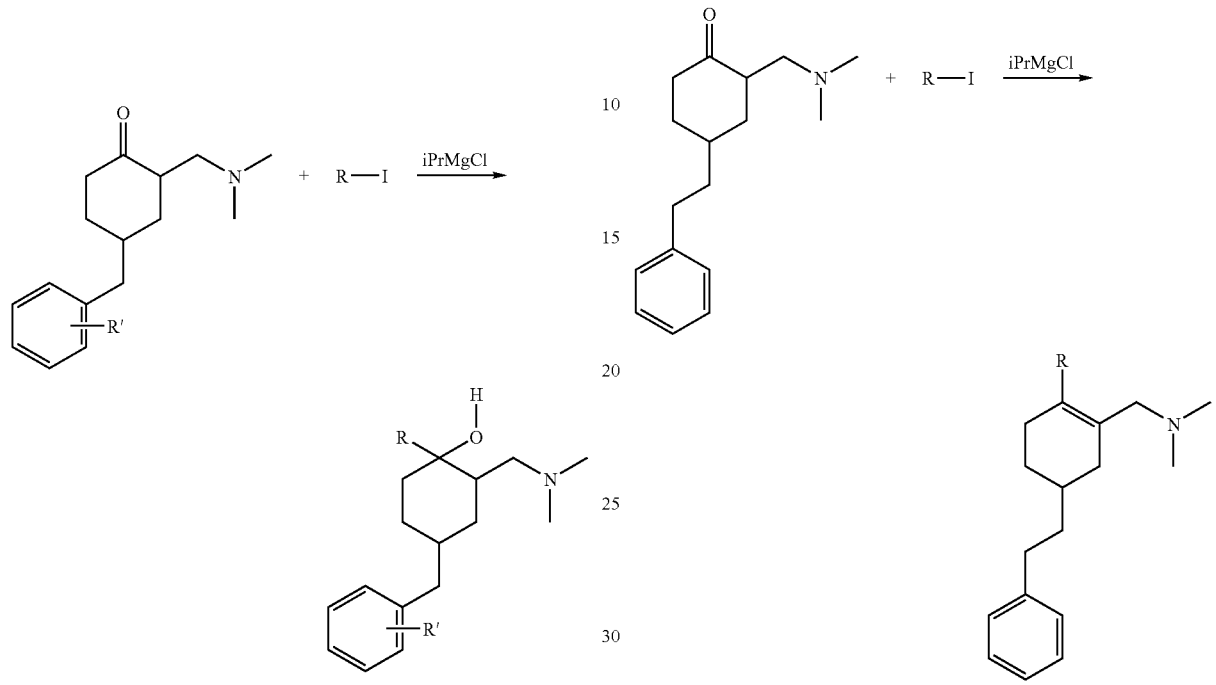

Implementation: See AAV 3.

| | Batch A: R' = H | (Example 97 and 99) | |
|---|---|---|---|
| | Batch B: R' = 3-OCH$_3$ | (Example 100 to 102) | |
| | Batch C: R' = 4-F | (Example 103 and 104) | |

| Example No. | Aryl iodide | Yield (g hydro-chloride) | Purification Column chromatography | Crystallisation |
|---|---|---|---|---|
| 97 | 3-iodotoluene | 0.033 | ether/hexane/MeOH (25/25/1) | ether/ethyl acetate |
| 98 | 1,2-difluoro-4-iodobenzene | 0.125 | ether/hexane/MeOH (25/25/1) | ether/ethyl acetate |
| 99 | 4-iodotoluene | 0.080 | ether/hexane/MeOH (25/25/1) | ether/ethyl acetate |
| 100 | 4-iodotoluene | 0.097 | ether/hexane/MeOH (25/25/1) | ether/ethyl acetate |
| 101 | 1-chloro-4-iodobenzene | 0.104 | ether/hexane/MeOH (25/25/1) | ether/ethyl acetate |
| 102 | -bromo-2-fluoro-4-iodobenzene benzene | 0.101 | ether/hexane/MeOH (25/25/1) | ether/ethyl acetate |
| 103 | 4-iodotoluene | 0.080 | ether/hexane/MeOH (25/25/1) | ether/ethyl acetate |
| 104 | -chloro-4-iodobenzene | 0.080 | ether/hexane/MeOH OH (25/25/1) | ether/ethyl acetate |

Grignard Reaction with Elimination 2

Reaction Equation:

Implementation: See AAV 3.

| Example No. | Aryl iodide | Yield (g hydro-chloride) | Purification (column chromatography) | (crystallisation) |
|---|---|---|---|---|
| 105 | 2-iodo-5-methyl-thiophene | 0.122 | ether/hexane/meOH (25/25/1) | 2-butanone/ether |

Elimination 1

Reaction Equation:

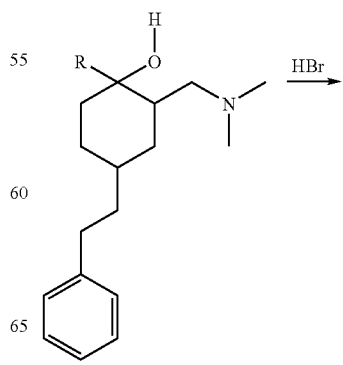

-continued

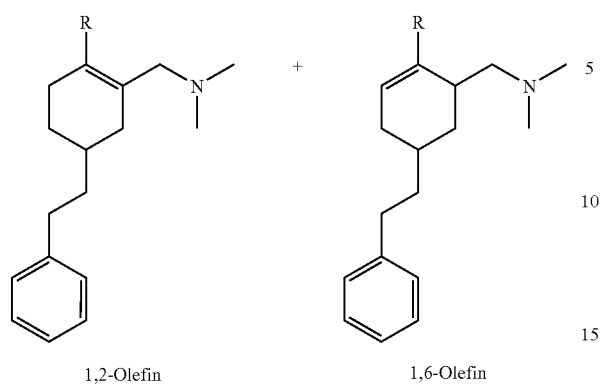

1,2-Olefin      1,6-Olefin

General Instruction 4 (AAV 4):

The tertiary alcohol was introduced and hydrobromic acid added to it. The mixture was stirred for 4 hours at an oil bath temperature of 80° C. (the mixture was optionally restirred overnight at ambient temperature). 40 g ice were then added to the mixture which was adjusted with sodium hydroxide solution to pH 10 to 11 with cooling, before it was extracted three times with about 20 ml ethyl acetate in each case. The organic phases were combined, dried with magnesium sulphate and evaporated under vacuum. The isomeric olefins were separated by column chromatography. The purified product was then precipitated as hydrochloride and recrystallized.

| Batch: | (Example 106 to 110) |
|---|---|
| 3.00 mmol | tertiary alcohol (as hydrochloride) |
| 30.0 ml | 48% hydrobromic acid |
| and for the working up of 32% sodium hydroxide solution and ethyl acetate. | |

| Example No. | Yield g hydrochloride | Purification column chromatography | crystallisation |
|---|---|---|---|
| 1,2 olefins: | | | |
| 106 | 0.050 | ether/hexane/MeOH (25/25/1) | MEK/ether |
| 107 | 0.214 | ether/hexane/MeOH (25/25/1) | MEK/ether |
| 108 | 0.074 | ether/hexane/MeOH (25/25/1) | MEK/ether |
| 109 | 0.098 | ether ethyl acetate/hexane/ MeOH (3/12/1) | MEK/ether |
| 1,6 olefins: | | | |
| 110 | 0.175 | ether/hexane/MeOH (25/25/1) | MEK/ether |
| 111 | 0.027 | ether/hexane/MeOH (25/25/1) | MEK/ether |
| 112 | 0.161 | ether/hexane/MeOH (25/25/1) | MEK/ether |

Fluorination 1

Reaction Equation:

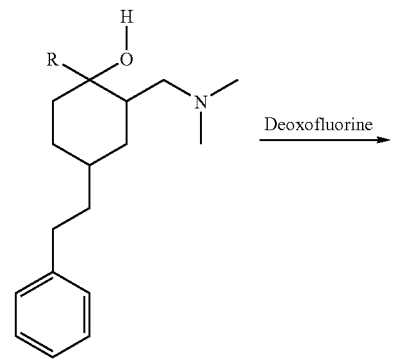

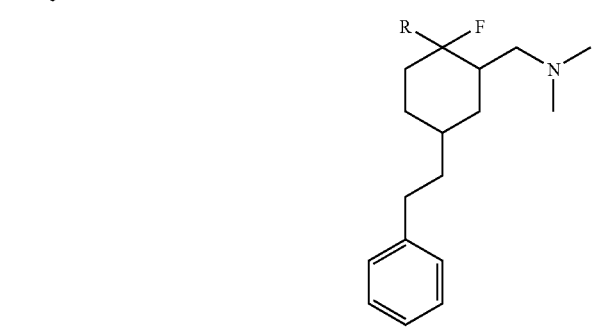

General Instruction 5 (AAV 5):

The apparatus was fully dried and aerated with nitrogen. 5 ml dichloromethane were then introduced and deoxofluorine added to it. The educt, dissolved in residual dichloromethane, was slowly added dropwise at a temperature of −5° C. and the mixture restirred for 90 minutes. While cooling some water was then added and the mixture adjusted to pH 11 by means of sodium carbonate solution. The mixture was then extracted three times with dichloromethane. The combined organic phases were dried by means of magnesium sulphate and evaporated under vacuum. Purification was effected by column chromatography. The purified product was then precipitated as hydrochloride and recrystallized.

| Batch: | (Example 113) |
|---|---|
| 1.50 mmol | educt (tertiary alcohol) |
| 5.00 mmol | deoxofluorine |
| 15 ml | dichloromethane (dried) |
| and for the working up of 32% sodium hydroxide solution and ethyl acetate. | |

| Example No. | Yield (g hydrochloride) | Purification (column chromatography) | (crystallisation) |
|---|---|---|---|
| 113 | 0.050 | ether/hexane/MeOH (25/25/1) | MEK/ether |

Fluorination 2

Reaction Equation:

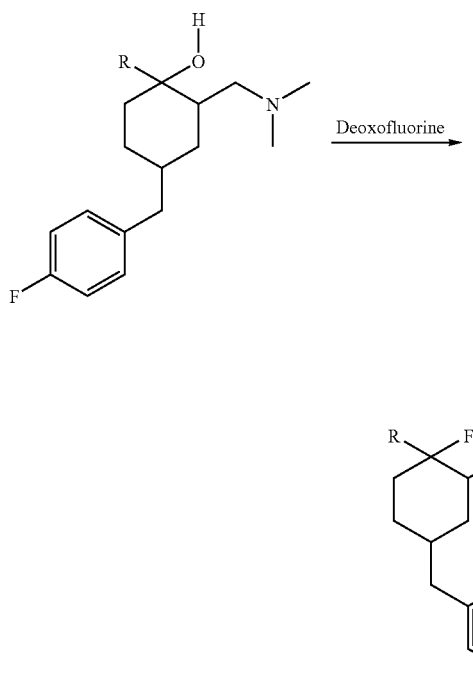

Implementation: See AAV 5:

| Example No. | Yield (g hydrochloride) | Purification | |
|---|---|---|---|
| | | (column chromatography) | (crystallisation) |
| 114 | 0.032 | ethyl acetate | ether |

Grignard Reaction 4

Reaction Equation:

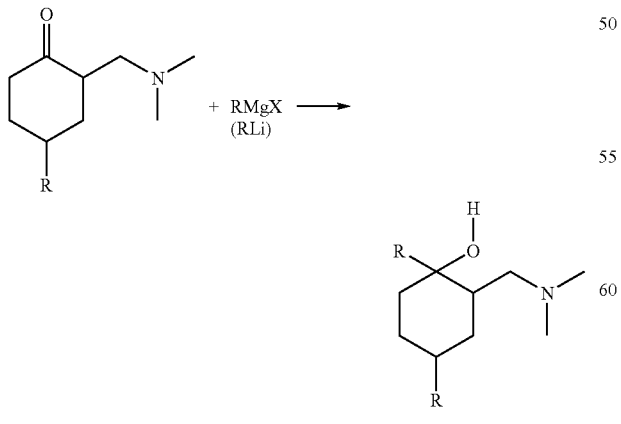

General Instruction 6 (AAV 6):

The Mannich base (400 µl, 0.5 M) dissolved in THF was introduced in a fully dried reaction vessel cooled under inert gas to −10° C. While stirring, two equivalents of the prepared Grignard or organolithium reagent were then added (0.5 M in THF or diethylether, 800 µl). The reaction mixture was stirred at ambient temperature. After three hours the mixture was cooled to −10° C. again and hydrolyzed with ammonium chloride solution.

The reaction mixture was extracted twice with ethyl acetate and evaporated at 40° C. under vacuum.

An ESI-MS was taken for characterization.

The Grignard or organolithium reagents used were produced from:

phenyl magnesium bromide
4-chlorophenyl magnesium bromide
benzyl magnesium chloride
4-fluoro-3-methylphenyl magnesium bromide
o-tolyl magnesium bromide
vinyl magnesium bromide
4-t-butylphenyl magnesium bromide
cyclopentyl magnesium chloride
m-tolyl magnesium chloride
cyclohexyl magnesium chloride
4-fluorophenyl magnesium bromide
phenethyl magnesium bromide
lithiumphenylacetylide
2-thienyllithium
1-bromomagnesium-2,4-dichlorbenzene
3-bromoanisole magnesium bromide
phenylpropyl magnesium bromide
2,3-dichlororphenyl magnesium bromide
p-toluyl magnesium bromide
4-bromoanisole magnesium bromide
cyclohexylmethyl magnesium bromide
2-bromomagnesium-4-fluoroanisole
3-fluorophenyl magnesium bromide
3-chlorophenyl magnesium bromide
3,5-dichlororphenyl magnesium bromide
2-chlorobenzyl magnesium chloride
4-fluorobenzyl magnesium chloride
3-methoxybenzyl magnesium chloride
5-bromomagnesium-2-chlorobenzotrifluoroide
3-fluorobenzyl magnesium chloride
2-methoxyphenyl magnesium bromide
2-methylbenzyl magnesium chloride
3-chloro-4-fluorophenyl magnesium bromide
3-bromomagnesiumbenzotrifluoroide
3-methylbenzyl magnesium chloride
4-chlorobenzyl magnesium chloride
2-chloro-6-fluorobenzyl magnesium chloride
2,5-dimethylbenzyl magnesium chloride
3-chlorobenzyl magnesium chloride
2,4-dichlororbenzyl magnesium chloride
2-bromomethyl-1,4-dimethylbenzene
4-bromo-1-chloro-2-trifluoromethylbenzene

| Example | Name | Calculated mass | Ascertained mass |
|---|---|---|---|
| 115 | 1-benzyl-2-(dimethylamino-phenyl-methyl)-4-phenyl-cyclohexanol | 399.57 | 400.4 |
| 116 | 2-(dimethyllamino-phenyl-methyl)-4-phenyl-1-vinyl-cyclohexanol I | 335.49 | 336.3 |
| 117 | 1-(4-tert-butyl-phenyl)-2-(dimethyl amino-phenyl-methyl)-4-phenyl-cyclohexanol | 441.65 | 442.4 |
| 118 | 2-(dimethylamino-phenyl-methyl)-4-phenyl-1-m-tolyl-cyclohexanol | 399.57 | 400.3 |
| 119 | 2-(dimethylamino-phenyl-methyl)-1-phenethyl-4-phenyl-cyclohexanol | 413.6 | 414.5 |
| 120 | 2-(dimethylamino-phenyl-methyl)-4-phenyl-1-phenylethynyl-cyclohexanol | 409.57 | 410.3 |
| 121 | 2-(dimethylamino-phenyl-methyl)-1-(3-methoxy-phenyl)-4-phenyl-cyclohexanol | 415.57 | 416.3 |
| 122 | 2-(dimethylamino-phenyl-methyl)-4-phenyl-1-(3-phenyl-propyl)-cyclohexanol | 427.63 | 428.5 |
| 123 | 2-(dimethylamino-phenyl-methyl)-1-(4-methoxy-phenyl)-4-phenyl-cyclohexanol | 415.57 | 416.3 |
| 124 | 2-(dimethylamino-phenyl-methyl)-1-(2-methoxy-phenyl)-4-phenyl-cyclohexanol | 415.57 | 416.3 |
| 125 | 4-benzyloxy-2-dimethylaminomethyl-1-phenyl-cyclohexanol | 339.47 | 340.4 |
| 126 | 1-benzyl-4-benzyloxy-2-dimethylaminomethyl-cyclohexanol | 353.5 | 354.4 |
| 127 | 4-benzyloxy-2-dimethylaminomethyl-1-(4-fluoro-3-methyl-phenyl)-cyclohexanol | 371.49 | 372.4 |
| 128 | 4-benzyloxy-2-dimethylaminomethyl-1-o-tolyl-cyclohexanol | 353.5 | 354.4 |
| 129 | 4-benzyloxy-2-dimethylaminomethyl-1-vinyl-cyclohexanol | 289.41 | 290.3 |
| 130 | 4-benzyloxy-1-cyclopentyl-2-dimethylaminomethyl-cyclohexanol | 331.49 | 332.4 |
| 131 | 4-benzyloxy-2-dimethylaminomethyl-1-m-tolyl-cyclohexanol | 353.5 | 354.4 |
| 132 | 4-benzyloxy-2-dimethylaminomethyl-bicyclohexyl-1-ol | 345.52 | 346.4 |
| 133 | 4-benzyloxy-2-dimethylaminomethyl-1-(4-fluoro-phenyl)-cyclohexanol | 357.46 | 358.3 |
| 134 | 4-benzyloxy-2-dimethylaminomethyl-1-phenylethynyl-cyclohexanol | 363.5 | 364.3 |
| 135 | 4-benzyloxy-2-dimethylaminomethyl-1-thiophen-2-yl-cyclohexanol | 345.5 | 346.4 |
| 136 | 4-benzyloxy-2-dimethylaminomethyl-1-(3-methoxy-phenyl)-cyclohexanol | 369.5 | 370.4 |
| 137 | 4-benzyloxy-2-dimethylaminomethyl-1-(3-phenyl-propyl)-cyclohexanol | 381.55 | 382.4 |
| 138 | 4-benzyloxy-2-dimethylaminomethyl-1-p-tolyl-cyclohexanol | 353.5 | 354.4 |
| 139 | 4-benzyloxy-2-dimethylaminomethyl-1-(4-methoxy-phenyl)-cyclohexanol | 369.5 | 370.3 |
| 140 | 4-benzyloxy-2-dimethylaminomethyl-1-(3-fluoro-phenyl)-cyclohexanol | 357.46 | 358.4 |
| 141 | 4-benzyloxy-1-(3-chloro-phenyl)-2-dimethylaminomethyl-cyclohexanol | 373.92 | 374.4 |
| 142 | 4-benzyloxy-2-dimethylaminomethyl-1-(3-methoxy-benzyl)-cyclohexanol | 383.53 | 384.4 |
| 143 | 4-benzyloxy-1-(4-chloro-3-trifluoromethyl-phenyl)-2-dimethylaminomethyl cyclohexanol | 441.92 | 442.3 |
| 144 | 4-benzyloxy-2-dimethylaminomethyl-1-(3-fluorobenzyl)-cyclohexanol | 371.49 | 372.4 |
| 145 | 4-benzyloxy-2-dimethylaminomethyl-1-(2-methyl-benzyl)-cyclohexanol | 367.53 | 368.4 |
| 146 | 4-benzyloxy-2-dimethylaminomethyl-1-(2,5-dimethyl-benzyl)-cyclohexanol | 381.55 | 382.4 |
| 147 | 4-(4-chlorobenzyl)-2-dimethylaminomethyl-1-(3-methoxy-phenyl)-cyclohexanol | 387.95 | 388.8 |
| 148 | 4-(4-chlorobenzyl)-2-dimethylaminomethyl-1-(3-phenyl-propyl)-cyclohexanol | 400 | 400.8 |
| 149 | 4-(4-chlorobenzyl)-1-(2,3-dichlor-phenyl)-2-dimethylaminomethyl-cyclohexanol | 426.81 | 427.0/428.9 |
| 150 | 4-(4-chlorobenzyl)-1-cyclohexylmethyl-2-dimethylaminomethyl-cyclohexanol | 377.99 | 378.8 |
| 151 | 4-(4-chlorobenzyl)-2-dimethylaminomethyl-1-(5-fluoro-2-metho-phenyl)-cyclohexanol | 405.94 | 406.7 |
| 152 | 4-(4-chlorobenzyl)-2-dimethylaminomethyl-1-(3-fluorophenyl)-cyclohexanol | 375.91 | 376.7 |
| 153 | 4-(4-chlorobenzyl)-1-(3-chloro-phenyl)-2-dimethylaminomethyl-cyclohexanol | 392.36 | 393.0 |
| 154 | 4-(4-chlorobenzyl)-1-(3,5-dichloro-phenyl)-2-dimethylaminomethyl-cyclohexanol | 426.81 | 426.5/428.3 |
| 155 | 4-(4-chlorobenzyl)-1-(2-chlorobenzyl)-2-dimethylaminomethyl-cyclohexanol | 406.39 | 406.9 |
| 156 | 4-(4-chlorobenzyl)-2-dimethylaminomethyl-1-(4-fluorobenzyl)-cyclohexanol | 389.94 | 390.8 |

-continued

| Example | Name | Calculated mass | Ascertained mass |
|---|---|---|---|
| 157 | 4-(4-chlorobenzyl)-2-dimethylaminomethyl-1-(3-fluorobenzyl)-cyclohexanol | 389.94 | 390.7 |
| 158 | 4-(4-chlorobenzyl)-2-dimethylaminomethyl-1-(2-methoxy-phenyl)-cyclohexanol | 387.95 | 388.8 |
| 159 | 4-(4-chlorobenzyl)-2-dimethylaminomethyl-1-(2-methyl-benzyl)-cyclohexanol | 385.97 | 386.8 |
| 160 | 4-(4-chlorobenzyl)-2-dimethylaminomethyl-1-(3-methyl-benzyl)-cyclohexanol | 385.97 | 386.7 |
| 161 | 1,4-bis-(4-chlorobenzyl)-2-dimethylaminomethyl-cyclohexanol | 406.39 | 407.1 |
| 162 | 4-(4-chlorobenzyl)-1-(2-chloro-6-fluorobenzyl)-2-dimethylaminomethyl-cyclohexanol | 424.38 | 425.1 |
| 163 | 4-(4-chlorobenzyl)-2-dimethylaminomethyl-1-(2,5-dimethyl-benzy)1-cyclohexanol | 400 | 400.8 |
| 164 | 4-(4-chlorobenzyl)-1-(3-chlorobenzyl)-2-dimethylaminometh i-cyclohexanol | 406.39 | 407.0 |
| 165 | 4-(4-chlorobenzyl)-1-(2,4-dichlorobenzyl)-2-dimethylaminomethyl-cyclohexanol | 440.84 | 440.9/442.4 |
| 166 | 4-(4-chlorobenzyl)-2-dimethylaminomethyl-1-phenyl-cyclohexanol | 357.92 | 358.5 |
| 167 | 4-(4-chlorobenzyl)-1-(4-chloro-phenyl)-2-dimethylaminomethyl-cyclohexanol | 392.36 | 392.7/394.5 |
| 168 | 4-(4-chlorobenzyl)-2-dimethylaminomethyl-1-(4-fluoro-3-methyl-phenyl)-cyclohexanol | 389.94 | 390.6 |
| 169 | 4-(4-chlorobenzyl)-2-dimethylaminomethyl-1-o-tolyl-cyclohexanol | 371.95 | 372.5 |
| 170 | 4-(4-chlorobenzyl)-2-dimethylaminomethyl-1-vinyl-cyclohexanol | 307.86 | 308.5 |
| 171 | 4-(4-chlorobenzyl)-1-cyclopentyl-2-dimethylaminomethyl-cyclohexanol | 349.94 | 350.3 |
| 172 | 4-(4-chlorobenzyl)-2-dimethylaminomethyl-1-m-tolyl-cyclohexanol | 371.95 | 372.5 |
| 173 | 4-(4-chlorobenzyl)-2-dimethylaminomethyl-bicyclohexyl-1-ol | 363.97 | 364.4 |
| 174 | 4-(4-chlorobenzyl)-2-dimethylaminomethyl-1-(4-fluorophenyl)-cyclohexanol | 375.91 | 376.5 |
| 175 | 4-(4-chlorobenzyl)-2-dimethylaminomethyl-1-phenethyl-cyclohexanol | 385.97 | 386.5 |
| 176 | 4-(4-chlorobenzyl)-2-dimethylaminomethyl-1-phenylethynyl-cyclohexanol | 381.94 | 382.5 |
| 177 | 4-(4-chlorobenzyl)-2-dimethylaminomethyl-1-thiophen-2-yl-cyclohexanol | 363.95 | 364.4 |
| 178 | 4-(4-chlorobenzyl)-2-dimethylaminomethyl-1--tolyl-cyclohexanol | 371.95 | 372.6 |
| 179 | 4-(4-chlorobenzyl)-2-dimethylaminomethyl-1-(4-methoxy-phenyl)-cyclohexanol | 387.95 | 388.6 |
| 180 | 4-(4-chlorobenzyl)-2-dimethylaminomethyl-1-trimethylsilanylethynyl-cyclohexanol | 378.03 | 378.7 |
| 181 | 4-(4-chlorobenzyl)-1-(4-chloro-3-trifluoromethyl-phenyl)-2-dimethylaminomethyl-cyclohexanol | 460.36 | 460.8/462.1 |
| 182 | 4-(4-chlorobenzyl)-1-(3-chloro-4-fluoro-phenyl)-2-dimethylaminomethyl-cyclohexanol | 410.35 | 410.6/412.4 |
| 183 | 4-(4-chlorobenzyl)-2-dimethylaminomethyl-1-(3-trifluoromethyl-phenyl)-cyclohexanol | 425.92 | 426.6 |
| 184 | 2-dimethylaminomethyl-4-(4-fluorobenzyl)-1--phenyl-cyclohexanol | 341.46 | 342.4 |
| 185 | 1-(4-chloro-phenyl)-2-dimethylaminomethyl-4-(4-fluorobenzyl)-cyclohexanol | 375.91 | 376.5 |
| 186 | 1-benzyl-2-dimethylaminomethyl-4-(4-fluoro-benzyl)-cyclohexanol | 355.49 | 356.4 |
| 187 | 2-dimethylaminomethyl-4-(4-fluorobenzyl)-1-(4-fluoro-3-methyl-phenyl)-cyclohexanol | 373.48 | 374.4 |
| 188 | 2-dimethylaminomethyl-4-(4-fluorobenzyl)-1-o-tolyl-cyclohexanol | 355.49 | 356.4 |
| 189 | 2-dimethylaminomethyl-4-(4-fluorobenzyl)-1-vinyl-cyclohexanol | 291.4 | 292.3 |
| 190 | 1-(4-tert-butyl-phenyl)-2-dimethylaminomethyl-4-(4-fluorobenzyl)-cyclohexanol | 397.57 | 398.4 |
| 191 | 1-cyclopentyl-2-dimethylaminomethyl-4-(4-fluorobenzyl)-cyclohexanol | 333.49 | 334.5 |
| 192 | 2-dimethylaminomethyl-4-(4-fluorobenzyl)-1-m-tolyl-cyclohexanol | 355.49 | 356.3 |
| 193 | 2-dimethylaminomethyl-4-(4-fluorobenzyl)-bic clohexyl-1-ol | 347.51 | 348.4 |
| 194 | 2-dimethylaminomethyl-4-(4-fluorobenzyl)-1-(4-fluorophenyl)-cyclohexanol | 359.45 | 360.4 |

-continued

| Example | Name | Calculated mass | Ascertained mass |
|---|---|---|---|
| 195 | 2-dimethylaminomethyl-4-(4-fluorobenzyl)-1-phenethyl-cyclohexanol | 369.52 | 370.4 |
| 196 | 2-dimethylaminomethyl-4-(4-fluorobenzyl)-1-phenylethynyl-cyclohexanol | 365.49 | 366.3 |
| 197 | 2-dimethylaminomethyl-4-(4-fluorobenzyl)-1-thiophen-2-yl-cyclohexanol | 347.49 | 348.3 |
| 198 | 2-dimethylaminomethyl-4-(4-fluorobenzyl)-1-(3-methoxy-phenyl)-cyclohexanol | 371.49 | 372.3 |
| 199 | 2-dimethylaminomethyl-4-(4-fluorobenzyl)-1-(3-phenyl-propyl)-cyclohexanol1-(2,3-dichlorophenyl)-2- | 383.55 | 384.4 |
| 200 | dimethylaminomethyl-4-(4-fluorobenzyl)-cyclohexanol | 410.35 | 410.6/412.4 |
| 201 | 2-dimethylaminomethyl-4-(4-fluorobenzyl)-1-p-tolyl-cyclohexanol | 355.49 | 356.4 |
| 202 | 2-dimethylaminomethyl-4-(4-fluorobenzyl)-1-(4-methoxy-phenyl)-cyclohexanol | 371.49 | 372.3 |
| 203 | 1-cyclohexylmethyl-2-dimethylaminomethyl-4-(4-fluorobenzyl)-cyclohexanol | 361.54 | 362.4 |
| 204 | 2-dimethylaminomethyl-4-(4-fluorobenzyl)-1-(5-fluoro-2-methoxy-phenyl)-cyclohexanol | 389.48 | 390.4 |
| 205 | 2-dimethylaminomethyl-4-(4-fluorobenzyl)-1-(3-fluorophenyl)-cyclohexanol | 359.45 | 360.4 |
| 206 | 1-(3-chlorophenyl)-2-dimethylaminomethyl-4-(4-fluorobenzyl)-cyclohexanol | 375.91 | 376.5/377.5 |
| 207 | 1-(3,5-dichloro-phenyl)-2-dimethylaminomethyl-4-(4-fluorobenzyl)-cyclohexanol | 410.35 | 410.6/412.3 |
| 208 | 1-(2-chlorobenzyl)-2-dimethylaminomethyl-4-(4-fluoro-benzyl)-cyclohexanol | 389.94 | 390.7 |
| 209 | 2-dimethylaminomethyl-1,4-bis-(4-fluoro-benzyl-cyclohexanol | 373.48 | 374.5 |
| 210 | 2-dimethylaminomethyl-4-(4-fluorobenzyl)-1-(3-methoxy-benzyl)-cyclohexanol | 385.52 | 386.4 |
| 211 | 1-(4-chloro-3-trifluoromethyl-phenyl)-2-dimethylaminomethyl-4-(4-fluorobenzyl)-cyclohexanol | 443.91 | 444.5/445.4 |
| 212 | 2-dimethylaminomethyl-4-(4-fluorobenzyl)-1-3-fluorobenzyl-cyclohexanol | 373.48 | 374.4 |
| 213 | 2-dimethylaminomethyl-4-(4-fluorobenzyl)-1-2-methoxy-phenyl-cyclohexanol | 371.49 | 372.4 |
| 214 | 2-dimethylaminomethyl-4-(4-fluorobenzyl)-1-2-methyl-benzyl-cyclohexanol | 369.52 | 370.4 |
| 215 | 1-(3-chloro-4-fluoro-phenyl)-2-dimethylaminomethyl-4-(4-fluorobenzyl)-cyclohexanol | 393.9 | 394.5 |
| 216 | 2-dimethylaminomethyl-4-(4-fluorobenzyl)-1-(3-trifluoromethyl-phenyl)-cyclohexanol | 409.46 | 410.5 |
| 217 | 2-dimethylaminomethyl-4-(4-fluorobenzyl)-1-(3-methyl-benzyl)-cyclohexanol | 369.52 | 370.4 |
| 218 | 1-(4-chlorobenzyl)-2-dimethylaminomethyl-4-4-fluorobenzyl-cyclohexanol | 389.94 | 390.5 |
| 219 | 1-(2-chloro-6-fluorobenzyl)-2-dimethylaminomethyl-4-(4-fluorobenzyl) cyclohexanol | 407.93 | 408.5 |
| 220 | 2-dimethylaminomethyl-1-(2,5-dimethyl-benzyl-4-(4-fluorobenzyl)-cyclohexanol | 383.55 | 384.4 |
| 221 | 1-(3-chlorobenzyl)-2-dimethylaminomethyl-4-(4-fluorobenzyl)-cyclohexanol | 389.94 | 390.4/391.3 |
| 222 | 1-(2,4-dichlorobenzyl)-2-dimethylaminomethyl-4-(4-fluorobenzyl)-cyclohexanol | 424.38 | 424.5/426.3 |
| 223 | 2-dimethylaminomethyl-4-(3-methoxy-benzyl)-1-phenyl-cyclohexanol | 353.5 | 354.5 |
| 224 | 1-benzyl-2-dimethylaminomethyl-4-(3-methoxy-benzyl)-cyclohexanol | 367.53 | 368.6 |
| 225 | 2-dimethylaminomethyl-1-(4-fluoro-3-methyl-phenyl)-4-(3-methoxy-benzyl)-cyclohexanol | 385.52 | 386.4 |
| 226 | 2-dimethylaminomethyl-4-(3-methoxy-benzyl)-1-o-tolyl-cyclohexanol | 367.53 | 368.5 |
| 227 | 2-dimethylaminomethyl-4-(3-methoxy-benzyl)-1-vinyl-cyclohexanol | 303.44 | 304.3 |
| 228 | 1-(4-tert-butyl-phenyl)-2-dimethylaminomethyl-4-(3-methoxy-benzyl)--Cyclohexanol | 409.61 | 410.7 |
| 229 | 1-cyclopentyl-2-dimethylaminomethyl-4-(3-methoxy-benzyl-cyclohexanol | 345.52 | 346.4 |
| 230 | 2-dimethylaminomethyl-4-(3-methoxy-benzyl)-1-m-tolyl-cyclohexanol | 367.53 | 368.4 |
| 231 | 2-dimethylaminomethyl-4-(3-methoxy-benzyl)-biclohexyl-1-ol | 359.55 | 360.4 |
| 232 | 2-dimethylaminomethyl-4-(3-methoxy-benzyl)-1-phenethyl-cyclohexanol | 381.55 | 382.4 |
| 233 | 2-dimethylaminomethyl-4-(3-methoxy-benzyl)-1-phenylethynyl-cyclohexanol | 377.52 | 378.4 |

-continued

| Example | Name | Calculated mass | Ascertained mass |
|---|---|---|---|
| 234 | 2-dimethylaminomethyl-4-(3-methoxy-benzyl)-1-thiophen-2-I-cyclohexanol | 359.53 | 360.3 |
| 235 | 2-dimethylaminomethyl-4-(3-methoxy-benzyl-1-(3-methoxy-phenyl-cyclohexanol | 383.53 | 384.4 |
| 236 | 2-dimethylaminomethyl-4-(3-methoxy-benzyl)-1-(3-phenyl-propyl-cyclohexanol | 395.58 | 396.6 |
| 237 | 1-(2,3-dichloro-phenyl)-2-dimethylaminomethyl-4-(3-methoxy-benzyl)-cyclohexanol | 422.39 | 422.8/424.5 |
| 238 | 2-dimethylaminomethyl-4-(3-methoxy-benzyl)-1-tolyl-cyclohexanol | 367.53 | 368.5 |
| 239 | 1-cyclohexylmethyl-2-dimethylaminomethyl-4-(3-methoxy-benzyl)-cyclohexanol | 373.58 | 374.8 |
| 240 | 2-dimethylaminomethyl-1-(5-fluoro-2-methoxy-phenyl)-4-(3-methoxy-benzyl) cyclohexanol | 401.52 | 402.5 |
| 241 | 1-(3-chloro-phenyl)-2-dimethylaminomethyl-4-(3-methoxy-benzyl)-cyclohexanol | 387.95 | 388.5 |
| 242 | 1-(3,5-dichloro-phenyl)-2-dimethylaminomethyl-4-(3-methoxy-benzyl)-cyclohexanol | 422.39 | 422.7/424.5 |
| 243 | 1-(4-chloro-3-trifluoromethyl-phenyl)-2-dimethylaminomethyl-4-(3-methoxy-benzyl)-cyclohexanol | 455.94 | 456.6/457.4 |
| 244 | 2-dimethylaminomethyl-1-(3-fluorobenzyl)-4-(3-methoxy-benzyl)-cyclohexanol | 385.52 | 386.4 |
| 245 | 2-dimethylaminomethyl-4-(3-methoxy-benzyl)-1-(2-methoxy-phenyl)-cyclohexanol | 383.53 | 384.4 |
| 246 | 2-dimethylaminomethyl-4-(3-methoxy-benzyl)-1-(3-trifluoromethyl-phenyl)-Cyclohexanol | 421.5 | 422.6 |
| 247 | 1-(2-chloro-6-fluorobenzyl)-2-dimethyl aminomethyl-4-(3-methoxy-benzyl)-Cyclohexanol | 419.96 | 420.9/422.6 |
| 248 | 2-dimethylaminomethyl-1-(2,5-dimethyl-benzyl)-4-(3-methoxy-benzyl)-cyclohexanol | 395.58 | 396.7 |
| 249 | 1-(3-chlorobenzyl)-2-dimethylaminomethyl-4-(3-methoxy-benzyl)-cyclohexanol | 401.97 | 402.9 |
| 250 | 2-dimethylaminomethyl-4-(4-fluoro-benzyloxy)-1-phenyl-cyclohexanol | 357.46 | 358.4 |
| 251 | 1-benzyl-2-dimethylaminomethyl-4-(4-fluoro-benzyloxy)-cyclohexanol | 371.49 | 372.8 |
| 252 | 2-dimethylaminomethyl-4-(4-fluoro-benzyloxy)-1-(4-fluoro-3-methyl-phenyl)--cyclohexanol | 389.48 | 390.4 |
| 253 | 2-dimethylaminomethyl-4-(4-fluoro-benzyloxy)-1-vinyl-cyclohexanol | 307.4 | 308.6 |
| 254 | 1-(4-tert-butyl-phenyl)-2-dimethylaminomethyl-4-(4-fluorobenzyloxy)-cyclohexanol | 413.57 | 414.6 |
| 255 | 1-cyclopentyl-2-dimethyl aminomethyl-4-(4-fluorobenzyloxy)-cyclohexanol | 349.48 | 350.4 |
| 256 | 2-dimethylaminomethyl-4-(4-fluoro-benzyloxy)-1-m-tolyl-cyclohexanol | 371.49 | 372.5 |
| 257 | 2-dimethylaminomethyl-4-(4-fluoro-benzyloxy)-bicyclohexyl-1-ol | 363.51 | 364.6 |
| 258 | 2-dimethylaminomethyl-4-(4-fluoro-benzyloxy)-1-phenethyl-cyclohexanol | 385.52 | 386.5 |
| 259 | 2-dimethylaminomethyl-4-(4-fluoro-benzyloxy)-1-phenylethynyl-cyclohexanol | 381.49 | 382.6 |
| 260 | 2-dimethylaminomethyl-4-(4-fluoro-benzyloxy)-1-thiophen-2-yl-cyclohexanol | 363.49 | 364.6 |
| 261 | 2-dimethylaminomethyl-4-(4-fluoro-benzyloxy)-1-(3-methoxy-phenyl)-cyclohexanol | 387.49 | 388.6 |
| 262 | 2-dimethylaminomethyl-4-(4-fluoro-benzyloxy)-1-p-tolyl-cyclohexanol | 371.49 | 372.6 |
| 263 | 1-cyclohexylmethyl-2-dimethylaminomethyl-(4-4-fluorobenzyloxy)-cyclohexanol | 377.54 | 379.0 |
| 264 | 2-dimethylaminomethyl-1-(3-fluorobenzyl)-4-(4-fluorobenzyloxy)-cyclohexanol | 389.48 | 390.7 |
| 265 | 2-dimethylaminomethyl-4-(4-fluoro-benzyloxy)-1-(2-methoxy-phenyl)-cyclohexanol | 387.49 | 388.8 |
| 266 | 2-dimethylaminomethyl-4-(4-fluoro-benzyloxy-1-3-methyl-benzyl-cyclohexanol | 385.52 | 387.0 |
| 267 | 2-dimethylaminomethyl-1-(2,5-dimethyl-benzyl--(4-fluorobenzyloxy-cyclohexanol | 399.54 | 400.9 |
| 268 | 1-(3-chlorobenzyl)-2-dimethylaminomethyl-4-(4-fluorobenzyloxy)-cyclohexanol | 405.94 | 406.8 |
| 340 | 4-benzyloxy-2-dimethylaminomethyl-1-(3-phenyl-propyl) cyclohexanol; hydrochloride | | |
| 341 | 2-dimethylaminomethyl-4-(4-fluorobenzyloxy)-1-(3-phenyl-propyl)-cyclohexanol; hydrochloride | | |
| 342 | 2-dimethylaminomethyl-1-(3-fluorobenzyl)-4-(4-fluorobenzyloxy)-cyclohexanol; hydrochloride | | |

-continued

| Example | Name | Calculated mass | Ascertained mass |
|---|---|---|---|
| 343 | 4-benzyloxy-2-dimethylaminomethyl-1-3-fluorobenzyl-cyclohexanol; hydrochloride | | |
| 344 | 2-dimethylaminomethyl-4-(4-fluorobenzyloxy)-1-p-tolyl-cyclohexanol; hydrochloride | | |
| 345 | 4-benzyloxy-2-dimethylaminomethyl-1-p-tolyl-cyclohexanol; hydrochloride | | |
| 346 | 2-dimethylaminomethyl-1-(2,5-dimethyl-benzyl)-4-(4-fluorobenzyloxy)-cyclohexanol; hydrochloride | | |
| 347 | 4-benzyloxy-2-dimethylaminomethyl-1-(2,5-dimethyl-benzyl)-cyclohexanol; hydrochloride | | |
| 348 | 1-(4-chloro-3-trifluoromethyl-phenyl)-2-dimethylaminomethyl-4-(4-fluoro benzyloxy)-cyclohexanol; hydrochloride | | |
| 349 | 4-benzyloxy-1-(4-chloro-3-trifluoromethyl-phenyl)-2 dimethylaminomethyl-cyclohexanol; hydrochloride | | |

Alkylation

Reaction Equation:

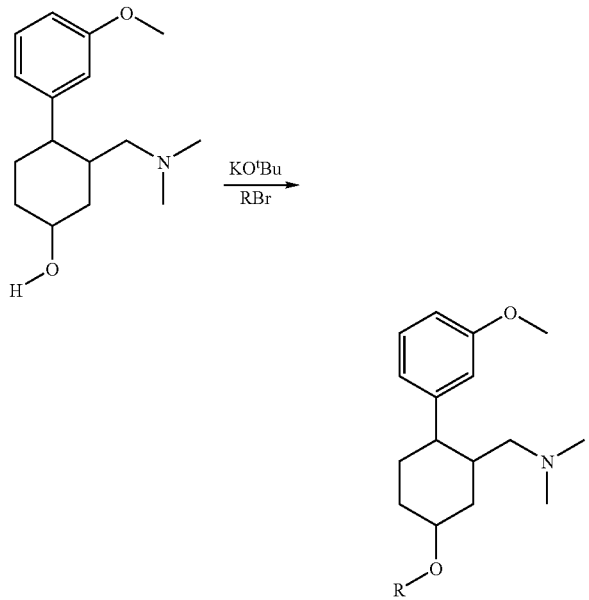

General Instruction 7 (AAV 7):

360 mg 3-dimethylaminomethyl-4-(3-methoxyphenyl) cyclohexanol hydrochloride were introduced into 3 ml THF p.a., 340 mg potassium-tert.-butylate (2.5 mol equivalents) added and restirred for 15 minutes. The correspondingly substituted benzyl bromide (1.5 mol equivalents) was then dissolved in 0.6 ml THF p.a., added dropwise and restirred for 16 hours at ambient temperature.

For working up, 2.2 ml water were added, the mixture then extracted twice with 10 ml ethyl acetate in each case, the combined extracts dried by sodium sulphate, filtered and concentrated. The crude products were chromotographed on silica gel with ethyl acetate/methanol/hexane (V/V/V=1:1:1). The products obtained were converted with chlorotrimethylsilane in aqueous 2-butanone into the corresponding hydrochlorides in the same way as in AAV 1.

When producing [5-(4-methoxybenzyloxy)-2-(3-methoxyphenyl)cyclohexylmethyl]-dimethylamine, the cyclohexene derivative [5-(4-methoxybenzyloxy)-2-(3-methoxyphenyl)cyclohex-2-enylmethyl]dimethylamine was isolated as a secondary product, as the 3-dimethylaminomethyl-4-(3-methoxyphenyl)cyclohexanol hydrochloride used was contaminated by the preliminary stage 5-dimethylaminomethyl-4-(3-methoxyphenyl)-cyclohex-3-enol hydrochloride which was catalytically hydrogenated by palladium to produce 3-dimethylaminomethyl-4-(3-methoxyphenyl)cyclohexanol.

Examples according to AAV 7:

| | | |
|---|---|---|
| 269 | [5-benzyloxy-2-(3-methoxy-phenyl)-cyclohexylmethyl]-dimethyl-amine; hydrochloride | |
| 270 | [5-(3-chlorobenzyloxy)-2-(3-methoxy-phenyl)-cyclohexylmethyl]- dimethyl-amine; hydrochloride | |
| 271 | [2-(3-methoxy-phenyl)-5-(naphthalen-2-ylmethoxy)-cyclohexylmethyl]- dimethyl-amine; hydrochloride | |
| 272 | [5-(3-methoxy-benzyloxy)-2-(3-methoxy-phenyl)-cyclohexylmethyl]- dimethyl-amine; hydrochloride | |
| 273 | [5-(4-chlorobenzyloxy)-2-(3-methoxy-phenyl)-cyclohexylmethyl]- dimethyl-amine; hydrochloride | |
| 274 | [5-(4-methoxy-benzyloxy)-2-(3-methoxy-phenyl)-cyclohexylmethyl]- dimethyl-amine; hydrochloride | |
| 275 | 2-dimethylaminomethyl-1-(3-methoxy-phenyl)-4-(naphthalen-2- ylmethoxy)-cyclohexanol; hydrochloride | |
| 276 | [5-(4-methoxy-benzyloxy)-2-(3-methoxy-phenyl)-cyclohex-2- enylmethyl]-dimethyl-amine; hydrochloride | |

Alkylation 2

Reaction Equation:

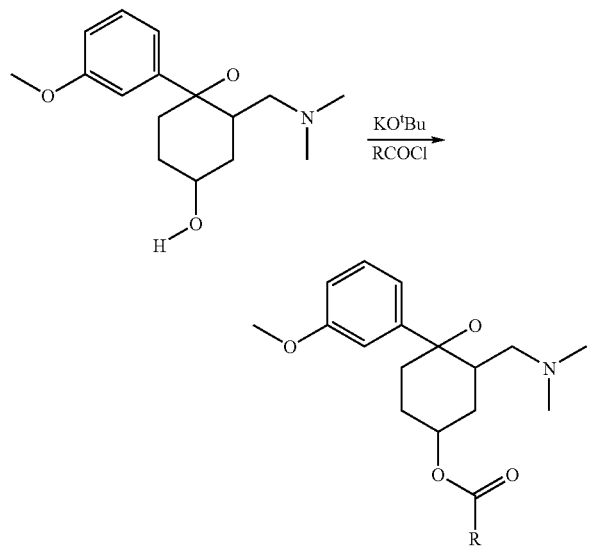

General Instruction 9 (AAV 8):

5 ml of a 0.5 M solution of potassium-tert.-butylate were introduced in THF p.a. in the dried reaction vessel, 2 ml of a 1 M solution of the respective alcohol in THF p.a. added at −10° C., stirred for 30 minutes with heating to ambient temperature, cooled to −10° C. again, 2 ml of a 1.25 M solution of the corresponding acid chloride added in THF p.a. and stirred for 1 hour at 30° C.

For working up, 2 ml 1M sodium hydrogen carbonate solution was added at 0° C., the supernatant THF phase separated, chromatographed on silica gel with diisopropyl ether/methanol (V/V=1/1) and the product obtained converted by dissolution in 2-butanone and addition of water and chlorotrimethylsilane into the hydrochloride in the same way as in AAV 1.

Mixtures according to AAV 8 with 2-dimethylaminomethyl-1-(3-methoxyphenyl)cyclohexane-1,4-diol hydrochloride (equatorial alcohol):

- 282 2,2-dimethyl-propionic acid 3-dimethylaminomethyl-4-hydroxy-4-(3-methoxy-phenyl)-cyclohexylester; hydrochloride
- 281 3-methoxy-benzoic acid 3-dimethylaminomethyl-4-hydroxy-4-(3-methoxy-phenyl)-cyclohexylester; hydrochloride
- 280 4-methoxy-benzoic acid 3-dimethylaminomethyl-4-hydroxy-4-(3-methoxy-phenyl)-cyclohexylester; hydrochloride
- 307 2-methoxy-benzoic acid 3-dimethylaminomethyl-4-hydroxy-4-(3-methoxy-phenyl)-cyclohexylester; hydrochloride
- 306 naphthalene-1-carboxylic acid 3-dimethylaminomethyl-4-hydroxy-4-(3-methoxy-phenyl)-cyclohexylester; hydrochloride
- 305 3,5-dimethoxy-benzoic acid 3-dimethylaminomethyl-4-hydroxy-4-(3-methoxy-phenyl)-cyclohexylester; hydrochloride
- 304 3,4,5-trimethoxy-benzoic acid 3-dimethylaminomethyl-4-hydroxy-4-(3-methoxy-phenyl)-cyclohexylester; hydrochloride
- 303 phenyl-acetic acid 3-dimethylaminomethyl-4-hydroxy-4-(3-methoxy-phenyl)-cyclohexylester; hydrochloride
- 302 (3-methoxy-phenyl)-acetic acid 3-dimethylaminomethyl-4-hydroxy-4-(3-methoxy-phenyl)-cyclohexylester; hydrochloride
- 301 (4-methoxy-phenyl)-acetic acid 3-dimethylaminomethyl-4-hydroxy-4-(3-methoxy-phenyl-cyclohexylester; hydrochloride
- 300 cyclopentancarboxylic acid 3-dimethylaminomethyl-4-hydroxy-4-(3-methoxy-phenyl)-cyclqhexyl ester; hydrochloride
- 299 2-fluoro-benzoic acid 3-dimethylaminomethyl-4-hydroxy-4-(3-methoxy-phenyl)-cyclohexylester; hydrochloride
- 298 3-fluoro-benzoic acid 3-dimethylaminomethyl-4-hydroxy-4-(3-methoxy-phenyl)-cyclohexylester; hydrochloride
- 297 4-fluoro-benzoic acid 3-dimethylaminomethyl-4-hydroxy-4-(3-methoxy-phenyl)-cyclohexylester; hydrochloride
- 296 3,5-difluoro-benzoic acid 3-dimethylaminomethyl-4-hydroxy-4-(3-methoxy-phenyl)-cyclohexylester; hydrochloride
- 295 4-trifluoromethyl-benzoic acid 3-dimethylaminomethyl-4-hydroxy-4-(3-methoxy-phenyl)-cyclohexylester; hydrochloride
- 294 2-chloro-benzoic acid 3-dimethylaminomethyl-4-hydroxy-4-(3-methoxy-phenyl)-cyclohexylester; hydrochloride
- 293 3-chloro-benzoic acid 3-dimethylaminomethyl-4-hydroxy-4-(3-methoxy-phenyl)-cyclohexylester; hydrochloride
- 292 4-chloro-benzoic acid 3-dimethylaminomethyl-4-hydroxy-4-(3-methoxy-phenyl)-cyclohexylester; hydrochloride
- 291 3,4-dichloro-benzoic acid 3-dimethylaminomethyl-4-hydroxy-4-(3-methoxy-phenyl)-cyclohexylester; hydrochloride
- 290 4-methyl-benzoic acid 3-dimethylaminomethyl-4-hydroxy-4-(3-methoxy-phenyl)-cyclohexylester; hydrochloride
- 309 2-hydroxy-benzoic acid 3-dimethylaminomethyl-4-hydroxy-4-(3-methoxy-phenyl)-cyclohexylester; hydrochloride
- 289 naphthalene-2-carboxylic acid 3-dimethylaminomethyl-4-hydroxy-4-(3-methoxy-phenyl)-cyclohexylester; hydrochloride
- 287 3,4-dimethoxy-benzoic acid 3-dimethylaminomethyl-4-hydroxy-4-(3-methoxy-phenyl)-cyclohexylester; hydrochloride
- 336 valeric acid 3-dimethylaminomethyl-4-hydroxy-4-(3-methoxy-phenyl)-cyclohexylester; hydrochloride Mixtures according to AAV 8 with 2-dimethylaminomethyl-1-(3-methoxyphenyl)cyclohexane-1,4-diol hydrochloride (axial alcohol):

- 277 butyric acid 3-dimethyl aminomethyl-4-hydroxy-4-(3-methoxy-phenyl)-cyclohexylester; hydrochloride
- 286 2,2-dimethyl-propionic acid 3-dimethylaminomethyl-4-hydroxy-4-(3-methoxy-phenyl)-cyclohexylester; hydrochloride
- 285 3-methoxy-benzoic acid 3-dimethylaminomethyl-4-hydroxy-4-(3-methoxy-phenyl)-cyclohexylester; hydrochloride
- 284 4-methoxy-benzoic acid 3-dimethylaminomethyl-4-hydroxy-4-(3-methoxy-phenyl)-cyclohexylester; hydrochloride
- 327 2-methoxy-benzoic acid 3-dimethylaminomethyl-4-hydroxy-4-(3-methoxy-phenyl)-cyclohexylester; hydrochloride
- 326 naphthalene-1-carboxylic acid 3-dimethylaminomethyl-4-hydroxy-4-(3-methoxy-phenyl)-cyclohexylester; hydrochloride
- 325 3,5-dimethoxy-benzoic acid 3-dimethylaminomethyl-4-hydroxy-4-(3-methoxy-phenyl)-cyclohexylester; hydrochloride
- 324 3,4,5-trimethoxy-benzoic acid 3-dimethylaminomethyl-4-hydroxy-4-3-methoxy-phenyl)-cyclohexylester; hydrochloride
- 323 phenyl-acetic acid 3-dimethyl aminomethyl-4-hydroxy-4-(3-methoxy-phenyl)-cyclohexylester; hydrochloride
- 322 (3-methoxy-phenyl)-acetic acid 3-dimethylaminomethyl-4-hydroxy-4-3-methoxy-phenyl)-cyclohexylester; hydrochloride
- 321 (4-methoxy-phenyl)-acetic acid 3-dimethylaminomethyl-4-hydroxy-4-3-methoxy-phenyl)-cyclohexylester; hydrochloride
- 320 cyclopentane carboxylic acid 3-dimethylaminomethyl-4-hydroxy-4-(3-methoxy-phenyl)-cyclohexylester; hydrochloride
- 319 2-fluoro-benzoic acid 3-dimethylaminomethyl-4-hydroxy-4-(3-methoxy-phenyl)-cyclohexylester; hydrochloride
- 318 3-fluoro-benzoic acid 3-dimethylaminomethyl-4-hydroxy-4-(3-methoxy-phenyl)-cyclohexylester; hydrochloride
- 317 4-fluoro-benzoic acid 3-dimethylaminomethyl-4-hydroxy-4-(3-methoxy-phenyl)-cyclohexylester; hydrochloride
- 316 3,5-difluoro-benzoic acid 3-dimethylaminomethyl-4-hydroxy-4-(3-methoxy-phenyl)-cyclohexylester; hydrochloride
- 315 4-trifluoromethyl-benzoic acid 3-dimethylaminomethyl-4-hydroxy-4-(3-methoxy-phenyl)-cyclohexylester; hydrochloride
- 314 2-chloro-benzoic acid 3-dimethylaminomethyl-4-hydroxy-4-(3-methoxy-phenyl)-cyclohexylester; hydrochloride
- 313 3-chloro-benzoic acid 3-dimethylaminomethyl-4-hydroxy-4-(3-methoxy-phenyl)-cyclohexylester; hydrochloride
- 312 4-chloro-benzoic acid 3-dimethylaminomethyl-4-hydroxy-4-(3-methoxy-phenyl)-cyclohexylester; hydrochloride
- 311 3,4-dichloro-benzoic acid 3-dimethylaminomethyl-4-hydroxy-4-(3-methoxy-phenyl)-cyclohexylester; hydrochloride -continued 310 4-methyl-benzoic acid 3-dimethylaminomethyl-4-hydroxy-4-(3-methoxy-phenyl)-cyclohexylester; hydrochloride
308 naphthalene-2-carboxylic acid 3-dimethylaminomethyl-4-hydroxy-4-(3-methoxy-phenyl)-cyclohexylester; hydrochloride
288 3,4-dimethoxy-benzoic acid 3-dimethyl aminomethyl-4-hydroxy-4-(3-methoxy-phenyl)-cyclohexylester; hydrochloride Example 278

4-amino-2-dimethylaminomethyl-1-(3-methoxyphenyl)cyclohexanol Dihydrochloride 2.43 g dry zinc chloride were introduced in portions and while stirring into a solution of 2.64 g sodium cyanoborohydride in 45 ml dried methanol and subsequently stirred for 30 minutes. This solution was slowly added dropwise to a suspension of 16.7 g dry ammonium acetate and 9.0 g 3-dimethylaminomethyl-4-hydroxy-4-(3-methoxyphenyl) cyclohexanone in 45 ml dry methanol and subsequently stirred for 72 hours at ambient temperature.

For working up, 45 ml semi-concentrated hydrochloric acid were added dropwise in the ice bath, subsequently stirred for 1 hour after addition had finished and the methanol was removed under vacuum. 30 g potassium hydroxide were added to the residue with ice cooling and the mixture was extracted three times with 25 ml dichloromethane in each case, the combined extracts dried by potassium carbonate, filtered and concentrated. The isolated crude product (8.8 g) was chromotographised on silica gel. The 6.25 g of 4-amino-2-dimethylaminomethyl-1-(3-methoxyphenyl)cyclohexanol obtained were converted into the corresponding dihydrochloride in the same way as in AAV 1.

Examples 334 and 335

2-dimethylaminomethyl-1-(3-methoxyphenyl)-4-methylamino-cyclohexanol Dihydrochloride (Equatorial and Axial Amine)

18.8 g 3-dimethylaminomethyl-4-hydroxy-4-(3-methoxyphenyl)cyclohexanone were dissolved in 210 ml THF p.a. under a nitrogen atmosphere, 24.3 ml 5.6 M methyl amine solution in THF added to the ice/methanol bath, followed by 5.72 ml glacial acetic acid and a total of 20.0 g sodium triacetoxyborhydride added in portions. After the additions had finished the cooling bath was removed and the mixture subsequently stirred for 16 hours with heating to ambient temperature.

For working up, 120 ml sodium hydroxide solution were added, the mixture extracted three times with 100 ml diethyl ether in each case, the extracts combined, washed twice with 50 ml water in each case, dried by sodium sulphate, filtered and concentrated. 2.5 g of the crude product obtained (17.4 g) were chromatographised with methanol on silica gel. 580 or 600 mg of two diastereomer 2-dimethyl-aminomethyl-1-(3-methoxyphenyl)-4-methylaminocyclohexanols were obtained which corresponded to the axial and the equatorial product and these were converted into the corresponding dihydrochlorides in the same way as in AAV 1.

Example 279

2-dimethylaminomethyl-1-(3-methoxyphenyl)-4-(naphthalen-2-ylmethoxy)cyclohexanol Hydrochloride 2-dimethylaminomethyl-1-(3-methoxyphenyl)-4-(naphthalen-2-ylmethoxy)-cyclohexanol and the corresponding hydrochloride were produced in the same way as in AAV 7 from 2-dimethylaminomethyl-1-(3-methoxyphenyl)cyclohexane-1,4-diol hydrochloride and 2-bromomethylnaphthalene.

Example 350

(2,5-bis-(4-fluorobenzyloxy)-2-(3-methoxyphenyl)-cyclohexylmethyl]-dimethylamine Hydrochloride When reacting 2-dimethylaminomethyl-1-(3-methoxyphenyl)-cyclohexane-1,4-diol hydrochloride with 4-fluorobenzylbromide in accordance with AAV 7, (2,5-bis-(4-fluorobenzyloxy)-2-(3-methoxyphenyl)-cyclohexylmethyl]-dimethylamine was also obtained as a secondary product after chromatographic purification on silica gel, which was converted into the corresponding hydrochloride in the same way as in AAV 1.

Example 283

Butyric Acid 3-dimethylaminomethyl-4-hydroxy-4-(3-methoxyphenhyl)-cyclohexylester Hydrochloride 28.0 g 3-dimethylaminomethyl-4-hydroxy-4-(3-methoxyphenhyl)cyclohexanone were dissolved in 140 ml isopropanol under a nitrogen atmosphere, 1.72 g sodium tetrahydridoborate were added in portions and the mixture subsequently stirred for 1 hour. For working up, initially 91 ml 2 M hydrochloric acid were added, then 20 ml 10 M sodium hydroxide solution were added, the mixture extracted twice with 100 ml dichloromethane in each case, the combined extracts dried by sodium sulphate, filtered and concentrated. The crude product obtained (29.8 g) was dissolved in 500 ml acetone and by addition of 1.82 ml water, followed by 12.7 ml chlorotrimethylsilane and stirring overnight converted into 25.7 g 2-dimethylaminomethyl-1-(3-methoxyphenyl)cyclohexane-1,4-diol hydrochloride (equatorial alcohol). After adding 2 M sodium carbonate solution and extracting twice with ethyl acetate, 5.6 g of the enriched diastereoisomer reduction product could be isolated from the mother liquor, and this was purified by chromatography on silica gel with ethyl acetate/methanol (V/V=1:3). After hydrochloride precipitation, 4.1 g 2-dimethylaminomethyl-1-(3-methoxyphenyl)cyclohexane-1,4-diol hydrochloride (axial alcohol) were obtained.

205 g 2-dimethylaminomethyl-1-(3-methoxyphenyl)cyclohexane-1,4-diol hydrochloride (equatorial alcohol) were suspended in 2,050 ml THF p.a. under a nitrogen atmosphere, 149 g potassium-tert.-butylate were slowly added, the mixture stirred for 1 hour, 71 ml butyrylchloride added dropwise and the mixture stirred for a further hour, before 36 g potassium-tert.-butylate and 34 ml butyryl chloride were again added. For working up, 980 ml water were added, the mixture extracted twice with 1,000 ml ethyl acetate in each case, the combined extracts washed with a little 1 M sodium hydrogen carbonate solution, dried by magnesium sulphate, filtered and concentrated. The crude product obtained (236 g) was combined with a further, analogously produced charge of this crude product (232 g), dissolved in 2,400 ml acetone and 470 ml dry ethanol and by adding half a mol equivalent of water and a mol equivalent of chlorotrimethylsilane, 442 g of the hydrochloride of butyric acid 3-dimethylaminomethyl-4-hydroxy-4-(3-methoxyphenyl)cyclohexylester were obtained.

Examples 332 and 333

(+)- and (−)-butyric Acid 3-dimethylaminomethyl-4-hydroxy-4-(3-methoxyphenyl)cyclohexylester The enantiomers (+)- and (−)-butyric acid 3-dimethylaminomethyl-4-hydroxy-4-(3-methoxyphenyl)cyclohexylester were produced by enzymatic resolution of racemates of butyric acid 3-dimethylaminomethyl-4-hydroxy-4-(3-methoxyphenyl)cyclohexylester and subsequent isolation of the remaining butyrate and repeated esterification of the 2-dimethylaminomethyl-1-(3-methoxyphenyl)cyclohexane-1,4-diols obtained, as described for the racemate (Gais, Hans-Joachim; Griebel, Carsten; Buschmann, Helmut; Tetrahedron: Asymmetry 11 (2000) 917-928).

Example 351

5-dimethylaminomethyl-4-(3-methoxyphenyl)-cyclohex-3-enol Hydrochloride 20.0 g 2-dimethylaminomethyl-1-(3-methoxyphenyl)cyclohexane-1,4-diol (equatorial alcohol) were dissolved in 300 ml concentrated formic acid, 6.75 ml acetyl chloride were added and the mixture heated for two hours to reflux. After cooling the mixture was concentrated, the residue taken up with 2 M sodium hydroxide solution and extracted with ethyl acetate. The combined extracts were dried by sodium sulphate, filtered, concentrated, the crude product obtained (16.7 g) dissolved in 2-butanone and by addition of 1.15 ml water and 8.1 ml chlorotrimethylsilane 5-dimethylaminomethyl-4-(3-methoxyphenyl)-cyclohex-3-enol hydrochloride (17.7 g) precipitated.

Examples 328 and 329

2-dimethylaminomethyl-1,4-bis-(3-methoxyphenyl)-cyclohexane-1,4-diol Hydrochloride (Cis- and Trans-Diol)

The corresponding Grignard reagent was produced in 60 ml THF p.a. from 7.47 g magnesium and 38.9 ml 3-bromoanisole, a solution of 40 g 1,4-dioxa-spiro[4.5]decan-8-one added dropwise in 75 ml THF p.a. at about 10° C. and subsequently stirred for 1 hour. For working up, 20 mass percent ammonium chloride solution was added to the ice bath, extracted with ethyl acetate, the combined extracts dried by sodium sulphate, filtered and concentrated. 128 ml water, 62 g ice and a solution of 31.5 ml concentrated hydrochloric acid in 385 ml were added to the crude product obtained (61.6 g) in the ice bath, the mixture stirred for five hours at 5 to 10° C., extracted with ethyl acetate, the combined extracts dried by sodium sulphate, filtered and concentrated. The crude product was mixed with diisopropyl ether and the remaining solids filtered off. 14.0 g 4-hydroxy-4-(3-methoxyphenyl)cyclohexanone were obtained.

4.23 g dimethylmethylene ammonium chloride and a drop of acetyl chloride were added in 100 ml acetonitrile to 10.0 g 4-hydroxy-4-(3-methoxyphenyl)cyclohexanone and the mixture stirred for 16 hours. The precipitated solid was filtered off, washed with a little acetonitrile and dried under vacuum. 12.2 g 2-dimethylaminomethyl-4-hydroxy-4-(3-methoxyphenyl)-cyclohexanone were obtained.

The corresponding Grignard reagent was obtained in 20 ml THF p.a. from 0.75 g magnesium and 3.9 ml 3-bromoanisole, a solution of 3.87 g 2-dimethylaminomethyl-4-hydroxy-4-(3-methoxyphenyl)cyclohexanone added dropwise in 25 ml THF p.a. added dropwise at about 10° C. and the mixture stirred for 1 hour. For working up, 20 mass percent ammonium chloride solution was added in the ice bath, extracted with ethyl acetate, the combined extracts dried by sodium sulphate, filtered and concentrated. The crude product (5.44 g) obtained was chromatographed with ethyl acetate/methanol (V/V=1:1) on silica gel. The diastereomer 2-dimethylaminomethyl-1,4-bis-(3 methoxyphenyl)-cyclohexane-1,4-diols (cis- and trans-diol) obtained were converted with chlorotrimethylsilane in aqueous 2-butanone into the corresponding hydrochlorides (240 and 777 mg) in the same way as in AAV 1.

Examples 337 and 338

(E)- and (Z)-[3-dimethylaminomethyl-4-hydroxy-4-(3-methoxyphenyl)cyclohexyl-iden] Ethyl Acetate Hydrochloride 100 g 1,4-dioxa-spiro[4.5]decan-8-one were dissolved in 800 ml toluene, 534 ml 32 mass percent sodium hydroxide solution were added, a solution of 127 ml triethylphosphonoacetate added dropwise in 250 ml toluene with ice cooling and intensive stirring and the mixture subsequently stirred for 1 hour. The organic phase was separated off, the aqueous phase extracted with toluene, the combined organic phases washed three times with water, dried by sodium sulphate, filtered and concentrated. The crude product obtained was chromatographed with diisopropylether/hexane (V/V=1:1) on silica gel. 92.9 g (1,4-dioxa-spiro[4.5]dec-8-ylidene) ethyl acetate were obtained.

92.8 g (1,4-dioxa-spiro[4.5]dec-8-ylidene) ethyl acetate were dissolved in 465 ml diisopropyl ether, 186 ml water and 137 ml concentrated hydrochloric acid added, stirred for 1 hour, the phases separated, the aqueous phase extracted twice with diisopropyl ether, the combined organic phases dried by sodium sulphate, filtered and concentrated. The crude product obtained (95.9 g) was chromatographed with diisopropyl ether/hexane (V/V=2:1) on silica gel. In addition to 17.2 g of unreacted (1,4-dioxa-spiro[4.5]dec-8-ylidene) ethyl acetate, 76.3 g (4-oxocyclohexylidene) ethyl acetate were obtained.

7.5 g dimethylmethylene ammonium chloride were added to 87.6 g (4-oxocyclohexylidene) ethyl acetate in 260 ml acetonitrile, heated for 1 hour to 60° C., 250 ml diisopropyl ether added and the mixture stirred overnight at ambient temperature. The precipitated solids were filtered off, washed with a little acetonitrile and dried under vacuum. 30.4 g (E)-(3-dimethylaminomethyl-4-oxocyclo-hexylidene) ethyl acetate were obtained. The mother liquor was concentrated to dryness and the residue (95 g) recrystallized from 475 ml 20-butanone. 62.3 g (Z)-(3-dimethylaminomethyl-4-oxocyclohexylidene) ethyl acetate were obtained.

The corresponding Grignard reagent was produced in 10 ml THF p.a. from 0.37 g magnesium and 1.9 ml 3-bromoanisole, a solution of 2.40 g (Z)-(3-dimethylaminomethyl-4-oxocyclohexylidene) ethyl acetate in 24 ml THF p.a. added dropwise with ice cooling and subsequently stirred for 1 hour. For working up, 5 ml 4 M ammonium chloride solution were added in the ice bath, the organic phase separated off, the aqueous phase extracted twice with ethyl acetate, the combined organic phases dried by sodium sulphate, filtered and concentrated. The crude product obtained (3.20 g) was chromatographed with diisopropyl ether/methanol (V/V=1:1) on silica gel. 1.61 g (Z)-[3-dimethylaminomethyl-4-hydroxy-4-(3-methoxyphenyl)cyclohexylidene) ethyl acetate were obtained and converted into the corresponding hydrochloride in the same was as in AAV 1. In the same way, 1.48 g of the hydrochloride of (E)-[3-dimethylaminomethyl-4-hydroxy-4-(3-methoxyphenyl)cyclohexylidene) ethyl acetate were produced from 2.40 g (E)-)-(3-dimethylaminomethyl-4-oxocyclohexylidene) ethyl acetate.

Example 352

2-dimethylaminomethyl-1-(6-methoxynaphthalen-2-yl)cyclohexane-1,4-diol Hydrochloride The corresponding Grignard reagent was produced in 720 ml THF p.a. from 18.2 g magnesium and 177 g 2-bromo-6-methoxynaphthalene, a solution of 105 g 7-dimethylaminomethyl-1,4-dioxa-spiro[4.5]decan-8-one in 315 ml THF p.a. added dropwise with ice cooling and the mixture subsequently stirred for 1 hour. For working up, 375 ml 4 M ammonium chloride solution were added to the ice bath, the organic phase separated off, the aqueous phase extracted twice with ethyl acetate, the combined organic phases dried by sodium sulphate, filtered and concentrated. 229 g 7-dimethylaminomethyl-8-(6-methoxynaphthalen-2-yl)-1,4-dioxa-spiro[4.5]decan-8-ole were obtained.

229 g 7-dimethylaminomethyl-8-(6-methoxynaphthalen-2-yl)-1,4-dioxa-spiro[4.5]decan-8-ol were dissolved in 1,150 ml THF, 164 ml water and 41 ml concentrated hydrochloric acid added, the mixture stirred for five hours, neutralised with 32 mass percent sodium hydroxide solution, extracted twice with ethyl acetate/THF (V/V=1:1), the combined organic phases washed twice with saturated sodium chloride solution, dried by magnesium sulphate, filtered and concentrated. 400 ml methanol and 600 ml diisopropylether were added to the crude product obtained (196 g) the mixture filtered, the filtrate concentrated, dissolved in 1,600 ml 2-butanone and the hydrochloride precipitated by adding water and chlorotrimethylsilane in the same way as in AAV 1. 106 g of hydrochloride of 3-dimethylaminomethyl-4-hydroxy-4-(6-methoxynaphthalen-2-yl)cyclohexanone were obtained.

4.3 g sodium tetrahydridoborate were introduced into 82 ml ethanol p.a., 82.2 g 3-dimethyl-minomethyl-4-hydroxy-4-(6-methoxynaphthalen-2-yl)cyclohexanone, dissolved in 330 ml ethanol p.a., added dropwise with ice cooling, and stirred for 1 hour. For working up, initially 44 ml concentrated hydrochloric acid, then 40 ml 32 mass percent sodium hydroxide solution were added with ice cooling, the mixture extract twice with dichloromethane, the combined organic phases dried by magnesium sulphate, filtered and concentrated. 77.4 g of the hydrochloride of 2-dimethylaminomethyl-1-(6-methoxynaphthalen-2-yl)cyclohexane-1,4-diol were obtained from the crude product obtained (88.2 g) in the same way as in AAV 1.

Example 353

Butyric Acid 3-dimethylaminomethyl-4-hydroxy-4-(6-methoxynaphthalen-2-yl)cyclohexyl Ester Hydrochloride 70.0 g 2-dimethylaminomethyl-1-(6-methoxynaphthalen-2-yl)cyclohexane-1,4-diol were suspended in 560 ml THF p.a., 44.0 g potassium-tert.-butylate added in portions, the mixture stirred for 20 minutes, 21.0 ml butyryl chloride added dropwise, the mixture stirred for a further 20 minutes and a further 21.0 g potassium-tert.-butylate and 20.0 ml butyryl chloride respectively added again twice in accordance with the above model. For working up, 290 ml water were added with ice bath cooling, the phases separated, the mixture extracted once with ethyl acetate, the combined organic phases washed with 1 M sodium hydrogen carbonate solution, dried by magnesium sulphate, filtered and concentrated. 47.1 g of the hydrochloride of butyric acid 3-dimethylaminomethyl-4-hydroxy-4-(6-methoxynaphthalen-2-yl)cyclohexyl ester were obtained from the crude product obtained (90 g) in the same way as in AAV 1.

Example 331

4-benzyloxy-2-dimethylaminomethyl-1-(6-methoxynaphthalen-2-yl)cyclohexanol Hydrochloride The corresponding Grignard reagent was produced in 11 ml THF p.a. from 0.28 g magnesium and 2.72 g 2-bromo-6-methoxynaphthalene, a solution of 2.00 g 4-benzyloxy-2-dimethylaminomethylcyclohexanone in 8 ml THF p.a. added dropwise with ice cooling, and the mixture stirred for 1 hour. For working up, 4 ml 4 M ammonium chloride solution were added to the ice bath, the organic phase separated off, the aqueous phase extracted twice with diethyl ether, the combined organic phases dried by sodium sulphate, filtered and concentrated. The crude product obtained (3.20 g) was chromatographed with ethyl acetate/methanol/hexane (V/V/V=1:1:1) on silica gel. 1.52 g 4-benzyloxy-2-dimethylaminomethyl-1-(6-methoxynaphthalen-2-yl)cyclohexanol were obtained and converted into the corresponding hydrochloride (1.32 g) in the same way as in AAV 1.

Example 330

6-(4-benzyloxy-2-dimethylaminomethyl-1-hydroxycyclohexyl)-naphthalen-2-ol Hydrochloride 200 g 6-bromonaphthalen-2-ol, 143 g imidazole and 151 g tert.-butylchlorodimethylsilane were dissolved in 1,000 ml dimethylformamide, stirred for two hours at ambient temperature, the solution largely concentrated (506 g), the residue dissolved in ethyl acetate and water, 1,500 ml saturated sodium chloride solution added, the phases separated, the aqueous phase extracted twice with ethyl acetate and the organic phases combined and concentrated. The crude product obtained was dissolved in boiling hexane and subsequently kept overnight at 4° C. After filtration, 158 g (6-bromonaphthalen-2-yloxy)-tert.-butyldimethylsilane were isolated. Repeated concentration of the mother liquor and recrystallisation from methanol yielded a further 54 g (6-bromonaphthalen-2-yloxy)-tert.-butyldimethylsilane.

3.87 g (6-bromonaphthalen-2-yloxy)-tert.-butyldimethylsilane were dissolved in 19 ml THF p.a., 6.0 ml 1.6 M butyl lithium solution in hexane added dropwise with dry ice cooling, briefly stirred, then a solution of 2.00 g 4-benzyloxy-2-dimethylaminomethylcyclohexanone in 20 ml THF p.a. added dropwise and stirred for 1 hour while slowly heating. For working up, 4 ml water were added to the ice bath, the organic phase separated, the aqueous phase extracted twice with diethyl ether, the combined organic phases dried by sodium sulphate, filtered and concentrated. The crude product obtained (5.00 g) was chromatographed with ethyl acetate/methanol (V/V=1:1) on silica gel. 2.20 g 6-(4-benzyloxy-2-dimethylaminomethyl-1-hydroxy-cyclohexyl)-naphthalen-2-ol were obtained and converted into the corresponding hydrochloride (1.33 g) in the same way as in AAV 1.

General Supplement to the Examples:

By way of supplement, the following further examples were produced by at least one of the above (basic) methods or AAVs:

| Example No.: | Compound name: |
|---|---|
| 354 | benzoic acid 4-hydroxy-3-(4-methyl-piperazin-1-ylmethyl)-4-naphthalen-2-yl-cyclohexyl ester; bis-hydrochloride |
| 355 | 2-chloro-benzoic acid 4-hydroxy-3-(4-methyl-piperazin-1-ylmethyl)-4-naphthalen-2-yl-cyclohexyl ester; bis-hydrochloride |
| 356 | 3-chloro-benzoic acid 4-hydroxy-3-(4-methyl-piperazin-1-ylmethyl)-4-naphthalen-2-yl-cyclohexyl ester; bis-hydrochloride |
| 357 | 4-chloro-benzoic acid 4-hydroxy-3-(4-methyl-piperazin-1-ylmethyl)-4-naphthalen-2-yl-cyclohexyl ester; bis-hydrochloride |
| 358 | 2-fluoro-benzoic acid 4-hydroxy-3-(4-methyl-piperazin-1-ylmethyl)-4-naphthalen-2-yl-cyclohexyl ester; bis-hydrochloride |
| 359 | 3-fluoro-benzoic acid 4-hydroxy-3-(4-methyl-piperazin-1-ylmethyl) 4-naphthalen-2-yl-cyclohexyl ester; bis-hydrochloride |
| 360 | 4-fluoro-benzoic acid 4-hydroxy-3-(4-methyl-piperazin-1-ylmethyl) 4-naphthalen-2-yl-cyclohexyl ester; bis-hydrochloride |
| 361 | 2-methyl-benzoic acid 4-hydroxy-3-(4-methyl-piperazin-1-ylmethyl) 4-naphthalen-2-yl-cyclohexyl ester; bis-hydrochloride |
| 362 | 3-methyl-benzoic acid 4-hydroxy-3-(4-methyl-piperazin-1-ylmethyl) 4-naphthalen-2-yl-cyclohexyl ester; bis-hydrochloride |
| 363 | 4-methyl-benzoic acid 4-hydroxy-3-(4-methyl-piperazin-1-ylmethyl) 4-naphthalen-2-yl-cyclohexyl ester; bis-hydrochloride |
| 364 | 2-methoxy-benzoic acid 4-hydroxy-3-(4-methyl-piperazin-1-ylmethyl)-4-naphthalen-2-yl-cyclohexyl ester; bis-hydrochloride |
| 365 | 3-methoxy-benzoic acid 4-hydroxy-3-(4-methyl-piperazin-1-ylmethyl)-4-naphthalen-2-yl-cyclohexyl ester; bis-hydrochloride |
| 366 | 4-methoxy-benzoic acid 4-hydroxy-3-(4-methyl-piperazin-1-ylmethyl)-4-naphthalen-2-yl-cyclohexyl ester; bis-hydrochloride |
| 367 | 2,6-dichloro-benzoic acid 4-hydroxy-3-(4-methyl-piperazin-1-ylmethyl)-4-naphthalen-2-yl-cyclohexyl ester; bis-hydrochloride |
| 368 | 2,6-difluoro-benzoic acid 4-hydroxy-3-(4-methyl-piperazin-1-ylmethyl)-4-naphthalen-2-yl-cyclohexyl ester; bis-hydrochloride |
| 369 | 2-chloro-5-fluoro-benzoic acid 4-hydroxy-3-(4-methyl-piperazin-1-ylmethyl)-4-naphthalen-2-yl-cyclohexyl ester; bis-hydrochloride |
| 370 | biphenyl-4-carboxylic acid 4-hydroxy-3-(4-methyl-piperazin-1-ylmethyl) 4-naphthalen-2-yl-cyclohexylester; bis-hydrochloride |
| 371 | 2-chloro-benzoic acid 4-hydroxy-4-(6-methoxy-naphthalen-2-yl)-3-(4-methyl-piperazin-1-ylmethyl)-cyclohexyl ester; bis-hydrochloride |
| 372 | 3-chloro-benzoic acid 4-hydroxy-4-(6-methoxy-naphthalen-2-yl)-3-(4-methyl-piperazin-1-ylmethyl)-cyclohexyl ester; bis-hydrochloride |
| 373 | 4-chloro-benzoic acid 4-hydroxy-4-(6-methoxy-naphthalen-2-yl)-3-(4-methyl-piperazin-1-ylmethyl)-cyclohexyl ester; bis-hydrochloride |
| 374 | 2-fluoro-benzoic acid 4-hydroxy-4-(6-methoxy-naphthalen-2-yl)-3-(4-methyl-piperazin-1-ylmethyl)-cyclohexyl ester; bis-hydrochloride |
| 375 | 3-fluoro-benzoic acid 4-hydroxy-4-(6-methoxy-naphthalen-2-yl)-3-(4-methyl-piperazin-1-ylmethyl)-cyclohexyl ester; bis-hydrochloride |
| 376 | 4-fluoro-benzoic acid 4-hydroxy-4-(6-methoxy-naphthalen-2-yl)-3-(4-methyl-piperazin-1-ylmethyl)-cyclohexyl ester; bis-hydrochloride |
| 377 | 2-methyl-benzoic acid 4-hydroxy-4-(6-methoxy-naphthalen-2-yl)-3-(4-methyl-piperazin-1-ylmethyl)-cyclohexyl ester; bis-hydrochloride |
| 378 | 3-methyl-benzoic acid 4-hydroxy-4-(6-methoxy-naphthalen-2-methyl-piperazin-1-ylmethyl)-cyclohexyl ester; bis-hydrochloride |
| 379 | 4-methyl-benzoic acid 4-hydroxy-4-(6-methoxy-naphthalen-2-yl)-3-(4-methyl-piperazin-1-ylmethyl)-cyclohexyl ester; bis-hydrochloride |
| 380 | 2-methoxy-benzoic acid 4-hydroxy-4-(6-methoxy-naphthalen-2-yl)-3-(4-methyl-piperazin-1-ylmethyl)-cyclohexyl ester; bis-hydrochloride |
| 381 | 3-methoxy-benzoic acid 4-hydroxy-4-(6-methoxy-naphthalen-2-yl)-3-(4-methyl-piperazin-1-ylmethyl)-cyclohexyl ester; bis-hydrochloride |
| 382 | 4-methoxy-benzoic acid 4-hydroxy-4-(6-methoxy-naphthalen-2-yl)-3-(4-methyl-piperazin-1-ylmethyl)-cyclohexyl ester; bis-hydrochloride |
| 383 | 2,6-dichloro-benzoic acid 4-hydroxy-4-(6-methoxy-naphthalen-2-yl)-3-(4-methyl-piperazin-1-ylmethyl)-cyclohexyl ester; bis-hydrochloride |
| 384 | 2,6-fluoro-benzoic acid 4-hydroxy-4-(6-methoxy-naphthalen-2-yl)-3-(4-methyl-piperazin-1-ylmethyl)-cyclohexyl ester; bis-hydrochloride |
| 385 | 2-chloro-6-fluoro-benzoic acid 4-hydroxy-4-(6-methoxy-naphthalen-2-yl)-3-(4-methyl-piperazin-1-ylmethyl)-cyclohexyl ester; bis-hydrochloride |
| 386 | biphenyl-4-carboxylic acid 4-hydroxy-4-(6-methoxy-naphthalen-2-yl)-3-(4-methyl-piperazin-1-ylmethyl)-cyclohexyl ester; bis-hydrochloride |
| 387 | 4-(2-chlorobenzyloxy)-2-(4-methyl-piperazin-1-ylmethyl)-1-naphthalen-2-yl-cyclohexanol; bis-hydrochloride |
| 388 | 4-(3-chlorobenzyloxy)-2-(4-methyl-piperazin-1-ylmethyl)-1-naphthalen-2-yl-cyclohexanol; bis-hydrochloride |
| 389 | 4-(4-chlorobenzyloxy)-2-(4-methyl-piperazin-1-ylmethyl)-1-naphthalen-2-yl-cyclohexanol; bis-hydrochloride |
| 390 | 4-(2-fluorobenzyloxy)-2-(4-methyl-piperazin-1-ylmethyl)-1-naphthalen 2-yl-cyclohexanol; bis-hydrochloride |
| 391 | 4-(3-fluorobenzyloxy)-2-(4-methyl-piperazin-1-ylmethyl)-1-naphthalen 2-yl-cyclohexanol; bis-hydrochloride |

-continued

| Example No.: | Compound name: |
|---|---|
| 392 | 4-(4-fluorobenzyloxy)-2-(4-methyl-piperazin-1-ylmethyl)-1-naphthalen 2-yl-cyclohexanol; bis-hydrochloride |
| 393 | 4-(2-methyl-benzyloxy)-2-(4-methyl-piperazin-1-ylmethyl)-1-naphthalen-2-yl-cyclohexanol; bis-hydrochloride |
| 394 | 4-(3-methyl-benzyloxy)-2-(4-methyl-piperazin-1-ylmethyl)-1-naphthalen-2-yl-cyclohexanol; bis-hydrochloride |
| 395 | 4-(4-methyl-benzyloxy)-2-(4-methyl-piperazin-1-ylmethyl)-1-naphthalen-2-yl-cyclohexanol; bis-hydrochloride |
| 396 | 4-(2-methoxy-benzyloxy)-2-(4-methyl-piperazin-1-ylmethyl)-1-naphthalen-2-yl-cyclohexanol; bis-hydrochloride |
| 397 | 4-(3-methoxy-benzyloxy)-2-(4-methyl-piperazin-1-ylmethyl)-1-naphthalen-2-yl-cyclohexanol; bis-hydrochloride |
| 398 | 4-(4-methoxy-benzyloxy)-2-(4-methyl-piperazin-1-ylmethyl)-1-naphthalen-2-yl-cyclohexanol; bis-hydrochloride |
| 399 | 4-(2,6-dichlorobenzyl)-2-(4-methyl-piperazin-1-ylmethyl)-1-naphthalen-2-yl-cyclohexanol, bis-hydrochloride |
| 400 | 4-(2,6-difluorobenzyloxy)-2-(4-methyl-piperazin-1-ylmethyl)-1-naphthalen-2-yl-cyclohexanol, bis-hydrochloride |
| 401 | 4-(2-chloro-6-fluorobenzyloxy)-2-(4-methyl-piperazin-1-ylmethyl)-1-naphthalen-2-yl-cyclohexanol, bis-hydrochloride |
| 402 | 4-(2-chlorobenzyloxy)-1-(6-methoxy-naphthalen-2-yl)-2-(4-methyl piperazin-1-ylmethyl)-cyclohexanol; bis-hydrochloride |
| 403 | 4-(3-chlorobenzyloxy)-1-(6-methoxy-naphthalen-2-yl)-2-(4-methyl piperazin-1-ylmethyl)-cyclohexanol; bis-hydrochloride |
| 404 | 4-(4-chlorobenzyloxy)-1-(6-methoxy-naphthalen-2-yl)-2-(4-methyl piperazin-1-ylmethyl)-cyclohexanol; bis-hydrochloride |
| 405 | 4-(2-fluorobenzyloxy)-1-(6-methoxy-naphthalen-2-yl)-2-(4-methyl piperazin-1-ylmethyl)-cyclohexanol; bis-hydrochloride |
| 406 | 4-(3-fluorobenzyloxy)-1-(6-methoxy-naphthalen-2-yl)-2-(4-methyl piperazin-1-ylmethyl)-cyclohexanol; bis-hydrochloride |
| 407 | 4-(4-fluorobenzyloxy)-1-(6-methoxy-naphthalen-2-yl)-2-(4-methyl piperazin-1-ylmethyl)-cyclohexanol; bis-hydrochloride |
| 408 | 4-(2-methyl-benzyloxy)-1-(6-methoxy-naphthalen-2-yl)-2-(4-methyl piperazin-1-ylmethyl)-cyclohexanol; bis-hydrochloride |
| 409 | 4-(3-methyl-benzyloxy)-1-(6-methoxy-naphthalen-2-yl)-2-(4-methyl piperazin-1-ylmethyl)-cyclohexanol; bis-hydrochloride |
| 410 | 4-(4-methyl-benzyloxy)-1-(6-methoxy-naphthalen-2-yl)-2-(4-methyl piperazin-1-ylmethyl)-cyclohexanol; bis-hydrochloride |
| 411 | 4-(2-methoxy-benzyloxy)-1-(6-methoxy-naphthalen-2-yl)-2-(4-methyl piperazin-1-ylmethyl)-cyclohexanol; bis-hydrochloride |
| 412 | 4-(3-methoxy-benzyloxy)-1-(6-methoxy-naphthalen-2-yl)-2-(4-methyl piperazin-1-ylmethyl)-cyclohexanol; bis-hydrochloride |
| 413 | 4-(4-methoxy-benzyloxy)-1-(6-methoxy-naphthalen-2-yl)-2-(4-methyl piperazin-1-ylmethyl)-cyclohexanol; bis-hydrochloride |
| 414 | 4-(2,6-dichlorobenzyloxy)-1-(6-methoxy-naphthalen-2-yl)-2-(4-methyl piperazin-1-ylmethyl)-cyclohexanol; bis-hydrochloride |
| 415 | 4-(2,6-difluorobenzyloxy)-1-(6-methoxy-naphthalen-2-yl)-2-(4-methyl piperazin-1-ylmethyl)-cyclohexanol; bis-hydrochloride |
| 416 | 4-(2-chloro-6-fluorobenzyloxy)-1-(6-methoxy-naphthalen-2-yl)-2-(4 methyl-piperazin-1-ylmethyl)-cyclohexanol; bis-hydrochloride |
| 417 | 2-dimethylaminomethyl-4-(4-fluorobenzyloxy)-1-naphthalen-2-yl cyclohexanol |
| 418 | 4-fluoro-benzoic acid 3-dimethylaminomethyl-4-hydroxy-4-(6 methoxy-naphthalen-2-yl)-cyclohexylester |
| 419 | 4-fluoro-benzoic acid 3-dimethylaminomethyl-4-hydroxy-4 naphthalen-2-yl-cyclohexylester |
| 420 | 2-dimethylaminomethyl-4-(4-fluorobenzyloxy)-1-(6-methoxy naphthalen-2-yl)-cyclohexanol |
| 421 | 6-[2-dimethylaminomethyl-4-(4-fluorobenzyloxy)-1-hydroxy cyclohexyl)-naphthalen-2-ol |

What is claimed is:
1. A compound of formula I,

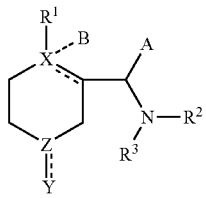

wherein
- A is H; or singly or multiply substituted or unsubstituted aryl or heteroaryl;
- $R^1$ is saturated or unsaturated, branched or unbranched, $C_{1-10}$ alkyl or $C_{3-10}$ cycloalkyl; aryl; heteroaryl; aryl bound by $C_{1-3}$ alkyl or $C_{1-3}$ alkylene or $C_{1-3}$ ethinyl; $C_{3-10}$ cycloalkyl bound by $C_{1-3}$ alkyl or $C_{1-3}$ alkylene or $C_{1-3}$ ethinyl; or heteroaryl bound by $C_{1-3}$ alkyl or $C_{1-3}$ alkylene or $C_{1-3}$ ethinyl, wherein $R^1$ is unsubstituted, or singly or independently multiply substituted by F, Cl, Br, I, $OR^{18}$, $SR^{18}$, $SO_2R^{18}$, $SO_2OR^{18}$, CN, $COOR^{18}$, $NR^{19}R^{20}$;
  unsubstituted or singly or multiply substituted $C_{1-10}$ alkyl, $C_{3-10}$ cycloalkyl or silyl; unsubstituted or singly or multiply substituted aryl or heteroaryl; and unsubstituted or singly or multiply substituted aryl bound by saturated or unsaturated $C_{1-3}$ alkyl, $C_{1-3}$ alkylene, $C_{3-10}$ cycloalkyl or heteroaryl;

wherein
- $R^{18}$ is H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl, $C_{3-10}$ cycloalkyl or heteroaryl bound by C1-3 alkyl, C1-3 alkylene; and
- $R^{19}$ and $R^{20}$ independently of one another are H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by C1-3 alkyl, C1-3 alkylene, $C_{3-10}$ cycloalkyl or heteroaryl; or
- $R^{19}$ and $R^{20}$ together form $CH_2CH_2OCH_2CH_2$, $CH_2CH_2NR^{21}CH_2CH_2$ or $(CH_2)_{3-6}$,
  wherein $R^{21}$ is H; unsubstituted or substituted phenyl; or saturated or unsaturated, branched or unbranched, unsubstituted or singly or multiply substituted $C_{1-10}$ alkyl;
- $R^2$ and $R^3$ independently of one another are H; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl; or
- $R^2$ and $R^3$ together represent $CH_2CH_2OCH_2CH_2$, $CH_2CH_2NR^6CH_2CH_2$ or $(CH_2)_{3-6}$, wherein $R^6$ is H; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl;

X has such a meaning that partial formula Ia:

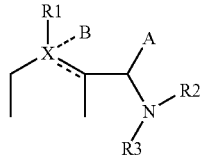

partial formula Ia
which is a part of formula I, is

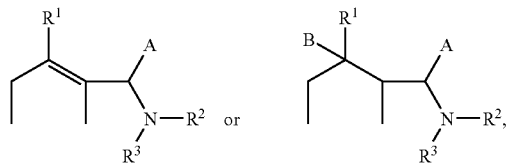

wherein B is OH, $OR^7$, H, F, Cl or $NR^8R^9$,
wherein $R^7$ is saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl; and $R^8$ and $R^9$ independently of one another are H; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by C1-3 alkyl, C1-3 alkylene, $C_{3-10}$ cycloalkyl or heteroaryl; or $R^8$ and $R^9$ together form $CH_2CH_2OCH_2CH_2$, $CH_2CH_2NR^{10}CH_2CH_2$ or $(CH_2)_{3-6}$,
wherein $R^{10}$ is H; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, and formula Ib,

formula Ib
which is also part of formula I, is

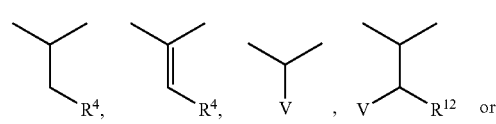

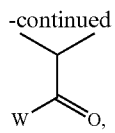

wherein $R^4$ is H, $COR^5$, $SO_2R^5$; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, wherein $R^5$ is saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl $C_{1-3}$ alkylene, $C_{3-10}$ cycloalkyl or heteroaryl, wherein V is $OR^4$ or $NR^4R^{11}$, and wherein W is $R^{11}$, $OR^{12}$ or $NR^{11}R^{12}$, wherein $R^{11}$ and $R^{12}$ independently of one another are H; saturated or unsaturated, branched or unbranched, singly or multiply substituted or unsubstituted $C_{7-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, wherein the compound is in the form of a racemate, a pure stereoisomer, a mixture of stereoisomers in any mixing ratio, in the illustrated form or in the form of its acid, base or a salt, or in the form of a solvate, provided that the following compounds are excluded, in which A is hydrogen, $R^1$ is a phenyl ring O- or S-substituted singly in the 3 position, $R^2$ and $R^3$ are both methyl, partial formula Ia is:

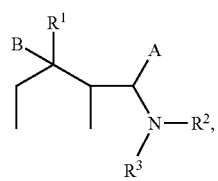

wherein B is OH, and
partial formula Ib is

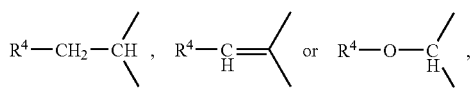

wherein $R^4$ is $C_{1-6}$ alkyl, $C_{2-6}$ alkenyl, $C_{5-7}$ cycloalkyl methyl, substituted or unsubstituted phenyl or substituted or unsubstituted benzyl, or in which $R^2$, $R^3$ independently of one another are H; branched or unbranched, singly or multiply substituted or unsubstituted, saturated or unsaturated $C_1$-$C_{10}$ alkyl; saturated or unsaturated, singly or multiply substituted or unsubstituted $C_3$-$C_7$ cycloalkyl or $C_3$-$C_7$ heterocycle in which a carbon atom is replaced by N, S or O in the ring; saturated or unsaturated, singly or multiply substituted or unsubstituted alkylaryl or alkylheteroaryl; or singly or multiply substituted or unsubstituted aryl or heteroaryl; or $R^2$ and $R^3$ together form a ring and represent $CH_2CH_2OCH_2CH_2$, $CH_2CH_2NR^6CH_2CH_2$ or $(CH_2)_{3-6}$;

partial formula Ia is

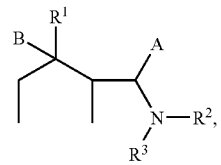

wherein A is hydrogen, $R^1$ is an unsubstituted or singly or doubly substituted phenyl ring, B is H, F, Cl, OH or $OR^7$, wherein $R^7$ is branched or unbranched, singly or multiply substituted or unsubstituted, saturated or unsaturated $C_1$-$C_{10}$ alkyl; singly or multiply substituted or unsubstituted saturated or unsaturated $C_3$-$C_7$ cycloalkyl or a $C_3$-$C_7$ heterocycle, in which a carbon atom is replaced in the ring by N, S or O; saturated or unsaturated, singly or multiply substituted or unsubstituted alkylaryl or alkylheteroaryl; or singly or multiply substituted or unsubstituted aryl or heteroaryl;

and partial formula Ib is

wherein V is $OR^4$ wherein $R^4$ is $COR^5$ and wherein $R^5$ is unsubstituted or singly or multiply substituted $C_{1-6}$ alkyl.

2. A pure enantiomer or a pure diastereomer of a compound according to claim 1.

3. A mixture of enantiomers, or a mixture of diastereomers, in any mixing ratio, of a compound according to claim 1.

4. A physiologically acceptable salt or a hydrate of a compound according to claim 1.

5. A compound according to claim 1, wherein $R^1$ is not a phenyl ring singly O- or S-substituted in the 3 position.

6. A compound according to claim 1, wherein $R^1$ is saturated or unsaturated, branched or unbranched, singly or multiply substituted or unsubstituted $C_{1-10}$ alkyl or $C_{3-10}$ cycloalkyl; naphthyl, heteroaryl, aryl bound by $C_{1-3}$ alkyl, $C_{1-3}$ alkylene or $C_{1-3}$ ethinyl; or $C_{3-10}$ cycloalkyl, bound by $C_{1-3}$ alkyl, $C_{1-3}$ alkylene or $C_{1-3}$ ethinyl, or heteroaryl bound by $C_{1-3}$ alkyl, or $C_{1-3}$ alkylene or $C_{1-3}$ ethinyl, wherein substitution on $R^1$ is by one or more radicals the group consisting of F, Cl, Br, I, $OR^{18}$, $SR^{18}$, $SO_2R^{18}$, $SO_2OR^{18}$, CN, $COOR^{18}$, $NR^{19}R^{20}$;

unsubstituted or singly or multiply substituted $C_{1-10}$ alkyl, $C_{3-10}$ cycloalkyl;

unsubstituted or singly or multiply substituted aryl or heteroaryl; and unsubstituted or singly or multiply substituted aryl bound by $C_{1-3}$ alkyl or $C_{1-3}$ alkylene, $C_{3-10}$ cycloalkyl, or heteroaryl; or $R^1$ corresponds to formula II

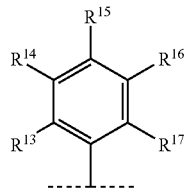

wherein $R^{13}$, $R^{15}$ and $R^{17}$ independently of one another are H, F, Cl, Br, I, $OR^{18}$, $SR^{18}$, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-10}$ cycloalkyl, or heteroaryl; and $R^{14}$ and $R^{16}$ independently of one another are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{1-10}$ cycloalkyl, or heteroaryl;

$R^{13}$ and $R^{14}$ together form $OCH_2O$, $OCH_2CH_2O$, $CH=CHO$, $CH=C(CH_3)O$ or $CH=CHNH$, and $R^{15}$-$R^{17}$ have the meaning given above, or $R^{14}$ and $R^{15}$ together form $OCH_2O$, $OCH_2CH_2O$, $CH=CHO$, $CH=C(CH_3)O$ or $CH=CHNH$, and $R^{13}$, $R^{16}$ and $R^{17}$ have the meaning given above, wherein $R^{18}$ is H, saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or aryl bound by $C_{1-3}$ alkyl, $C_{1-3}$ alkylene, unsubstituted or singly or multiply substituted $C_{3-10}$ cycloalkyl, or heteroaryl; and $R^{19}$ and $R^{20}$ independently of one another are H, saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by C1-3 alkyl or $C_{1-3}$ alkylene, $C_{3-10}$ cycloalkyl, or heteroaryl; or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H, saturated or unsaturated, branched or unbranched, unsubstituted or singly or multiply substituted $C_{1-10}$ alkyl.

7. A compound according to claim 6, wherein $R^1$ is $C_{1-6}$ alkyl, $C_{3-6}$ cycloalkyl; or a heteroaryl or aryl bound by $C_{3-6}$ cycloalkyl.

8. A compound according to claim 6, wherein substitution on $R^1$ is by one or more of $C_{1-6}$ alkyl, $C_{3-6}$ cycloalkyl, silyl, and aryl bound by $C_{3-6}$ cycloalkyl.

9. A compound according to claim 6, wherein $R^{13}$, $R^{15}$ and $R^{17}$ independently of one another are $C_{1-6}$ alkyl, $C_{3-6}$ cycloalkyl, silyl, or aryl bound by $C_{3-6}$ cycloalkyl.

10. A compound according to claim 6, wherein $R^{14}$, and $R^{16}$ independently of one another are $C_{1-6}$ alkyl, $C_{3-6}$ cycloalkyl, silyl, or aryl bound by $C_{3-6}$ cycloalkyl.

11. A compound according to claim 6, wherein $R^{19}$ and $R^{20}$ are $C_{1-6}$ alkyl, $C_{3-6}$ cycloalkyl, silyl, or aryl bound by $C_{3-6}$ cycloalkyl.

12. A compound according to claim 6, wherein $R^{21}$ is $C_{1-6}$ alkyl.

13. A compound according to claim 1, wherein $R^1$ is saturated or unsaturated, branched or unbranched, singly or multiply substituted or unsubstituted $C_{1-10}$ alkyl or $C_{3-10}$ cycloalkyl; unsubstituted or singly or multiply substituted naphthyl, heteroaryl, $C_{3-10}$ cycloalkyl, bound by $C_{1-3}$ alkyl, $C_{1-3}$ alkylene, $C_{1-3}$ ethinyl, and wherein substitution on $R^1$ is by one ore more of F, Cl, Br, I, $OR^{18}$, $SR^{18}$, $SO_2R^{18}$, $SO_2OR^{18}$, CN, $COOR^{18}$, $NR^{19}R^{20}$; unsubstituted or singly or multiply substituted $C_{1-10}$ alkyl, $C_{1-10}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{3-10}$ cycloalkyl, or heteroaryl.

14. A compound according to claim 13, wherein substitution on $R^1$ is by one or more of $C_{1-6}$ alkyl, $C_{3-6}$ cycloalkyl, silyl, and aryl bound by $C_{3-6}$ cycloalkyl.

15. A compound according to claim 6,
wherein $R^1$ corresponds formula II,
wherein $R^{13}$, $R^{15}$ and $R^{17}$ independently of one another are H, F, Cl, Br, I, $OR^{18}$, $SR^{18}$, $SO_2R^{18}$, $SO_2R^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-10}$ cycloalkyl, or heteroaryl;

wherein $R^{14}$ and $R^{16}$ independently of one another are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-10}$ alkyl, $C_{3-10}$ cycloalkyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-10}$ cycloalkyl, $C_{3-6}$ cycloalkyl or heteroaryl; or $R^{13}$ and $R^{14}$ together form $OCH_2O$, $OCH_2CH_2O$, $CH=CHO$, $CH=C(CH_3)O$ or $CH=CHNH$ and $R^{15}$-$R^{17}$ have the meaning given above, or $R^{14}$ and $R^{15}$ together form $OCH_2O$, $OCH_2CH_2O$, $CH=CHO$, $CH=C(CH_3)O$ or $CH=CHNH$ and $R^{13}$, $R^{16}$ and $R^{17}$ have the meaning given above, wherein $R^{18}$ is H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by $C_{1-3}$ alkyl or $C_{1-3}$ alkylene, $C_{3-10}$ cycloalkyl, or heteroaryl;

wherein $R^{19}$ and $R^{20}$ independently of one another are H, saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by $C_{1-3}$ alkyl, or $C_{1-3}$ alkylene, $C_{3-10}$ cycloalkyl, or heteroaryl; or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H, $C_{1-10}$ alkyl, and wherein formula Ib is

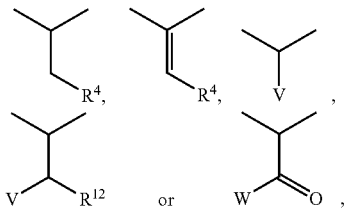

wherein $R^4$ is $COR^{5a}$, $SO_2R^5$; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, wherein $R^5$ is saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, wherein $R^{5a}$ is saturated or unsaturated, branched or unbranched, singly or multiply substituted or unsubstituted $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl, wherein V is $OR^4$ or $NR^4R^{11}$, and wherein W is $R^{11}$, $OR^{12}$ or $NR^{11}R^{12}$, wherein $R^{11}$ and $R^{12}$ independently of one another are H; saturated or unsaturated, branched or unbranched, singly or multiply substituted or unsubstituted $C_{7-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl.

16. A compound according to claim 15, wherein $R^{18}$ is $C_{1-6}$ alkyl or $C_{3-6}$ cycloalkyl.

17. A compound according to claim 15, wherein $R^{19}$ and $R^{20}$ independently of one another are $C_{1-6}$ alkyl, $C_{3-6}$ cycloalkyl, or unsubstituted or singly or multiply substituted aryl bound by $C_{3-6}$ cycloalkyl.

18. A compound according to claim 15, wherein $R^{21}$ is H, saturated or unsaturated, branched or unbranched, unsubstituted or singly or multiply substituted $C_{1-6}$ alkyl.

19. A compound according to claim 1, wherein partial formula Ia is

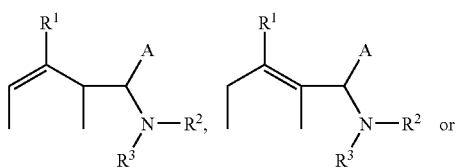

-continued

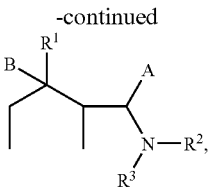

wherein B is OH, $OR^7$, H, F, Cl or $NR^8R^9$, wherein $R^7$ is saturated or unsaturated, branched or unbranched singly or multiply substituted or unsubstituted $C_{1-10}$ alkyl or $C_{3-10}$ cycloalkyl, singly or multiply substituted or unsubstituted aryl or heteroaryl, or singly or multiply substituted or unsubstituted aryl bound by $C_{1-3}$ alkyl, $C_{1-3}$ alkylene, $C_{3-10}$ cycloalkyl or heteroaryl; and $R^8$ and $R^9$ independently of one another are H; saturated or unsaturated, branched or unbranched, singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl or $C_{1-3}$ alkylene, $C_{3-10}$ cycloalkyl or heteroaryl; or $R^8$ and $R^9$ together form $CH_2CH_2OCH_2CH_2$, $CH_2CH_2NR^{10}CH_2CH_2$ or $(CH_2)_{3-6}$, wherein $R^{10}$ is H; saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl.

20. A compound according to claim 1, wherein A is singly or multiply substituted or unsubstituted aryl or heteroaryl.

21. A compound according to claim 1, wherein A is hydrogen.

22. A compound according to claim 1, wherein $R^2$ and $R^3$ independently of one another are H; saturated or unsaturated, branched or unbranched, singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl, or $R^2$ and $R^3$ together form $CH_2CH_2OCH_2CH_2$, $CH_2CH_2NR^6CH_2CH_2$ or $(CH_2)_{3-6}$, wherein $R^6$ is H; saturated or unsaturated, branched or unbranched, singly or multiply substituted or unsubstituted $C_{1-6}$ alkyl, or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl.

23. A compound according to claim 1, wherein $R^6$ is $CH_3$.

24. A compound according to claim 1, wherein $R^7$ is saturated or unsaturated, branched or unbranched singly or multiply substituted or unsubstituted $C_{1-6}$ alkyl, or $C_{3-6}$ cycloalkyl; singly or multiply substituted or unsubstituted aryl or heteroaryl; or singly or multiply substituted or unsubstituted aryl bound by C1-3 alkyl, C1-3 alkylene, $C_{3-6}$ cycloalkyl or heteroaryl.

25. A compound according to claim 1, wherein $R^8$ and $R^9$ independently of one another are H; saturated or unsaturated, branched or unbranched, singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl; or $R^2$ and $R^3$ together form $CH_2CH_2OCH_2CH_2$, $CH_2CH_2NR^{10}CH_2CH_2$ or $(CH_2)_{3-6}$, wherein $R^{10}$ is H; saturated or unsaturated, branched or unbranched singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl.

26. A compound according to claim 1, wherein $R^4$ is $COR^5$, $SO_2R^5$; saturated or unsaturated, branched or unbranched singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl, wherein $R^5$ is singly or multiply substituted or unsubstituted $C_{1-6}$ alkyl; singly or multiply substituted or unsubstituted aryl or heteroaryl; or singly or multiply substituted or unsubstituted aryl bound by $C_{1-3}$ alkyl, $C_{1-3}$ alkylene, or heteroaryl.

27. A compound according to claim 1, wherein $R^{11}$ and $R^{12}$ independently of one another are H; saturated or unsaturated, branched or unbranched singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl.

28. A compound according to claim 1, wherein $R^{13}$, $R^{15}$ and $R^{17}$ independently of one another are H, F, Cl, Br, I, $OR^{18}$, $SR^{18}$, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-6}$ alkyl, $C_{3-6}$ cycloalkyl or silyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-6}$ cycloalkyl or heteroaryl.

29. A compound according to claim 1, wherein $R^{14}$ and $R^{16}$ independently of one another are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-6}$ alkyl, $C_{3-6}$ cycloalkyl or silyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-6}$ cycloalkyl or heteroaryl; or $R^{13}$ and $R^{14}$ together form the group $OCH_2O$, $OCH_2CH_2O$, $CH=CHO$, $CH=C(CH_3)O$ or $CH=CHNH$, or $R^{14}$ and $R^{15}$ together form the group $OCH_2O$, $OCH_2CH_2O$, $CH=CHO$, $CH=C(CH_3)O$ or $CH=CHNH$ and $R^{13}$.

30. A compound according to claim 1, wherein $R^{18}$ is saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{1-3}$ ethinyl, $C_{3-6}$ cycloalkyl or heteroaryl.

31. A compound according to claim 1, wherein $R^{19}$ and $R^{20}$ independently of one another are H; saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{3-6}$ cycloalkyl or heteroaryl; or $R^{19}$ and $R^{20}$ together form $CH_2CH_2OCH_2CH_2$, $CH_2CH_2NR^{10}CH_2CH_2$ or $(CH_2)_{3-6}$.

32. A compound according to claim 1, wherein $R^{21}$ is H, or saturated or unsaturated, branched or unbranched, unsubstituted or singly or multiply substituted $C_{1-6}$ alkyl.

33. A compound according to claim 1, wherein $R^2$ and $R^3$ independently of one another are H; saturated or unsaturated, branched or unbranched, singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl, or $R^2$ and $R^3$ together form $CH_2CH_2OCH_2CH_2$, $CH_2CH_2NR^6CH_2CH_2$ or $(CH_2)_{3-6}$, wherein $R^6$ is H; saturated or unsaturated, branched or unbranched, singly or multiply substituted or unsubstituted $C_{1-6}$ alkyl, or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl; and $R^7$ is saturated or unsaturated, branched or unbranched singly or multiply substituted or unsubstituted $C_{1-6}$ alkyl, or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl; and $R^8$ and $R^9$ independently of one another are H; saturated or unsaturated, branched or unbranched, singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl; or $R^2$ and $R^3$ together form $CH_2CH_2OCH_2CH_2$, $CH_2CH_2NR^{10}CH_2CH_2$ or $(CH_2)_{3-6}$, wherein $R^{10}$ is H; saturated or unsaturated, branched or unbranched singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl, and $R^4$ is $COR^5$, $SO_2R^5$; saturated or unsaturated, branched or unbranched singly or multiply substituted or unsubstituted $C_{1-6}$ alkyl or $C_{3-6}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-6}$ cycloalkyl or heteroaryl, wherein $R^5$ is singly or multiply substituted or unsubstituted $C_{1-6}$ alkyl; singly or multiply substituted or unsubstituted aryl or heteroaryl; or singly or multiply substituted or unsubstituted aryl bound by $C_{1-3}$ alkyl, $C_{1-3}$ alkylene, or heteroaryl, and $R^{11}$ and $R^{12}$ independently of one another are H; saturated or unsaturated, branched or unbranched singly or multiply substituted or unsubstituted $C_{1-6}$ alkyl or $C_{3-6}$ cycloalkyl; singly or multiply substituted or unsubsti tuted aryl or heteroaryl; or singly or multiply substituted or unsubstituted aryl bound by $C_{1-3}$ alkyl, $C_{1-3}$ alkylene, $C_{3-6}$ cycloalkyl or heteroaryl; and $R^{13}$, $R^{15}$ and $R^{17}$ independently of one another are H, F, Cl, Br, I, $OR^{18}$, $SR^{18}$, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-6}$ alkyl, $C_{3-6}$ cycloalkyl or silyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-6}$ cycloalkyl or heteroaryl; and $R^{14}$ and $R^{16}$ independently of one another are H, F, Cl, Br, I, $SO_2R^{18}$, $SO_2OR^{18}$, CN, $COOR^{18}$, $NR^{19}R^{20}$; saturated or unsaturated, branched or unbranched, singly or multiply substituted or unsubstituted $C_{1-6}$ alkyl, $C_{3-6}$ cycloalkyl or silyl; singly or multiply substituted or unsubstituted aryl or heteroaryl; singly or multiply substituted or unsubstituted aryl bound by $C_{1-3}$ alkyl, $C_{1-3}$ alkylene, $C_{1-3}$ ethinyl, $C_{3-6}$ cycloalkyl or heteroaryl; or $R^{13}$ and $R^{14}$ together form the group $OCH_2O$, $OCH_2CH_2O$, $CH=CHO$, $CH=C(CH_3)O$ or $CH=CHNH$, and $R^{15}$, $R^{16}$ and $R^{17}$ have the meanings given above, or $R^{14}$ and $R^{15}$ together form the group $OCH_2O$, $OCH_2CH_2O$, $CH=CHO$, $CH=C(CH_3)O$ or $CH=CHNH$, and $R^{13}$, $R^{16}$ and $R^{17}$ have the meanings given above, or $R^{18}$ is saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{1-3}$ ethinyl, $C_{3-6}$ cycloalkyl or heteroaryl; and $R^{19}$ and $R^{20}$ independently of one another are H; saturated or unsaturated, branched or unbranched, unsubstituted or singly or multiply substituted $C_{1-6}$ alkyl or $C_{3-6}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{3-6}$ cycloalkyl or heteroaryl; or $R^{19}$ and $R^{20}$ together form $CH_2CH_2OCH_2CH_2$, $CH_2CH_2NR^{10}CH_2CH_2$ or $(CH_2)_{3-6}$, and $R^{21}$ is H, or saturated or unsaturated, branched or unbranched, unsubstituted or singly or multiply substituted $C_{1-6}$ alkyl.

34. A compound of claim 1, wherein A is hydrogen, or unsubstituted or singly or multiply substituted phenyl.

35. A compound of claim 1, wherein A is hydrogen.

36. A compound of claim 1, wherein $R^2$ and $R^3$ are independently of each other saturated or unsaturated, branched or unbranched, unsubstituted or singly or multiply substituted $C_{1-6}$ alkyl, or $R^2$ and $R^3$ together represent $CH_2CH_2NR^{10}CH_2CH_2$ or $(CH_2)_{3-6}$, wherein $R^6$ is H or saturated, branched or unbranched, and unsubstituted $C_{1-6}$ alkyl.

37. A compound according to claim 36, wherein at least one of $R^2$ and $R^3$ is $CH_3$.

38. A compound according to claim 37, wherein both $R^2$ and $R^3$ are $CH_3$.

39. A compound according to claim 36, wherein $R^6$ is H or $CH_3$.

40. A compound according to claim 1, wherein $R^1$ is saturated or unsaturated, branched or unbranched $C_{1-6}$ alkyl; $C_{3-6}$ cycloalkyl; naphthyl; phenyl; furyl; thiophenyl; naphthyl bound by $C_{1-3}$ alkylene or $C_{1-3}$ ethinyl; phenyl, $C_{3-6}$ cycloalkyl or thiophenyl bound by $C_{1-3}$ alkyl, $C_{1-3}$ alkylene, $C_{1-3}$ ethinyl or furyl.

41. A compound according to claim 1, wherein partial formula Ib is

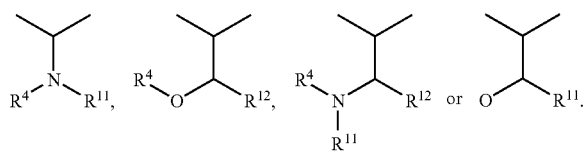

42. A compound according to claim 1, wherein $R^1$ is naphthyl or naphthyl bound by $C_{1-3}$ alkyl, alkylene or $C_{1-3}$ ethinyl, unsubstituted or singly or multiply substituted by at least one radical selected independently of one another from the group consisting of F, Cl, Br, I, $OR^{18}$, $SR^{18}$, $SO_2R^{18}$, $SO_2OR^{18}$, CN, $COOR^{18}$, $NR^{19}R^{20}$; unsubstituted or singly or multiply substituted $C_{1-10}$ alkyl, $C_{3-10}$ cycloalkyl or silyl; unsubstituted or singly or multiply substituted aryl or heteroaryl; and unsubstituted or singly or multiply substituted aryl bound by $C_{1-3}$ alkyl, $C_{1-3}$ alkylene, $C_{3-10}$ cycloalkyl or heteroaryl;

wherein $R^{18}$ is H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{3-10}$ cycloalkyl or heteroaryl;

$R^{19}$ and $R^{20}$ independently of one another are H; saturated or unsaturated, branched or unbranched, unsubstituted or singly or multiply substituted $C_{1-10}$ alkyl or $C_{3-10}$ cycloalkyl; unsubstituted or singly or multiply substituted aryl or heteroaryl; or unsubstituted or singly or multiply substituted aryl bound by $C_{1-3}$ alkyl, $C_{1-3}$ alkylene, $C_{3-10}$ cycloalkyl or heteroaryl; or $R^{19}$ and $R^{20}$ together form $CH_2CH_2OCH_2CH_2$, $CH_2CH_2NR^{21}CH_2CH_2$ or $(CH_2)_{3-6}$, wherein $R^{21}$ is H; saturated or unsaturated, branched or unbranched, unsubstituted or singly or multiply substituted $C_{1-10}$ alkyl;

$R^2$ and $R^3$ independently of one another are H; saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl; or $R^2$ and $R^3$ together represent $CH_2CH_2OCH_2CH_2$, $CH_2CH_2NR^6CH_2CH_2$ or $(CH_2)_{3-6}$, wherein $R^6$ is H; saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl;

partial formula Ia is

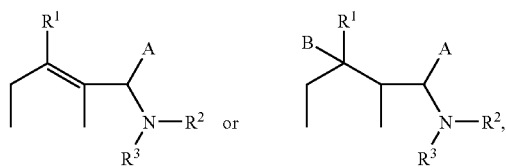

wherein B is OH, $OR^7$, H, F, Cl or $NR^8R^9$, wherein $R^7$ is saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl; and $R^8$ and $R^9$ independently of one another are H; saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl; or $R^8$ and $R^9$ together form $CH_2CH_2OCH_2CH_2$, $CH_2CH_2NR^{10}CH_2CH_2$ or $(CH_2)_{3-6}$, wherein $R^{10}$ is H; saturated or unsaturated, branched or unbranched singly or multiply substituted or unsubstituted $C_{1-10}$ alkyl or $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl;

partial formula Ib is

wherein V is $OR^4$, wherein $R^4$ is $COR^5$; saturated or unsaturated, branched or unbranched singly or multiply substituted or unsubstituted $C_{1-10}$ alkyl; saturated or unsaturated, singly or multiply substituted or unsubstituted $C_{3-10}$ cycloalkyl; singly or multiply substituted or unsubstituted aryl or heteroaryl; or singly or multiply substituted or unsubstituted aryl bound by $C_{1-3}$ alkyl, $C_{3-10}$ cycloalkyl or heteroaryl, wherein $R^5$ is saturated or unsaturated, branched or unbranched, singly or multiply substituted or unsubstituted $C_{1-10}$ alkyl; saturated or unsaturated, singly or multiply substituted or unsubstituted $C_{3-10}$ cycloalkyl; singly or multiply substituted or unsubstituted aryl or heteroaryl; or singly or multiply substituted or unsubstituted aryl bound by $C_{1-3}$ alkyl, $C_{1-3}$ alkylene, $C_{3-10}$ cycloalkyl or heteroaryl.

43. A compound according to claim 42, wherein A is H or singly or multiply substituted or unsubstituted phenyl.

44. A compound according to claim 43, wherein A is H.

45. A compound according to claim 42, wherein $R^1$ is naphthyl, unsubstituted or substituted by OH or $OCH_3$.

46. A compound according to claim 42, wherein one or both of $R^2$ and $R^3$ are $CH_3$, or $R^2$ and $R^3$ together represent together represent $CH_2CH_2NR^6CH_2CH_2$, wherein $R^6$ is H or $CH_3$.

47. A compound according to claim 42, wherein partial formula Ia is

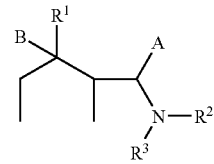

wherein B is OH.

48. A compound according to claim 42, wherein

A is H or singly or multiply substituted or unsubstituted phenyl; and $R^1$ is naphthyl, unsubstituted or singly or multiply substituted by at least one radical selected independently of one another from the group consisting of F, Cl, Br, I, $OR^{18}$; and branched or unbranched, unsubstituted or singly or multiply substituted $C_{1-4}$ alkyl;

wherein $R^{18}$ is H; branched or unbranched, unsubstituted or singly or multiply substituted $C_{1-4}$ alkyl; and $R^2$ and $R^3$ are saturated or unsaturated, branched or unbranched, unsubstituted or singly or multiply substituted $C_{1-6}$ alkyl, or $R^2$ and $R^3$ together represent $CH_2CH_2NR^6CH_2CH_2$ or $(CH_2)_{4-5}$, wherein $R^6$ is H or saturated, branched or unbranched, and unsubstituted $C_{1-6}$ alkyl; and partial formula Ia is

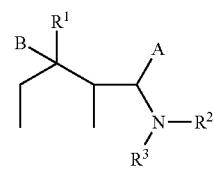

wherein B is OH, $OR^7$, H, F, or Cl, wherein $R^7$ is branched or unbranched, singly or multiply substituted or unsubstituted $C_{1-4}$ alkyl; and partial formula Ib is

wherein V is $OR^4$, wherein $R^4$ is $COR^5$; singly or multiply substituted or unsubstituted phenyl or benzyl; in particular $COR^5$ or singly or multiply substituted or unsubstituted benzyl;

wherein $R^5$ is saturated or unsaturated, branched or unbranched, singly or multiply substituted or unsubstituted $C_{1-10}$ alkyl, or singly or multiply substituted or unsubstituted phenyl.

49. A compound according to claim 42, wherein A is H, $R^1$ is naphthyl, unsubstituted or substituted by OH or $OCH_3$, at least one of $R^2$ and $R^3$ is $CH_3$; or $R^2$ and $R^3$ together represent $CH_2CH_2NR^6CH_2CH_2$, wherein $R^6$ is H or $CH_3$; and partial formula Ia is

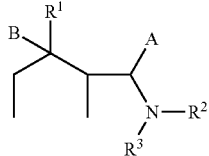

wherein B is OH.

50. A compound according to claim 1, selected from the group consisting of 4-benzyloxy-1-(4-bromophenyl)-2-dimethylaminomethyl-cyclohexanol;
4-benzyloxy-2-dimethylaminomethyl-1-(4-trifluoromethyl-phenyl)-cyclohexanol;
4-benzyloxy-1-(3,4-difluorophenyl)-2-dimethylaminomethyl-cyclohexanol;
4-benzyloxy-2-dimethylaminomethyl-1-(3-fluoro-4-methyl-phenyl)-cyclohexanol;
4-benzyloxy-1-(3,4-dichlorophenyl)-2-dimethylaminomethyl-cyclohexanol;
4-benzyloxy-2-dimethylaminomethyl-1-naphthalen-2-yl-cyclohexanol;
4-benzyloxy-2-dimethylaminomethyl-1-(3,4-dimethyl-phenyl)-cyclohexanol;
4-benzyloxy-2-dimethylaminomethyl-1-(4-fluoro-3-methyl-phenyl)-cyclohexanol;
4-benzyloxy-2-dimethylaminomethyl-1-(5-fluoro-2-methyl-phenyl)-cyclohexanol;
4-benzyloxy-1-(3-chloro-4-fluorophenyl)-2-dimethylaminomethyl-cyclohexanol;
4-benzyloxy-1-(5-chloro-2-methoxy-phenyl)-2-dimethylaminomethyl-cyclohexanol;
4-benzyloxy-1-(2-bromophenyl)-2-dimethylaminomethyl-cyclohexanol;
4-benzyloxy-2-dimethylaminomethyl-1-(2-methoxy-phenyl)-cyclohexanol;
4-benzyloxy-2-dimethylaminomethyl-1-(2-methylsulfanyl-phenyl)-cyclohexanol;
4-benzyloxy-1-(4-chlorophenyl)-2-dimethylaminomethyl-cyclohexanol;
4-benzyloxy-1-(3-bromophenyl)-2-dimethylaminomethyl-cyclohexanol;
4-benzyloxy-1-(4-bromo-3-fluorophenyl)-2-dimethylaminomethyl-cyclohexanol;
4-benzyloxy-2-dimethylaminomethyl-1-(4-methoxy-phenyl)-cyclohexanol;
4-benzyloxy-1-(2-chlorophenyl)-2-dimethylaminomethyl-cyclohexanol;
4-benzyloxy-2-dimethylaminomethyl-1-(3-trifluoromethyl-phenyl)-cyclohexanol;
4-benzyloxy-2-dimethylaminomethyl-1-(4-pentyl-phenyl)-cyclohexanol;
4-benzyloxy-2-dimethylaminomethyl-1-(2,5-dimethyl-phenyl)-cyclohexanol;
4-benzyloxy-2-dimethylaminomethyl-1-(4-isopropyl-phenyl)-cyclohexanol;
4-benzyloxy-2-dimethylaminomethyl-1-(2,3-dimethyl-phenyl)-cyclohexanol;
4-benzyloxy-2-dimethylaminomethyl-1-(3-fluorophenyl)-cyclohexanol;
4-benzyloxy-1-(3,5-bis-trifluoromethyl-phenyl)-2-dimethylaminomethyl-cyclohexanol;
4-benzyloxy-2-dimethylaminomethyl-1-(4-ethyl-phenyl)-cyclohexanol;
4-benzyloxy-1-(3,5-dichlorophenyl)-2-dimethylaminomethyl-cyclohexanol;
2-dimethylaminomethyl-4-(4-fluorobenzyloxy)-1-o-tolyl-cyclohexanol;
2-dimethylaminomethyl-4-(4-fluorobenzyloxy)-1-p-tolyl-cyclohexanol;
2-dimethylaminomethyl-1-(2,5-dimethyl-phenyl)-4-(4-fluorobenzyloxy)-cyclohexanol;
2-dimethylaminomethyl-1-(3,4-dimethyl-phenyl)-4-(4-fluorobenzyloxy)-cyclohexanol;
2-dimethylaminomethyl-1-(3,5-dimethyl-phenyl)-4-(4-fluorobenzyloxy)-cyclohexanol;
2-dimethylaminomethyl-4-(4-fluorobenzyloxy)-1-(4-isopropyl-phenyl)-cyclohexanol;
2-dimethylaminomethyl-4-(4-fluorobenzyloxy)-1-(3-fluorophenyl)-cyclohexanol;
2-dimethylaminomethyl-4-(4-fluorobenzyloxy)-1-(4-fluorophenyl)-cyclohexanol;
1-(3,4-difluorophenyl)-2-dimethylaminomethyl-4-(4-fluorobenzyloxy)-cyclohexanol;
2-dimethylaminomethyl-4-(4-fluorobenzyloxy)-1-(3-fluoro-4-methyl-phenyl)-cyclohexanol;
2-dimethylaminomethyl-4-(4-fluorobenzyloxy)-1-(4-fluoro-3-methyl-phenyl)-cyclohexanol;
1-(2-chlorophenyl)-2-dimethylaminomethyl-4-(4-fluorobenzyloxy)-cyclohexanol;
1-(3-chlorophenyl)-2-dimethylaminomethyl-4-(4-fluorobenzyloxy)-cyclohexanol;
1-(4-chlorophenyl)-2-dimethylaminomethyl-4-(4-fluorobenzyloxy)-cyclohexanol;
1-(3,4-dichlorophenyl)-2-dimethylaminomethyl-4-(4-fluorobenzyloxy)-cyclohexanol;
1-(4-chloro-3-fluorophenyl)-2-dimethylaminomethyl-4-(4-fluorobenzyloxy)-cyclohexanol;
1-(3,5-dichlorophenyl)-2-dimethylaminomethyl-4-(4-fluorobenzyloxy)-cyclohexanol;
1-(4-chloro-2-methoxy-phenyl)-2-dimethylaminomethyl-4-(4-fluorobenzyloxy)-cyclohexanol;
2-dimethylaminomethyl-4-(4-fluorobenzyloxy)-1-(4-trifluoromethyl-phenyl)-cyclohexanol;
1-(3,5-bis-trifluoromethyl-phenyl)-2-dimethylaminomethyl-4-(4-fluorobenzyloxy)-cyclohexanol;
2-dimethylaminomethyl-4-(4-fluorobenzyloxy)-1-(2-methoxy-phenyl)-cyclohexanol;
2-dimethylaminomethyl-4-(4-fluorobenzyloxy)-1-(2-methylsulfanyl-phenyl)-cyclohexanol;
3,4-dichloro-N-[3-dimethylaminomethyl-4-hydroxy-4-(3-methoxy-phenyl)-cyclohexyl]-benzamide;
naphthalene-2-carboxylic acid [3-dimethylaminomethyl-4-hydroxy-4-(3-methoxy phenyl)-cyclohexyl]-amide;
N-[3-dimethylaminomethyl-4-hydroxy-4-(3-methoxy-phenyl)-cyclohexyl]-3-phenyl-propionamide;
N-[3-dimethylaminomethyl-4-hydroxy-4-(3-methoxy-phenyl)-cyclohexyl]-4-nitro-benzamide;
N-[3-dimethylaminomethyl-4-hydroxy-4-(3-methoxy-phenyl)-cyclohexyl]-4-methyl-3-nitro-benzamide;
N-[3-dimethylaminomethyl-4-hydroxy-4-(3-methoxy-phenyl)-cyclohexyl]-3,4,5-trimethoxy-benzamide;
2-(4-chlorophenoxy)-N-[3-dimethylaminomethyl-4-hydroxy-4-(3-methoxy-phenyl)-cyclohexyl]-acetamide;
N[3-dimethylaminomethyl-4-hydroxy-4-(3-methoxy-phenyl)-cyclohexyl]-3-nitro-benzamide;

furan-2-carboxylic acid [3-dimethylaminomethyl-4-hydroxy-4-(3-methoxy-phenyl)-cyclohexyl]-amide;
1-(3,4-difluorophenyl)-2-dimethylaminomethyl-4-phenethyl-cyclohexanol;
2-dimethylaminomethyl-1-(2,3-dimethyl-phenyl)-4-phenethyl-cyclohexanol;
2-dimethylaminomethyl-1-naphthalen-1-yl-4-phenethyl-cyclohexanol;
1-(3,5-bis-trifluoromethyl-phenyl)-2-dimethylaminomethyl-4-phenethyl-cyclohexanol;
1-(3-bromophenyl)-2-dimethylaminomethyl-4-phenethyl-cyclohexanol;
2-dimethylaminomethyl-1-(4-fluoro-3-methyl-phenyl)-4-phenethyl-cyclohexanol;
2-dimethylaminomethyl-4-phenethyl-1-m-tolyl-cyclohexanol;
4-benzyl-2-dimethylaminomethyl-1-m-tolyl-cyclohexanol;
4-benzyl-1-(3,4-difluorophenyl)-2-dimethylaminomethyl-cyclohexanol;
4-benzyl-2-dimethylaminomethyl-1-p-tolyl-cyclohexanol;
2-dimethylaminomethyl-4-(3-methoxy-benzyl)-1-p-tolyl-cyclohexanol;
1-(4-chlorophenyl)-2-dimethylaminomethyl-4-(3-methoxy-benzyl)-cyclohexanol;
1-(4-bromo-3-fluorophenyl)-2-dimethylaminomethyl-4-(3-methoxy-benzyl)-cyclohexanol;
2-dimethylaminomethyl-4-(4-fluorobenzyl)-1-p-tolyl-cyclohexanol;
1-(4-chlorophenyl)-2-dimethylaminomethyl-4-(4-fluorobenzyl)-cyclohexanol;
[2-(3,5-bis-trifluoromethyl-phenyl)-5-phenethyl-cyclohex-1-enylmethyl]-dimethylamine;
dimethyl-(5-phenethyl-2-p-tolyl-cyclohex-1-enylmethyl)-amine;
[2-(3-chloro-4-fluorophenyl)-5-phenethyl-cyclohex-1-enylmethyl]-dimethyl-amine;
[2-(2,5-dimethyl-phenyl)-5-phenethyl-cyclohex-1-enylmethyl]-dimethyl-amine;
[2-(3-chloro-4-fluorophenyl)-2-fluoro5-phenethyl-cyclohexylmethyl]-dimethyl-amine;
[2-fluoro-5-(4-fluorobenzyl)-2-p-tolyl-cyclohexylmethyl]-dimethyl-amine;
benzyl-2-(dimethylamino-phenyl-methyl)-4-phenyl-cyclohexanol;
2-(dimethylamino-phenyl-methyl)-4-phenyl-1-vinyl-cyclohexanol;
N-[3-dimethylaminomethyl-4-hydroxy-4-(3-methoxy-phenyl)-cyclohexyl]-2-phenoxy-acetamide;
N-[3-dimethylaminomethyl-4-hydroxy-4-(3-methoxy-phenyl)-cyclohexyl]-4-trifluoromethyl-benzamide;
N-[3-dimethylaminomethyl-4-hydroxy-4-(3-methoxy-phenyl)-cyclohexyl]-4-methoxy-benzamide;
2-dimethylaminomethyl-1-(4-fluorophenyl)-4-phenethyl-cyclohexanol;
1-(4-bromophenyl)-2-dimethylaminomethyl-4-phenethyl-cyclohexanol;
2-dimethylaminomethyl-1-(4-ethyl-phenyl)-4-phenethyl-cyclohexanol;
2-dimethylaminomethyl-1-(4-isopropyl-phenyl)-4-phenethyl-cyclohexanol;
2-dimethylaminomethyl-1-(4-methoxy-phenyl)-4-phenethyl-cyclohexanol;
2-dimethylaminomethyl-1-(2,4-dimethyl-phenyl)-4-phenethyl-cyclohexanol;
2-dimethylaminomethyl-1-(2-methylsulfanyl-phenyl)-4-phenethyl-cyclohexanol;
2-dimethylaminomethyl-1-(5-fluoro-2-methyl-phenyl)-4-phenethyl-cyclohexanol;
2-dimethylaminomethyl-1-(2,5-dimethyl-phenyl)-4-phenethyl-cyclohexanol;
2-dimethylaminomethyl-4-phenethyl-1-p-tolyl-cyclohexanol;
2-dimethylaminomethyl-1-(3-fluorophenyl)-4-phenethyl-cyclohexanol;
1-(3-chlorophenyl)-2-dimethylaminomethyl-4-phenethyl-cyclohexanol;
1-(4-chloro-3-fluorophenyl)-2-dimethylaminomethyl-4-phenethyl-cyclohexanol;
2-dimethylaminomethyl-4-phenethyl-1-(3-trifluoromethyl-phenyl)-cyclohexanol;
1-(3,5-dichlorophenyl)-2-dimethylaminomethyl-4-phenethyl-cyclohexanol;
2-dimethylaminomethyl-1-(3,4-dimethyl-phenyl)-4-phenethyl-cyclohexanol;
1-(3,4-dichlorophenyl)-2-dimethylaminomethyl-4-phenethyl-cyclohexanol;
1-(4-chlorophenyl)-2-dimethylaminomethyl-4-phenethyl-cyclohexanol;
2-dimethylaminomethyl-1-(3-fluoro-4-methyl-phenyl)-4-phenethyl-cyclohexanol;
2-dimethylaminomethyl-1-(3,5-dimethyl-phenyl)-4-phenethyl-cyclohexanol;
1-(4-bromo-3-fluorophenyl)-2-dimethylaminomethyl-4-phenethyl-cyclohexanol;
1-(4-tert-butyl-phenyl)-2-(dimethylamino-phenyl-methyl)-4-phenyl-cyclohexanol;
2-(dimethylamino-phenyl-methyl)-4-phenyl-1-m-tolyl-cyclohexanol;
2-(dimethylamino-phenyl-methyl)-1-phenethyl-4-phenyl-cyclohexanol;
2-(dimethylamino-phenyl-methyl)-4-phenyl-1-phenylethynyl-cyclohexanol;
2-(dimethylamino-phenyl-methyl)-1-(3-methoxy-phenyl)-4-phenyl-cyclohexanol;
2-(dimethylamino-phenyl-methyl)-4-phenyl-1-(3-phenyl-propyl)-cyclohexanol;
2-(dimethylamino-phenyl-methyl)-1-(4-methoxy-phenyl)-4-phenyl-cyclohexanol;
2-(dimethylamino-phenyl-methyl)-1-(2-methoxy-phenyl)-4-phenyl-cyclohexanol;
4-benzyloxy-2-dimethylaminomethyl-1-phenyl-cyclohexanol;
1-benzyl-4-benzyloxy-2-dimethylaminomethyl-cyclohexanol;
4-benzyloxy-2-dimethylaminomethyl-1-(4-fluoro-3-methyl-phenyl)-cyclohexanol;
4-benzyloxy-2-dimethylaminomethyl-1-o-tolyl-cyclohexanol;
4-benzyloxy-2-dimethylaminomethyl-1-vinyl-cyclohexanol;
4-benzyloxy-1-cyclopentyl-2-dimethylaminomethyl-cyclohexanol;
4-benzyloxy-2-dimethylaminomethyl-1-m-tolyl-cyclohexanol;
4-benzyloxy-2-dimethylaminomethyl-bicyclohexyl-1-ol;
4-benzyloxy-2-dimethylaminomethyl-1-(4-fluorophenyl)-cyclohexanol;
4-benzyloxy-2-dimethylaminomethyl-1-phenylethynyl-cyclohexanol;
4-benzyloxy-2-dimethylaminomethyl-1-thiophen-2-yl-cyclohexanol;

4-benzyloxy-2-dimethylaminomethyl-1-(3-methoxy-phenyl)-cyclohexanol;
4-benzyloxy-2-dimethylaminomethyl-1-(3-phenyl-propyl)-cyclohexanol;
4-benzyloxy-2-dimethylaminomethyl-1-p-tolyl-cyclohexanol;
4-benzyloxy-2-dimethylaminomethyl-1-(4-methoxy-phenyl)-cyclohexanol;
4-benzyloxy-2-dimethylaminomethyl-1-(3-fluorophenyl)-cyclohexanol;
4-benzyloxy-1-(3-chlorophenyl)-2-dimethylaminomethyl-cyclohexanol;
4-benzyloxy-2-dimethylaminomethyl-1-(3-methoxy-benzyl)-cyclohexanol;
4-benzyloxy-1-(4-chloro-3-trifluoromethyl-phenyl)-2-dimethylaminomethyl-cyclohexanol;
4-benzyloxy-2-dimethylaminomethyl-1-(3-fluorobenzyl)-cyclohexanol;
4-benzyloxy-2-dimethylaminomethyl-1-(2-methyl-benzyl)-cyclohexanol;
4-benzyloxy-2-dimethylaminomethyl-1-(2,5-dimethyl-benzyl)-cyclohexanol;
4-(4-chlorobenzyl)-2-dimethylaminomethyl-1-(3-methoxy-phenyl)-cyclohexanol;
4-(4-chlorobenzyl)-2-dimethylaminomethyl-1-(3-phenyl-propyl)-cyclohexanol;
4-(4-chlorobenzyl)-1-(2,3-dichlorophenyl)-2-dimethylaminomethyl-cyclohexanol;
4-(4-chlorobenzyl)-1-cyclohexylmethyl-2-dimethylaminomethyl-cyclohexanol;
4-(4-chlorobenzyl)-2-dimethylaminomethyl-1-(5-fluoro-2-methoxy-phenyl)-cyclohexanol;
4-(4-chlorobenzyl)-2-dimethylaminomethyl-1-(3-fluorophenyl)-cyclohexanol;
4-(4-chlorobenzyl)-1-(3-chlorophenyl)-2-dimethylaminomethyl-cyclohexanol;
4-(4-chlorobenzyl)-1-(3,5-dichlorophenyl)-2-dimethylaminomethyl-cyclohexanol;
4-(4-chlorobenzyl)-1-(2-chlorobenzyl)-2-dimethylaminomethyl-cyclohexanol;
4-(4-chlorobenzyl)-2-dimethylaminomethyl-1-(4-fluorobenzyl)-cyclohexanol;
4-(4-chlorobenzyl)-2-dimethylaminomethyl-1-(3-fluorobenzyl)-cyclohexanol;
4-(4-chlorobenzyl)-2-dimethylaminomethyl-1-(2-methoxy-phenyl)-cyclohexanol;
4-(4-chlorobenzyl)-2-dimethylaminomethyl-1-(2-methyl-benzyl)-cyclohexanol;
4-(4-chlorobenzyl)-2-dimethylaminomethyl-1-(3-methyl-benzyl)-cyclohexanol;
1,4-bis-(4-chlorobenzyl)-2-dimethylaminomethyl-cyclohexanol;
4-(4-chlorobenzyl)-1-(2-chloro-6-fluorobenzyl)-2-dimethylaminomethyl-cyclohexanol;
4-(4-chlorobenzyl)-2-dimethylaminomethyl-1-(2,5-dimethyl-benzyl)-cyclohexanol;
4-(4-chlorobenzyl)-1-(3-chlorobenzyl)-2-dimethylaminomethyl-cyclohexanol;
4-(4-chlorobenzyl)-1-(2,4-dichlorobenzyl)-2-dimethylaminomethyl-cyclohexanol;
4-(4-chlorobenzyl)-2-dimethylaminomethyl-1-phenyl-cyclohexanol;
4-(4-chlorobenzyl)-1-(4-chlorophenyl)-2-dimethylaminomethyl-cyclohexanol;
4-(4-chlorobenzyl)-2-dimethylaminomethyl-1-(4-fluoro-3-methyl-phenyl)-cyclohexanol;
4-(4-chlorobenzyl)-2-dimethylaminomethyl-1-o-tolyl-cyclohexanol;
4-(4-chlorobenzyl)-2-dimethylaminomethyl-1-vinyl-cyclohexanol;
4-(4-chlorobenzyl)-1-cyclopentyl-2-dimethylaminomethyl-cyclohexanol;
4-(4-chlorobenzyl)-2-dimethylaminomethyl-1-m-tolyl-cyclohexanol;
4-(4-chlorobenzyl)-2-dimethylaminomethyl-bicyclo-hexyl-1-ol;
4-(4-chlorobenzyl)-2-dimethylaminomethyl-1-(4-fluorophenyl)-cyclohexanol;
4-(4-chlorobenzyl)-2-dimethylaminomethyl-1-phenethyl-cyclohexanol;
4-(4-chlorobenzyl)-2-dimethylaminomethyl-1-phenylethynyl-cyclohexanol;
4-(4-chlorobenzyl)-2-dimethylaminomethyl-1-thiophen-2-yl-cyclohexanol;
4-(4-chlorobenzyl)-2-dimethylaminomethyl-1-p-tolyl-cyclohexanol;
4-(4-chlorobenzyl)-2-dimethylaminomethyl-1-(4-methoxy-phenyl)-cyclohexanol;
4-(4-chlorobenzyl)-2-dimethylaminomethyl-1-trimethylsilanylethynyl-cyclohexanol;
4-(4-chlorobenzyl)-1-(4-chloro-3-trifluoromethyl-phenyl)-2-dimethylaminomethyl-cyclohexanol;
4-(4-chlorobenzyl)-1-(3-chloro-4-fluorophenyl)-2-dimethylaminomethyl-cyclohexanol;
4-(4-chlorobenzyl)-2-dimethylaminomethyl-1-(3-trifluoromethyl-phenyl)-cyclohexanol;
2-dimethylaminomethyl-4-(4-fluorobenzyl)-1-phenyl-cyclohexanol;
1-(4-chlorophenyl)-2-dimethylaminomethyl-4-(4-fluorobenzyl)-cyclohexanol;
1-benzyl-2-dimethylaminomethyl-4-(4-fluorobenzyl)-cyclohexanol;
2-dimethylaminomethyl-4-(4-fluorobenzyl)-1-(4-fluoro-3-methyl-phenyl)-cyclohexanol;
2-dimethylaminomethyl-4-(4-fluorobenzyl)-1-o-tolyl-cyclohexanol;
2-dimethylaminomethyl-4-(4-fluorobenzyl)-1-vinyl-cyclohexanol;
1-(4-tert-butyl-phenyl)-2-dimethylaminomethyl-4-(4-fluorobenzyl)-cyclohexanol;
1-cyclopentyl-2-dimethylaminomethyl-4-(4-fluorobenzyl)-cyclohexanol;
2-dimethylaminomethyl-4-(4-fluorobenzyl)-1-m-tolyl-cyclohexanol;
2-dimethylaminomethyl-4-(4-fluorobenzyl)-bicyclo-hexyl-1-ol;
2-dimethylaminomethyl-4-(4-fluorobenzyl)-1-(4-fluorophenyl)-cyclohexanol;
2-dimethylaminomethyl-4-(4-fluorobenzyl)-1-phenethyl-cyclohexanol;
2-dimethylaminomethyl-4-(4-fluorobenzyl)-1-phenylethynyl-cyclohexanol;
2-dimethylaminomethyl-4-(4-fluorobenzyl)-1-thiophen-2-yl-cyclohexanol;
2-dimethylaminomethyl-4-(4-fluorobenzyl)-1-(3-methoxy-phenyl)-cyclohexanol;
2-dimethylaminomethyl-4-(4-fluorobenzyl)-1-(3-phenyl-propyl)-cyclohexanol;
1-(2,3-dichlorophenyl)-2-dimethylaminomethyl-4-(4-fluorobenzyl)-cyclohexanol;
2-dimethylaminomethyl-4-(4-fluorobenzyl)-1-p-tolyl-cyclohexanol;

2-dimethylaminomethyl-4-(4-fluorobenzyl)-1-(4-methoxy-phenyl)-cyclohexanol;
1-cyclohexylmethyl-2-dimethylaminomethyl-4-(4-fluorobenzyl)-cyclohexanol;
2-dimethylaminomethyl-4-(4-fluorobenzyl)-1-(5-fluoro2-methoxy-phenyl)-cyclohexanol;
2-dimethylaminomethyl-4-(4-fluorobenzyl)-1-(3-fluorophenyl)-cyclohexanol;
1-(3-chlorophenyl)-2-dimethylaminomethyl-4-(4-fluorobenzyl)-cyclohexanol;
1-(3,5-dichlorophenyl)-2-dimethylaminomethyl-4-(4-fluorobenzyl)-cyclohexanol;
1-(2-chlorobenzyl)-2-dimethylaminomethyl-4-(4-fluorobenzyl)-cyclohexanol;
2-dimethylaminomethyl-1,4-bis-(4-fluorobenzyl)-cyclohexanol;
2-dimethylaminomethyl-4-(4-fluorobenzyl)-1-(3-methoxy-benzyl)-cyclohexanol;
1-(4-chloro-3-trifluoromethyl-phenyl)-2-dimethylaminomethyl-4-(4-fluorobenzyl)-cyclohexanol;
2-dimethylaminomethyl-4-(4-fluorobenzyl)-1-(3-fluorobenzyl)-cyclohexanol;
2-dimethylaminomethyl-4-(4-fluorobenzyl)-1-(2-methoxy-phenyl)-cyclohexanol;
2-dimethylaminomethyl-4-(4-fluorobenzyl)-1-(2-methyl-benzyl)-cyclohexanol;
1-(3-chloro-4-fluorophenyl)-2-dimethylaminomethyl-4-(4-fluorobenzyl)-cyclohexanol;
2-dimethylaminomethyl-4-(4-fluorobenzyl)-1-(3-trifluoromethyl-phenyl)-cyclohexanol;
2-dimethylaminomethyl-4-(4-fluorobenzyl)-1-(3-methyl-benzyl)-cyclohexanol;
1-(4-chlorobenzyl)-2-dimethylaminomethyl-4-(4-fluorobenzyl)-cyclohexanol;
1-(2-chloro-6-fluorobenzyl)-2-dimethylaminomethyl-4-(4-fluorobenzyl)-cyclohexanol;
2-dimethylaminomethyl-1-(2,5-dimethyl-benzyl)-4-(4-fluorobenzyl)-cyclohexanol;
1-(3-chlorobenzyl)-2-dimethylaminomethyl-4-(4-fluorobenzyl)-cyclohexanol;
1-(2,4-dichlorobenzyl)-2-dimethylaminomethyl-4-(4-fluorobenzyl)-cyclohexanol;
2-dimethylaminomethyl-4-(3-methoxy-benzyl)-1-phenyl-cyclohexanol;
1-benzyl-2-dimethylaminomethyl-4-(3-methoxy-benzyl)-cyclohexanol;
2-dimethylaminomethyl-1-(4-fluoro-3-methyl-phenyl)-4-(3-methoxy-benzyl)-cyclohexanol;
2-dimethylaminomethyl-4-(3-methoxy-benzyl)-1-o-tolyl-cyclohexanol;
2-dimethylaminomethyl-4-(3-methoxy-benzyl)-1-vinyl-cyclohexanol;
1-(4-tert-butyl-phenyl)-2-dimethylaminomethyl-4-(3-methoxy-benzyl)-cyclohexanol;
1-cyclopentyl-2-dimethylaminomethyl-4-(3-methoxy-benzyl)-cyclohexanol;
2-dimethylaminomethyl-4-(3-methoxy-benzyl)-1-m-tolyl-cyclohexanol;
2-dimethylaminomethyl-4-(3-methoxy-benzyl)-bicyclohexyl-1-ol;
2-dimethylaminomethyl-4-(3-methoxy-benzyl)-1-phenethyl-cyclohexanol;
2-dimethylaminomethyl-4-(3-methoxy-benzyl)-1-phenylethynyl-cyclohexanol;
2-dimethylaminomethyl-4-(3-methoxy-benzyl)-1-thiophen-2-yl-cyclohexanol;

2-dimethylaminomethyl-4-(3-methoxy-benzyl)-1-(3-methoxy-phenyl)-cyclohexanol;
2-dimethylaminomethyl-4-(3-methoxy-benzyl)-1-(3-phenyl-propyl)-cyclohexanol;
1-(2,3-dichlorophenyl)-2-dimethylaminomethyl-4-(3-methoxy-benzyl)-cyclohexanol;
2-dimethylaminomethyl-4-(3-methoxy-benzyl)-1-p-tolyl-cyclohexanol;
1-cyclohexylmethyl-2-dimethylaminomethyl-4-(3-methoxy-benzyl)-cyclohexanol;
2-dimethylaminomethyl-1-(5-fluoro-2-methoxy-phenyl)-4-(3-methoxy-benzyl)-cyclohexanol;
1-(3-chlorophenyl)-2-dimethylaminomethyl-4-(3-methoxy-benzyl)-cyclohexanol;
1-(3,5-dichlorophenyl)-2-dimethylaminomethyl-4-(3-methoxy-benzyl)-cyclohexanol;
1-(4-chloro-3-trifluoromethyl-phenyl)-2-dimethylaminomethyl-4-(3-methoxy-benzyl)-cyclohexanol;
2-dimethylaminomethyl-1-(3-fluorobenzyl)-4-(3-methoxy-benzyl)-cyclohexanol;
2-dimethylaminomethyl-4-(3-methoxy-benzyl)-1-(2-methoxy-phenyl)-cyclohexanol;
2-dimethylaminomethyl-4-(3-methoxy-benzyl)-1-(3-trifluoromethyl-phenyl)-cyclohexanol;
1-(2-chloro-6-fluorobenzyl)-2-dimethylaminomethyl-4-(3-methoxy-benzyl)-cyclohexanol;
2-dimethylaminomethyl-1-(2,5-dimethyl-benzyl)-4-(3-methoxy-benzyl)-cyclohexanol;
1-(3-chlorobenzyl)-2-dimethylaminomethyl-4-(3-methoxy-benzyl)-cyclohexanol;
2-dimethylaminomethyl-4-(4-fluorobenzyloxy)-1-phenyl-cyclohexanol;
1-benzyl-2-dimethylaminomethyl-4-(4-fluorobenzyloxy)-cyclohexanol;
2-dimethylaminomethyl-4-(4-fluorobenzyloxy)-1-(4-fluoro-3-methyl-phenyl)-cyclohexanol;
2-dimethylaminomethyl-4-(4-fluorobenzyloxy)-1-vinyl-cyclohexanol;
1-(4-tert-butyl-phenyl)-2-dimethylaminomethyl-4-(4-fluorobenzyloxy)-cyclohexanol;
1-cyclopentyl-2-dimethylaminomethyl-4-(4-fluorobenzyloxy)-cyclohexanol;
2-dimethylaminomethyl-4-(4-fluorobenzyloxy)-1-m-tolyl-cyclohexanol;
2-dimethylaminomethyl-4-(4-fluorobenzyloxy)~bicyclohexyl-1-ol;
2-dimethylaminomethyl-4-(4-fluorobenzyloxy)-1-phenethyl-cyclohexanol;
2-dimethylaminomethyl-4-(4-fluorobenzyloxy)-1-phenylethynyl-cyclohexanol;
2-dimethylaminomethyl-4-(4-fluorobenzyloxy)-1-thiophen-2-yl-cyclohexanol;
2-dimethylaminomethyl-4-(4-fluorobenzyloxy)-1-(3-methoxy-phenyl)-cyclohexanol;
2-dimethylaminomethyl-4-(4-fluorobenzyloxy)-1-p-tolyl-cyclohexanol;
1-cyclohexylmethyl-2-dimethylaminomethyl-4-(4-fluorobenzyloxy)-cyclohexanol;
2-dimethylaminomethyl-1-(3-fluorobenzyl)-4-(4-fluorobenzyloxy)-cyclohexanol;
2-dimethylaminomethyl-4-(4-fluorobenzyloxy)-1-(2-methoxy-phenyl)-cyclohexanol;
2-dimethylaminomethyl-4-(4-fluorobenzyloxy)-1-(3-methyl-benzyl)-cyclohexanol;
2-dimethylaminomethyl-1-(2,5-dimethyl-benzyl)-4-(4-fluorobenzyloxy)-cyclohexanol;

1-(3-chlorobenzyl)-2-dimethylaminomethyl-4-(4-fluorobenzyloxy)-cyclohexanol;
[5-benzyloxy-2-(3-methoxy-phenyl)-cyclohexylmethyl]-dimethyl-amine;
[5-(3-chlorobenzyloxy)-2-(3-methoxy-phenyl)-cyclohexylmethyl]-dimethyl-amine;
[2-(3-methoxy-phenyl)-5-(naphthalen-2-ylmethoxy)-cyclohexylmethyl]-dimethyl-amine;
[5-(3-methoxy-benzyloxy)-2-(3-methoxy-phenyl)-cyclohexylmethyl]-dimethyl-amine;
[5-(4-chlorobenzyloxy)-2-(3-methoxy-phenyl)-cyclohexylmethyl]-dimethyl-amine;
[5-(4-methoxy-benzyloxy)-2-(3-methoxy-phenyl)-cyclohexylmethyl]-dimethyl-amine;
2-dimethylaminomethyl-1-(3-methoxy-phenyl)-4-(naphthalen-2-ylmethoxy)-cyclohexanol;
butyric acid 3-dimethylaminomethyl-4-hydroxy-4-(3-methoxy-phenyl)-cyclohexylester;
2-dimethylaminomethyl-1-(3-methoxy-phenyl)-4-(naphthalen-2-ylmethoxy)-cyclohexanol;
4-methoxy-benzoic acid 3-dimethylaminomethyl-4-hydroxy-4-(3-methoxy-phenyl)-cyclohexylester;
3-methoxy-benzoic acid 3-dimethylaminomethyl-4-hydroxy-4-(3-methoxy-phenyl)-cyclohexylester;
2,2-dimethyl-propionic acid 3-dimethylaminomethyl-4-hydroxy-4-(3-methoxy-phenyl)-cyclohexylester;
butyric acid 3-dimethylaminomethyl-4-hydroxy-4-(3-methoxy-phenyl)-cyclohexylester;
4-methoxy-benzoic acid 3-dimethylaminomethyl-4-hydroxy-4-(3-methoxy-phenyl)-cyclohexylester;
3-methoxy-benzoic acid 3-dimethylaminomethyl-4-hydroxy-4-(3-methoxy-phenyl)-cyclohexylester;
2,2-dimethyl-propionic acid 3-dimethylaminomethyl-4-hydroxy-4-(3-methoxy-phenyl)-cyclohexylester;
3,4-dimethoxy-benzoic acid 3-dimethylaminomethyl-4-hydroxy-4-(3-methoxy-phenyl)-cyclohexylester;
3,4-dimethoxy-benzoic acid 3-dimethylaminomethyl-4-hydroxy-4-(3-methoxy-phenyl)-cyclohexylester;
naphthalene-2-carboxylic acid 3-dimethylaminomethyl-4-hydroxy-4-(3-methoxyphenyl)-cyclohexylester;
4-methyl-benzoic acid 3-dimethylaminomethyl-4-hydroxy-4-(3-methoxyphenyl)-cyclohexylester;
3,4-dichloro-benzoic acid 3-dimethylaminomethyl-4-hydroxy-4-(3-methoxy-phenyl)-cyclohexylester;
4-chloro-benzoic acid 3-dimethylaminomethyl-4-hydroxy-4-(3-methoxyphenyl)-cyclohexylester;
3-chloro-benzoic acid 3-dimethylaminomethyl-4-hydroxy-4-(3-methoxyphenyl)-cyclohexylester;
2-chloro-benzoic acid 3-dimethylaminomethyl-4-hydroxy-4-(3-methoxyphenyl)-cyclohexylester;
4-trifluoromethyl-benzoic acid 3-dimethylaminomethyl-4-hydroxy-4-(3methoxy-phenyl)-cyclohexylester;
3,5-difluoro-benzoic acid 3-dimethylaminomethyl-4-hydroxy-4-(3-methoxy-phenyl)-cyclohexylester;
4-fluoro-benzoic acid 3-dimethylaminomethyl-4-hydroxy-4-(3-methoxy-phenyl)-cyclohexylester;
3-fluoro-benzoic acid 3-dimethylaminomethyl-4-hydroxy-4-(3-methoxy-phenyl)-cyclohexylester;
2-fluoro-benzoic acid 3-dimethylaminomethyl-4-hydroxy-4-(3-methoxy-phenyl)-cyclohexylester;
cyclopentanecarboxylic acid 3-dimethylaminomethyl-4-hydroxy-4-(3-methoxy-phenyl)-cyclohexylester;
(4-methoxy-phenyl)-acetic acid 3-dimethylaminomethyl-4-hydroxy-4-(3-methoxy-phenyl)-cyclohexylester;
(3-methoxy-phenyl)-acetic acid 3-dimethylaminomethyl-4-hydroxy-4-(3-methoxy-phenyl)-cyclohexylester;
phenyl-acetic acid 3-dimethylaminomethyl-4-hydroxy-4-(3-methoxy-phenyl)-cyclohexylester;
3,4,5-trimethoxy-benzoic acid 3-dimethylaminomethyl-4-hydroxy-4-(3methoxy-phenyl)-cyclohexylester;
3,5-dimethoxy-benzoic acid 3-dimethylaminomethyl-4-hydroxy-4-(3-methoxy-phenyl)-cyclohexylester;
naphthalene-1-carboxylic acid 3-dimethylaminomethyl-4-hydroxy-4-(3-methoxyphenyl)-cyclohexylester;
2-methoxy-benzoic acid 3-dimethylaminomethyl-4-hydroxy-4-(3-methoxy-phenyl)-cyclohexylester;
naphthalene-2-carboxylic acid 3-dimethylaminomethyl-4-hydroxy-4-(3-methoxyphenyl)-cyclohexylester;
2-hydroxy-benzoic acid 3-dimethylaminomethyl-4-hydroxy-4-(3-methoxy-phenyl)-cyclohexylester;
4-methyl-benzoic acid 3-dimethylaminomethyl-4-hydroxy-4-(3-methoxyphenyl)-cyclohexylester;
3,4-dichloro-benzoic acid 3-dimethylaminomethyl-4-hydroxy-4-(3-methoxy-phenyl)-cyclohexylester;
4-chloro-benzoic acid 3-dimethylaminomethyl-4-hydroxy-4-(3-methoxyphenyl)-cyclohexylester;
3-chloro-benzoic acid 3-dimethylaminomethyl-4-hydroxy-4-(3-methoxyphenyl)-cyclohexylester;
2-chloro-benzoic acid 3-dimethylaminomethyl-4-hydroxy-4-(3-methoxyphenyl)-cyclohexylester;
4-trifluoromethyl-benzoic acid 3-dimethylaminomethyl-4-hydroxy-4-(3-methoxy-phenyl)-cyclohexylester;
3,5-difluoro-benzoic acid 3-dimethylaminomethyl-4-hydroxy-4-(3-methoxy-phenyl)-cyclohexylester;
4-fluoro-benzoic acid 3-dimethylaminomethyl-4-hydroxy-4-(3-methoxy-phenyl)-cyclohexylester;
3-fluoro-benzoic acid 3-dimethylaminomethyl-4-hydroxy-4-(3-methoxy-phenyl)-cyclohexylester;
2-fluoro-benzoic acid 3-dimethylaminomethyl-4-hydroxy-4-(3-methoxy-phenyl)-cyclohexylester;
cyclopentanecarboxylic acid 3-dimethylaminomethyl-4-hydroxy-4-(3-methoxy-phenyl)-cyclohexylester;
(4-methoxy-phenyl)-acetic acid 3-dimethylaminomethyl-4-hydroxy-3234-(3-methoxy-phenyl)-cyclohexylester;
(3-methoxy-phenyl)-acetic acid 3-dimethylaminomethyl-4-hydroxy-4-(3-methoxy-phenyl)-cyclohexylester;
phenyl-acetic acid 3-dimethylaminomethyl-4-hydroxy-4-(3-methoxy-phenyl)-cyclohexylester;
3,4,5-trimethoxy-benzoic acid 3-dimethylaminomethyl-4-hydroxy-4-(3-methoxy-phenyl)-cyclohexylester;
3,5-dimethoxy-benzoic acid 3-dimethylaminomethyl-4-hydroxy-4-(3-methoxy-phenyl)-cyclohexylester;
naphthalene-1-carboxylic acid 3-dimethylaminomethyl-4-hydroxy-4-(3-methoxy-phenyl)-cyclohexylester;
2-methoxy-benzoic acid 3-dimethylaminomethyl-4-hydroxy-4-(3-methoxy-phenyl)-cyclohexylester;
2-dimethylaminomethyl-1,4-bis-(3-methoxy-phenyl)-cyclohexane-1,4-diol;
2-dimethylaminomethyl-1,4-bis-(3-methoxy-phenyl)-cyclohexane-1,4-diol;
6-(4-benzyloxy-2-dimethylaminomethyl-1-hydroxy-cyclohexyl)-naphthalen-2-ol;
4-benzyloxy-2-dimethylaminomethyl-1-(6-methoxy-naphthalen-2-yl)-cyclohexanol;
butyric acid 3-dimethylaminomethyl-4-hydroxy-4-(3-methoxy-phenyl)-cyclohexylester;
butyric acid 3-dimethylaminomethyl-4-hydroxy-4-(3-methoxy-phenyl)-cyclohexylester;
2-dimethylaminomethyl-1-(3-methoxy-phenyl)-4-methylamino-cyclohexanol;
2-dimethylaminomethyl-1-(3-methoxy-phenyl-4-methylamino-cyclohexanol;

valeric acid 3-dimethylaminomethyl-4-hydroxy-4-(3-methoxy-phenyl)-cyclohexylester;
[3-dimethylaminomethyl-4-hydroxy-4-(3-methoxy-phenyl)-cyclohexylidene]acetic acid ethylester;
[3-dimethylaminomethyl-4-hydroxy-4-(3-methoxy-phenyl)-cyclohexylidene]acetic acid ethylester;
3-[2-dimethylaminomethyl-4-(4-fluorobenzyloxy)-1-hydroxy-cyclohexyl]-phenol;
4-benzyloxy-2-dimethylaminomethyl-1-(3-phenyl-propyl)-cyclohexanol;
2-dimethylaminomethyl-4-(4-fluorobenzyloxy)-1-(3-phenyl-propyl)-cyclohexanol;
2-dimethylaminomethyl-1-(3-fluorobenzyl)-4-(4-fluorobenzyloxy)-cyclohexanol;
4-benzyloxy-2-dimethylaminomethyl-1-(3-fluorobenzyl)-cyclohexanol;
2-dimethylaminomethyl-4-(4-fluorobenzyloxy)-1-p-tolyl-cyclohexanol;
4-benzyloxy-2-dimethylaminomethyl-1-p-tolyl-cyclohexanol;
2-dimethylaminomethyl-1-(2,5-dimethyl-benzyl)-4-(4-fluorobenzyloxy)-cyclohexanol;
4-benzyloxy-2-dimethylaminomethyl-1-(2,5-dimethyl-benzyl)-cyclohexanol;
1-(4-chloro-3-trifluoromethyl-phenyl)-2-dimethylaminomethyl-4-(4-fluor-benzyloxy)-cyclohexanol;
4-benzyloxy-1-(4-chloro-3-trifluoromethyl-phenyl)-2-dimethylaminomethyl-cyclohexanol;
[2,5-bis-(4-fluorobenzyloxy)-2-(3-methoxy-phenyl)-cyclohexylmethyl]-dimethylamine;
butyric acid 3-dimethylaminomethyl-4-hydroxy-4-(6-methoxynaphthalen-2-yl)-cyclohexylester;
benzoic acid 4-hydroxy-3-(4-methyl-piperazin-1-ylmethyl)-4-naphthalen-2-yl-cyclohexyl ester;
2-chloro-benzoic acid 4-hydroxy-3-(4-methyl-piperazin-1-ylmethyl)-4-naphthalen-2-yl-cyclohexyl ester;
3-chloro-benzoic acid 4-hydroxy-3-(4-methyl-piperazin-1-ylmethyl)-4-naphthalen-2-yl-cyclohexyl ester;
4-chloro-benzoic acid 4-hydroxy-3-(4-methyl-piperazin-1-ylmethyl)-4-naphthalen-2-yl-cyclohexyl ester;
2-fluoro-benzoic acid 4-hydroxy-3-(4-methyl-piperazin-1-ylmethyl)-4-naphthalen-2-yl-cyclohexyl ester;
3-fluoro-benzoic acid 4-hydroxy-3-(4-methyl-piperazin-1-ylmethyl)-4-naphthalen-2-yl-cyclohexyl ester;
4-fluoro-benzoic acid 4-hydroxy-3-(4-methyl-piperazin-1-ylmethyl)-4-naphthalen-2-yl-cyclohexyl ester;
2-methyl-benzoic acid 4-hydroxy-3-(4-methyl-piperazin-1-ylmethyl)-4-naphthalen-2-yl-cyclohexyl ester;
3-methyl-benzoic acid 4-hydroxy-3-(4-methyl-piperazin-1-ylmethyl)-4-naphthalen-2-yl-cyclohexyl ester;
4-methyl-benzoic acid 4-hydroxy-3-(4-methyl-piperazin-1-ylmethyl)-4-naphthalen-2-yl-cyclohexyl ester;
2-methoxy-benzoic acid 4-hydroxy-3-(4-methyl-piperazin-1-ylmethyl)-4-naphthalen-2-yl-cyclohexyl ester;
3-methoxy-benzoic acid 4-hydroxy-3-(4-methyl-piperazin-1-ylmethyl)-4-naphthalen-2-yl-cyclohexyl ester;
4-methoxy-benzoic acid 4-hydroxy-3-(4-methyl-piperazin-1-ylmethyl)-4-naphthalen-2-yl-cyclohexyl ester;
2,6-dichloro-benzoic acid 4-hydroxy-3-(4-methyl-piperazin-1-ylmethyl)-4-naphthalen-2-yl-cyclohexyl ester;
2,6-difluoro-benzoic acid 4-hydroxy-3-(4-methyl-piperazin-1-ylmethyl)-4-naphthalen-2-yl-cyclohexyl ester;
2-chloro5-fluoro-benzoic acid 4-hydroxy-3-(4-methyl-piperazin-1-ylmethyl)-4-naphthalen-2-yl-cyclohexyl ester;
biphenyl-4-carboxylic acid 4-hydroxy-3-(4-methyl-piperazin-1-ylmethyl)-4-naphthalen-2-yl-cyclohexylester;
2-chloro-benzoic acid 4-hydroxy-4-(6-methoxy-naphthalen-2-yl)-3-(4-methyl piperazin-1-ylmethyl)-cyclohexyl ester;
3-chloro-benzoic acid 4-hydroxy-4-(6-methoxy-naphthalen-2-yl)-3-(4-methyl-piperazin-1-ylmethyl)-cyclohexyl ester;
4-chloro-benzoic acid 4-hydroxy-4-(6-methoxy-naphthalen-2-yl)-3-(4-methyl-piperazin-1-ylmethyl)-cyclohexyl ester;
2-fluoro-benzoic acid 4-hydroxy-4-(6-methoxy-naphthalen-2-yl)-3-(4-methyl-piperazin-1-ylmethyl)-cyclohexyl ester;
3-fluoro-benzoic acid 4-hydroxy-4-(6-methoxy-naphthalen-2-yl)-3-(4-methyl piperazin-1-ylmethyl)-cyclohexyl ester;
4-fluoro-benzoic acid 4-hydroxy-4-(6-methoxy-naphthalen-2-yl)-3-(4-methyl piperazin-1-ylmethyl)-cyclohexyl ester;
2-methyl-benzoic acid 4-hydroxy-4-(6-methoxy-naphthalen-2-yl)-3-(4-methyl-piperazin-1-ylmethyl)-cyclohexyl ester;
3-methyl-benzoic acid 4-hydroxy-4-(6-methoxy-naphthalen-2-yl)-3-(4-methyl-piperazin-1-ylmethyl)-cyclohexyl ester;
4-methyl-benzoic acid 4-hydroxy-4-(6-methoxy-naphthalen-2-yl)-3-(4-methyl-piperazin-1-ylmethyl)-cyclohexyl ester;
2-methoxy-benzoic acid 4-hydroxy-4-(6-methoxy-naphthalen-2-yl)-3-(4-methyl-piperazin-1-ylmethyl)-cyclohexyl ester;
3-methoxy-benzoic acid 4-hydroxy-4-(6-methoxy-naphthalen-2-yl)-3-(4-methyl-piperazin-1-ylmethyl)-cyclohexyl ester;
4-methoxy-benzoic acid 4-hydroxy-4-(6-methoxy-naphthalen-2-yl)-3-(4-methyl-piperazin-1-ylmethyl)-cyclohexyl ester;
2,6-dichloro-benzoic acid 4-hydroxy-4-(6-methoxy-naphthalen-2-yl)-3-(4-methyl-piperazin-1-ylmethyl)-cyclohexyl ester;
2,6-fluoro-benzoic acid 4-hydroxy-4-(6-methoxy-naphthalen-2-yl)-3-(4-methyl piperazin-1-ylmethyl)-cyclohexyl ester;
2-chloro-6-fluoro-benzoic acid 4-hydroxy-4-(6-methoxy-naphthalen-2-yl)-3-(4-methyl-piperazin-1-ylmethyl)-cyclohexyl ester;
biphenyl-4-carboxylic acid 4-hydroxy-4-(6-methoxy-naphthalen-2-yl)-3-(4-methyl-piperazin-1-ylmethyl)-cyclohexyl ester;
4-(2-chlorobenzyloxy)-2-(4-methyl-piperazin-1-ylmethyl)-1-naphthalen-2-yl-cyclohexanol;
4-(3-chlorobenzyloxy)-2-(4-methyl-piperazin-1-ylmethyl)-1-naphthalen-2-yl-cyclohexanol;
4-(4-chlorobenzyloxy)-2-(4-methyl-piperazin-1-ylmethyl)-1-naphthalen-2-yl-cyclohexanol;
4-(2-fluorobenzyloxy)-2-(4-methyl-piperazin-1-ylmethyl)-1-naphthalen-2-yl-cyclohexanol;
4-(3-fluorobenzyloxy)-2-(4-methyl-piperazin-1-ylmethyl)-1-naphthalen-2-yl-cyclohexanol;
4-(4-fluorobenzyloxy)-2-(4-methyl-piperazin-1-ylmethyl)-1-naphthalen-2-yl-cyclohexanol;
4-(2-methyl-benzyloxy)-2-(4-methyl-piperazin-1-ylmethyl)-1-naphthalen-2-yl-cyclohexanol;
4-(3-methyl-benzyloxy)-2-(4-methyl-piperazin-1-ylmethyl)-1-naphthalen-2-yl-cyclohexanol;
4-(4-methyl-benzyloxy)-2-(4-methyl-piperazin-1-ylmethyl)-1-naphthalen-2-yl-cyclohexanol;

4-(2-methoxy-benzyloxy)-2-(4-methyl-piperazin-1-ylmethyl)-1-naphthalen-2-yl-cyclohexanol;
4-(3-methoxy-benzyloxy)-2-(4-methyl-piperazin-1-ylmethyl)-1-naphthalen-2-yl-cyclohexanol;
4-(4-methoxy-benzyloxy)-2-(4-methyl-piperazin-1-ylmethyl)-1-naphthalen-2-yl-cyclohexanol;
4-(2,6-dichlorobenzyloxy)-2-(4-methyl-piperazin-1-ylmethyl)-1-naphthalen-2-yl-cyclohexanol;
4-(2,6-difluorobenzyloxy)-2-(4-methyl-piperazin-1-ylmethyl)-1-naphthalen-2-yl-cyclohexanol;
4-(2-chloro-6-fluorobenzyloxy)-2-(4-methyl-piperazin-1-ylmethyl)-1-naphthalen-2-yl-cyclohexanol;
4-(2-chlorobenzyloxy)-1-(6-methoxy-naphthalen-2-yl)-2-(4-methyl-piperazin-1-ylmethyl)-cyclohexanol;
4-(3-chlorobenzyloxy)-1-(6-methoxy-naphthalen-2-yl)-2-(4-methyl-piperazin-1-ylmethyl)-cyclohexanol;
4-(4-chlorobenzyloxy)-1-(6-methoxy-naphthalen-2-yl)-2-(4-methyl-piperazin-1-ylmethyl)-cyclohexanol;
4-(2-fluorobenzyloxy)-1-(6-methoxy-naphthalen-2-yl)-2-(4-methyl-piperazin-1-ylmethyl)-cyclohexanol;
4-(3-fluorobenzyloxy)-1-(6-methoxy-naphthalen-2-yl)-2-(4-methyl-piperazin-1-ylmethyl)-cyclohexanol;
4-(4-fluorobenzyloxy)-1-(6-methoxy-naphthalen-2-yl)-2-(4-methyl-piperazin-1-ylmethyl)-cyclohexanol;
4-(2-methyl-benzyloxy)-1-(6-methoxy-naphthalen-2-yl)-2-(4-methyl-piperazin-1-ylmethyl)-cyclohexanol;
4-(3-methyl-benzyloxy)-1-(6-methoxy-naphthalen-2-yl)-2-(4-methyl-piperazin-1-ylmethyl)-cyclohexanol;
4-(4-methyl-benzyloxy)-1-(6-methoxy-naphthalen-2-yl)-2-(4-methyl-piperazin-1-ylmethyl)-cyclohexanol;
4-(2-methoxy-benzyloxy)-1-(6-methoxy-naphthalen-2-yl)-2-(4-methyl-piperazin-1-ylmethyl)-cyclohexanol;
4-(3-methoxy-benzyloxy)-1-(6-methoxy-naphthalen-2-yl)-2-(4-methyl-piperazin-1-ylmethyl)-cyclohexanol;
4-(4-methoxy-benzyloxy)-1-(6-methoxy-naphthalen-2-yl)-2-(4-methyl-piperazin-1-ylmethyl)-cyclohexanol;
4-(2,6-dichlorobenzyloxy)-1-(6-methoxy-naphthalen-2-yl)-2-(4-methyl-piperazin-1-ylmethyl)-cyclohexanol;
4-(2,6-difluorobenzyloxy)-1-(6-methoxy-naphthalen-2-yl)-2-(4-methyl-piperazin-1-ylmethyl)-cyclohexanol;
4-(2-chloro-6-fluorobenzyloxy)-1-(6-methoxy-naphthalen-2-yl)-2-(4-methyl-piperazin-1-ylmethyl)-cyclohexanol;
2-dimethylaminomethyl-4-(4-fluorobenzyloxy)-1-naphthalen-2-yl-cyclohexanol;
4-fluoro-benzoic acid 3-dimethylaminomethyl-4-hydroxy-4-(6-methoxy-naphthalen-2-yl)-cyclohexylester;
4-fluoro-benzoic acid 3-dimethylaminomethyl-4-hydroxy-4-naphthalen-2-yl-cyclohexylester;
2-dimethylaminomethyl-4-(4-fluorobenzyloxy)-1-(6-methoxy-naphthalen-2-yl)-cyclohexanol; and
6-[2-dimethylaminomethyl-4-(4-fluorobenzyloxy)-1-hydroxy-cyclohexyl]-naphthalen-2-ol.

51. A pharmaceutical composition comprising at least one compound according to claim 1, and a pharmaceutically acceptable excipient.

52. A pharmaceutical composition according to claim 51, wherein the compound is in the form of a pure diastereomer or enantiomer.

53. A pharmaceutical composition according to claim 51, wherein the compound is in the form of a racemate or equimolar mixture of diastereomers.

54. A pharmaceutical composition according to claim 51, wherein the compound is in the form of a non-equimolar mixture of enatiomers or non-equimolar mixture of diastereomers.

55. A method for the treatment of pain, comprising administering an effective amount of a pharmaceutical composition according to claim 51 to a patient in need thereof.

56. A method according to claim 55, wherein the pain is neuropathic or chronic pain.

\* \* \* \* \*